(12) United States Patent
Griffin et al.

(10) Patent No.: US 7,928,199 B2
(45) Date of Patent: Apr. 19, 2011

(54) STABILIZED PROTEINS WITH ENGINEERED DISULFIDE BONDS

(75) Inventors: John H. Griffin, Del Mar, CA (US); Andrew J. Gale, San Diego, CA (US); Elizabeth D. Getzoff, San Diego, CA (US); Jean-Luc Pellequer, Cedex (FR)

(73) Assignee: The Scripps Research Institute, La Jolla, CA (US)

( * ) Notice: Subject to any disclaimer, the term of this patent is extended or adjusted under 35 U.S.C. 154(b) by 688 days.

(21) Appl. No.: 11/627,197

(22) Filed: Jan. 25, 2007

(65) Prior Publication Data

US 2007/0276128 A1    Nov. 29, 2007

Related U.S. Application Data

(62) Division of application No. 10/172,712, filed on Jun. 14, 2002, now Pat. No. 7,205,278.

(60) Provisional application No. 60/298,578, filed on Jun. 14, 2001.

(51) Int. Cl.
*C07K 14/755* (2006.01)
*A61K 38/36* (2006.01)

(52) U.S. Cl. ............................. 530/383; 530/350; 514/2

(58) Field of Classification Search ........................ None
See application file for complete search history.

(56) References Cited

U.S. PATENT DOCUMENTS

| | | | |
|---|---|---|---|
| 4,749,780 A | 6/1988 | Andersson et al. | 530/383 |
| 4,757,006 A | 7/1988 | Toole, Jr. et al. | 435/69.6 |
| 4,853,871 A | 8/1989 | Pantoliano et al. | 701/99 |
| 4,868,112 A | 9/1989 | Toole, Jr. | 514/8 |
| 4,877,614 A | 10/1989 | Andersson et al. | 424/94.64 |
| 5,009,889 A | 4/1991 | Taylor, Jr. et al. | 424/94.64 |
| 5,082,767 A | 1/1992 | Hatfield et al. | 435/6 |
| 5,198,349 A | 3/1993 | Kaufman | 364/69.6 |
| 5,214,033 A | 5/1993 | Zimmerman et al. | 514/21 |
| 5,422,260 A | 6/1995 | Kaufman et al. | 514/21 |
| 5,453,937 A | 9/1995 | Srinivasan et al. | 364/496 |
| 5,543,149 A | 8/1996 | Rubin | 424/405 |
| 5,661,008 A * | 8/1997 | Almstedt et al. | 435/69.6 |
| 5,747,654 A | 5/1998 | Pastan et al. | 530/391.7 |
| 5,804,181 A * | 9/1998 | Eibl et al. | 424/94.1 |
| 5,849,688 A | 12/1998 | Townes et al. | 514/6 |
| 5,869,292 A | 2/1999 | Voorberg | 435/69.6 |
| 6,114,148 A | 9/2000 | Seed et al. | 435/91.1 |
| 6,180,371 B1 | 1/2001 | Lollar | 435/69.6 |
| 6,262,238 B1 | 7/2001 | Steipe et al. | 530/387.3 |
| 6,353,090 B1 | 3/2002 | Pierschbacher et al. | 530/333 |
| 6,358,703 B1 | 3/2002 | Cho et al. | 435/69.1 |

FOREIGN PATENT DOCUMENTS

| | | |
|---|---|---|
| WO | WO 93/20093 | 10/1993 |
| WO | WO 93/20212 | 10/1993 |
| WO | WO 96/21035 | 7/1996 |
| WO | WO 96/36366 | 11/1996 |
| WO | WO 98/34640 | 8/1998 |
| WO | WO 03/087355 | 10/2003 |

OTHER PUBLICATIONS

Clarke et al. "Engineered Disulfide Bonds as Probes of the Folding Pathway of Barnase: Increasing the Stability of Proteins against the Rate of Denaturation," Biochemistry, vol. 32, pp. 4322-4329. 1993*
Gopal et al. "Cavity-Creating Mutation at the Dimer Interface of Plasmodium falciparum Triosephosphate Isomerase: Restoration of Stability by Disulfide Cross-Linking of Subunits," Biochemistry, vol. 38, pp. 478-486. 1999*
File Hcaplus on STN abstract, AN NO 2000:477360. Dandekar, Thomas. Crystal structures of the membrane-binding C2 domain of human coagulation factor V structure of the C2 domain of human factor VIII at 1.5 Å. Chemtracts (2000), vol. 13, No. 6. Abstract only.*
Velanker et al. 'Disulfide engineering at the dimer interface of Lactobacillus casei thymidylate synthase: Crystal structure of the T155C0E188C0C244T mutant.' Protein Science, vol. 8, pp. 930-933. 1999.*
European Search Report for corresponding European application No. EP09159506, Date Mailed—Sep. 16, 2009; Date Completed Search—Sep. 3, 2009 (herein below references cited in the EP Search Report).
Kaufman et al., "Can We Improve On Nature? Super Molecules of Factor VIII", *Haemophilia*, Blackwell Science, Oxford, Great Britain, 4(4):370-379 (Jul. 1998).
Hazes et al., "Model Building of Disulfide Bonds in Proteins with Known Three Dimensional Structure", *Protein Engineering*, Oxford University Press, Surrey, Great Britain, 2(2):119-125 (1988).
Sowdhamini et al., "Stereochemical Modeling Of Disulfide Bridges. Criteria For Introduction Into Proteins By Site-Directed Mutagenesis", *Protein Engineering*, Oxford University Press, Surrey, Great Britain, 3(2):95-103 (1989).
Abkevich et al., "What Can Disulfide Bonds Tell Us About Protein Energetics, Function And Folding: Simulations And Bioinformatics Analysis", *Journal of Molecular Biology*, 300(4):975-985 (Jul. 21, 2000).
Dani et al., "MODIP revisited: re-evaluation and refinement of an automated procedure for modeling of disulfide bonds in proteins", *Protein Engineering*, 16(3):187-193 (Mar. 2003).
Gale et al., "Interdomain Engineered Disulfide Bond Permitting Elucidation Of Mechanisms Of Inactivation Of Coagulation Factor Va By Activated Protein C", *Protein Science: A Publication Of The Protein Society*, 11(9):2091-2101 (Sep. 2002).

(Continued)

*Primary Examiner* — Anish Gupta
(74) *Attorney, Agent, or Firm* — Thomas Fitting; Evelyn M. Kwon; Melissa B. Wenk

(57) ABSTRACT

The present invention relates to methods of introducing one or more cysteine residues into a polypeptide which permit the stabilization of the polypeptide by formation of at least one bond, preferably a disulfide bond, between different domains of the polypeptide. The invention also relates to polypeptides containing such introduced cysteine residue(s), nucleic acids encoding such polypeptides and pharmaceutical compositions comprising such polypeptides or nucleic acids. The invention also relates to vectors, viral particles and host cells containing such nucleic acids, and methods of using them to produce the polypeptides of the invention. Exemplified polypeptides include plasma proteins, including hepatocyte growth factor activator and plasma hyaluronin binding protein, as well as blood coagulation factors, such as Factor VIII, Factor V, Factor XII and prothrombin.

4 Claims, 49 Drawing Sheets

OTHER PUBLICATIONS

Gale et al., "An Engineered Interdomain Disulfide Bond Stabilizes Human Blood Coagulation Factor VIIIa", *Journal of Thrombosis and Haemostatis*, 1(9):1966-1971 (2003).

Reiter et al: "Disulfide stabilization of antibody Fv: Computer Predictions and Experimental Evaluation." *Protein Engineering*, vol. 8, No. 12 pp. 1323-1331, Dec. 1995.

Aly et al: "Cysteamine Enhances the Procoagulant Activity of Factor VIII-East Hartford A Dysfunctional Protein Due to a Light Chain Thrombin Cleavage Site Mutation Arginine-1689 to Cystein", *Journal of Clinical Investigation*, vol. 89, No. 5, pp. 1375-1381, 1992.

Aly et al: "The Substitution of Cystein for Arginine-1689 In Factor VIII-East Hartford Reduces its Procoagulant Activity through Formation of a Disulfide Bond", *Clinical Research*, vol. 38 No. 2, p. 427A, 1992.

Pantoliano et al. "Protein Engineering of Substilsin BPN'": Enhanced Stablization Throught the Intorudction of Two Cysteines to Form a Disulfide Bond. *Biochemistry*, vol. 26, pp. 2077-2082. 1987.

Arai et al. "Characterization of Thrombin Cleavage Site Mutation (ARG 1689 to CYS) in the Factor VIII Gene of Two Unrelated Patients With Cross-Reacting Material-Positive Hemophilia A." *Blood* vol. 75, No. 2, pp. 384-389. Jan. 15, 1990.

Boedeker, B. G. D., "Production Processes of Licensed Recombinant Factor VIII Preparations," *Seminars in Thrombosis and Hemostasis*, 27(4):385-394, Aug. 2001.

Bray, G.L. et al., "A Multicenter Study of Recombinant Factor VII (Recombinant): Safety, Efficacy, and Inhibitor Risk in Previously Untreated Patents With Hemophilia A," *Blood*, 83Q:2428-2435, May 1, 1994.

Brinkhouse, K.M. et al., "Purified human factor VIII procoagulant protein: Comparative hemostatus response after infusions into hemophilic and von Willebrand disease dogs," *Proc. Natl. Acad. Sci. USA*, 82:8752-8756, Dec. 1985.

Chao, H. et al., "Sustained expression of human factor VIII in mice using a parvovirus-based vector," *Blood*, 95(5): 1594-1599, Mar. 2000.

Chao, H. et al., "Induction of tolerance to human factor VIII in mince," (httyp://www.ncbi.nlm.nih.gov:80/entrez/q . . . PubMed &list uids=11342466&dopt=Abstract), *Blood*, 97(10):3311-3312, May 15, 2001.

Choi-Miura, N-H et al. "Purification and Characterization of a Novel Hyaluronan-Binding Protein (PHBP) from Human Plasma: It Has Three EGF, a Kringle and a Serine Protease Domain, Similar to Hepatocyte Factor Activator," *J. Biochem*, 119:1157-1165, 1996.

Cochrane, G.G. et al. The Biochemistry and Pathophysiology of the Contact System of Plasma, *Advances In Immunology*, 33:241-306, 1982.

Colman, R.W. et al., "Biologic Activities of the Contact Factors In Vivo," *Thromb. Haemost*, 82:1568-1577, 1999.

Cool, D.E. et al., "Characterization of Human Blood Coagulation Factor XII cDNA," *J. Bio. Chem.*, 260(25): 13666-13676, Nov. 5, 1985.

Cote, H.C.F. et al., "Functional Characterization of Recombinant Human Meizothrombin and Meizothrombin (desF1)," *J. Biol. Chem.*, 272(10):6194-6200, Mar. 1997.

Dela Cadena, R.A. Wachtfogel, YT and Colman RW. Contact Activation Pathway: Inflammation and Coagulation. In *Hemostasis and Thrombosis: Basic Principles and Clinical Practice*, Third Edition. Eds. RW Colman, J Hirsch, VJ Marder and EW Saltzman. JB Lippincott Company, Philadelphia, 1994.

Doyle, M.F. et al., "Meizothrombin: Active Intermediate Formed during Prothrombinase-Catalyzed Activation of Prothrombin," *Methods Enzymol*, 222:299-312, 1990.

Edge, M.D. et al., "Total synthesis of a human leukocyte interferon gene," *Nature*, 292:756-762, Aug. 20, 1981.

Fass, D.N. et al., "Monoclonal Antibodies to Porcine Factor VIII Coagulant and Their Use in the Isolation of Active Coagulant Protein," *Blood*, 59(3):594-600, Mar. 1982.

Fay, P.J. et al., "Model for the Factor VIIIa-dependent Decay of the Intrinsic Factor Xase," *J. Biol. Chem.*, 271(11):6027-6032, Mar. 1996.

Friezner Degen, S.J. et al, "Characterization of the complementary Deoxyribonucleic Acid and Gene Coding for Human Prothrombin," *Biochemistry*, 22(9):2087-2097, Apr. 26, 1983.

Fulcher, C.A. et al., "Characterization of the human factor VIII procoagulant protein with a heterologous precipitating antibody," *Proc. Natl. Acad. Sci. USA*, 79:1648-1652, Mar. 1982.

Gale et al., "Mechanism Of Factor Va Inactivation By Activated Protein C Clarified Using Engineered Disulfide Bond Between A2 and A3 Domains in Va," Abstract No. OC869, Supplement to *Thromb & Haemos*, 84:849-857, 2000.

Giangrande, P. L. F., "Safety and efficacy of KOGENATE® Bayer in previously untreated patients (PUPS) and minimally treated patients (MTPs)," *Haemophilia*, 8(Suppl. 2): 19-22, 2002.

Gitschier, J. et al., "Characterization of the human factor VIII gene," *Nature*, 312:326-330, Nov. 22, 1984.

Griffin, J.H. et al, "Recent Advances In The Understanding of Contact Activation Reactions," *Seminars in Thrombosis and Homeostasis*, 5(4):254-273, 1979.

Hackeng, T.M. et al., "Protein C activation on endothelial cells by prothrombin activation products generated *in situ*: meizothrombin is a better protein C activator than—thrombin," *Biochem. J.*, 319:399-405, 1996.

High, K.A., "Gene Transfer as an Approach to Treating Hemophilia," *Circ Research*, 88:137-144, 2001.

Huggett, B. et al., "EntreMed, Cell Genesys Report Promising Cancer Gene Therapy: GenStar Therapeutics Corp.," (excerpt), *BioWorld Today*, p. 4, Jun. 2001.

Jay, E. et al., "Chemical Synthesis of a Biologically Active Gene for Human Immune Interferon-" *J. Biol. Chem.* 259(10):6311-6317, May 25, 1984.

Jenny, R.. et al., "Compete cDNA and derived amino acid sequence of human factor V," *Proc. Natl. Acad. Sci. USA*, 84(14):4846-4850, Jul. 1987.

Kafri, T. et al., "Sustained expression of genes delivered directly into liver and muscle by lentiviral vectors," *Nature Genetics*, 17:314-317, Nov. 1997.

Lacroix-Desmazes, S. et al., "The Prevalence of Proteolytic Antibodies Against Factor VIII in Hemophilia A," *N. Engl. J. Med.*, 346(9):662-667, Feb. 28, 2002.

Lind, P. et al., "Novel forms of B-domain-deleted recombinant factor VIII molecules: Construction and biochemical characterization," *Eur. J. Biochem.*, 232(1):19-27, Aug. 1994.

Lusher, J.M. et al., "Antibody and Inhibitor Patterns in Previously Untreated Patients (PUPs) Treated Exclusively With B-Domain Deleted Recombinant Factor VIII (BDDrFVIII)," *Blood*. 96:266a, Abstract #1144, 2000.

Lusher, J.M. et al., "Recombinant Factor VIII for the Treatment Of Previously Untreated Patients With Hemophilia A," *New Engl. J. Med.*, 328(7):453-459, Feb. 18, 1993.

Mann, K.G. et al., "Prothrombin and Thrombin," *Hemostasis and Thrombosis: Basic Principles and Clinical Practice*. Third Edition, Chapter 9, 184-199, 1994.

Mannucci, P.M. et al., "The Hemophilias—From Royal Genes to Gene Therapy," *The New England Journal of Medicine*, 344(23):1773-1779, Jun. 2001.

Martin, P.D. et al. "New insights into the regulation of the blood clotting cascade derived from the X-ray crystal structure of bovine meizothrombin des F1 in complex with PPACK," *Structure*, 5(12):1681-1693, Dec. 1997.

Maruyama, T. et al., "Codon usage tabulated from the GenBank genetic sequence data," *Nucleic Acids Research*, 14(5):r141-r197, 1986.

Miller, D.G. et al, "Gene Therapy for Hemophilia," *The New England Journal of Medicine*, 344(23_):1782-1784, Jun. 2001.

Miyazawa, K. et al., "Molecular Cloning and Sequence Analysis of the cDNA for a Human Serine Responsible for Activation of Hepatocyte Growth Factor," *The Journal of Biological Chemistry*, 268(14): 10024-10028, 1993.

Miyazawa K. et al., "Structural organization and chromosomal localization of the human hepatocyte growish factor activator gene: Phylogenetic and functional relationship with blood coagulation factor XII, urokinase, and tissue-type plasminogen activator," *Eur J Biochem*. 258(2):355-61, 1998.

Nambiar, K.P. et al., "total Synthesis and Cloning of a gene Coding for the Ribonuclease S Protein," *Science*, 223(4642):1299-1301, Mar. 23, 1984.

Österberg, T. et al., "Development of a Freeze-Dried Albumin-Free Formulation of Recombinant Factor VIII SQ," Pharm. Res., 14(7):892-898, Jul. 1997.

Pellequer, J.L. et al., "Three-dimensional Model of Coagulation Factor Va Bound to Activated Protein C," *Thromb Haemost.*, 84-849-857, 2000.

Pemberton, S. et al., "A Molecular Model for the Triplicated A Domains of Human Factor VIII Based on the Crystal Structure of Human Ceruloplasmin," *Blood*, 89(7):2413-2421, Apr. 1, 1997.

Pipe, S.W. and Kaufman, R.J., "Characterization of a genetically engineered inactivation-resistance coagulation factor VIIIa," *Proc. Natl. Acad. Sci. USA*, 94:11851-11856, Oct. 1997.

Pipe, S.W. et al., "Mild Hemophilia A Caused by Increased Rate of Factor VIII A2 Subunit Dissociation: Evidence for Nonproteolytic Inactivation of Factor VIIIa In Vivo," Blood, 93(1):176-183, Jan. 1, 1999.

Pittman, D.D. et al., "A2 Domain of Human Recombinant-Derived Factor VIII Is Required for Procoagulant Activity but not for Thrombin Cleavage," *Blood*, 79(2):389-397, Jan. 15, 1992.

Reiter, Y. et al., "Disulfide stabilization of antibody Fv: computer predictions and experimental evaluation," *Protein Engineering*, 8(12):1323-1331, 1995.

Roberts, H.R. and Jones, M.R., "Disorders of hemostasis: Congenital disorders of blood coagulation factor," *Hematology*, Fourth ed., Section 14, Chapter 153:1453-1473, 1990.

Roth, D.A. et al., "Nonviral Transfer Of The Gene Encoding Coagulation Factor VIII in Patients With Severe Hemophilia A," *The New England Journal Of Medicine*, 344(23):1735-1742, Jun. 2001.

Rothschild, C. et al., "European data of a clinical trial with a sucrose formulated recombinant factor VIII in previously treated hemophilia A patients," *Haemophilia*, 8(s.2):10-14, Mar. 2002.

Schwartz, R.S. et al., "Human Recombinant DNA-Derived Antihemophilic Factor (Factor VIII) In the Treatment of Hemophilia A," *N. Engl. J. of Med.*, 323(26):1800-1805, Dec. 27, 1990.

Stollar, B.D., "Proteolytic Antibodies Against Factor VIII In Hemophilia A," *N. Eng. J. Med.*, 346(9):702-703, Feb. 28, 2002.

Sowdhamini, R. et al., "Stereochemical modeling of disulfide bridges. Criteria for introduction into proteins by site-directed mutagenesis," *Protein Eng.*, 3(2):95-103, 1989.

Toole, J.J. et al., "A large region (95kDa) of human factor VIII is dispensable for in vitro procoagulant activity," *Proc. Natl. Acad. Sci. USA*, 83(16):5939-5942, Aug. 1986.

Toole, J.J. et al., "Molecular cloning of a cDNA encoding human antihaemophilic factor," Nature, 312(5992);343-347, Nov. 1984.

Ulmer, J.B. et al., "Heterologous Protection Against Influenza by Injection of DNA Encoding a Viral Protein," Science, 259:1745-1749, Mar. 19, 1993.

Vehar, G.A. et al., "Structure of human factor VIII," *Nature*, 312(5992):337-342, Nov. 22, 1984.

Wang, L. et al, "Sustained Expression of Theraputic level of Factor IX in Hemophilia B Dogs by AAV Mediated Gene Therapy," *Molecular Therapy*, 1(5):Abstract #32, May 2000.

Walter, J. et al., "Gene Therapy for the Hemophilias," *Adv Vet Med.*, 40:119-34, 1997.

White II, G.C. et al., "A Mulitcenter Study of Recombinant Factor VIII (Recombinate™) in Previously Treated Patients with Hemophilia A," *Thromb. And Homost.*, 77(4):660-667, Apr. 1997.

Wolff, J. A.. et al., "Direct Gene Transfer into Mouse Muscle in Vivo," Science, 247:1465-1468, Mar. 23, 1990.

Wolff, J. A.. et al., "Long-term persistence of plasmid DNA and foreign gene expression in mouse muscle," *Human Molecular Genetics*, 1(6):363-369, Sep. 1992.

Wood, W.I. et al., "Expression of Active Human Factor VIII from Recombinant DNA Clones," *Nature*, 312(5992):330-337, Nov. 22, 1984.

Zuker, M. and Stiegler, P., "Optimal Computer Folding of Large RNA Sequences Using Thermodynamics and Auxiliary Information," *Nucleic Acids Research*, 9(1):133-148, 1981.

Davie E.W.: Fujikawa, K.; Kisiel, W.: "The Coagulation Cascade: Initiation, Maintenance, and Regulation", *Biochemistry* vol. 30, 1991, pp. 10363-10370.

Esmon, C. T.: "Regulation of Blood Coagulation", *Biochem. Biophys. ACTA* vol. 1477, 2000, pp. 349-360.

Dahlback, B.: "Blood Coagulation", *Lancet* vol. 355, 2000, pp. 1627-1632.

Esmon, C.T. "The Subunit Structure of Thrombin-Activated Factor V. Isolation of Activated Factor V, Separation of Subunits, and Reconstitution of Biological Activity," *J Biol. Chem.*, vol. 254, 1979, pp. 964-973.

Nesheim, N. E.; Taswell, J.B.; Mann, K.G.: "The Contribution of Bovine Factor V and Factor Va to the Activity of Prothrombinase," *J Biol. Chem.*, vol. 254, 1979, pp. 10952-10962.

Kalafatis, M.; Rand, M.D.; Mann, K.G.: "The Mechanism of Inactivation of Human Factor V and Human Factor Va by Activated Protein C," *J. Biol. Chem.*, vol. 269, 1994, pp. 31869-31880.

Nicolaes, G.A.F. et al.: "Peptide Bond Cleavages and Loss of Functional Activity During Inactivation of Factor Va and Factor VaR506Q by Activated Protein C," J. Biol. Chem., vol. 270, 1995, pp. 21158-21166.

Heeb, M.J. et al.: "Activated Protein C Resistance: Molecular Mechanisms Based on Studies Using Purified Gln506-factor V," *Blood*, vol. 85, 1995, pp. 3405-3411.

Mann, K.G. et al.: "Activated Protein C Cleavage of Factor Va Leads to dissociation of the A2 Domain," *J. Biol. Chem.*, vol. 272, 1997, pp. 20678-20683.

Guinto, E.R.; Esmon, C.T.: "Loss of Prothrombin and of Factor Xa-Factor Va Interactions Upon Inactivation of Factor Va by Activated Protein C," *J. Biol. Chem.*, vol. 259, 1984, pp. 13986-13992.

Heeb, M.J. et al.: "Binding Sites for Blood Coagulation Factor Xa and Protein S Involving Residues 493-506 in Factor Va.," *Protein Sci.*, vol. 5, 1996, 1883-1889.

International Search Report for related PCT application No. PCT/US02/19017, Jun. 13, 2003 completed search, mailed Jun. 26, 2003.

European Search Report for related European application No. 02737516.1, Apr. 13, 2005 completed search.

* cited by examiner

Factor VIII
   SwissProt Accession # P00451
   Refs

AUTHORS   Wood,W.I., Capon,D.J., Simonsen,C.C., Eaton,D.L., Gitschier,J.,
   Keyt,B., Seeburg,P.H., Smith,D.H., Hollingshead,P., Wion,K.L.,
   Delwart,E., Tuddenham,E.G.D., Vehar,G.A. and Lawn,R.M.
 TITLE   Expression of active human factor VIII from recombinant DNA clones
 JOURNAL   Nature 312 (5992), 330-337 (1984)
 MEDLINE   85061548
 REMARK   SEQUENCE FROM N.A.
REFERENCE   3 (residues 1 to 2351)
 AUTHORS   Toole,J.J., Knopf,J.L., Wozney,J.M., Sultzman,L.A., Buecker,J.L.,
   Pittman,D.D., Kaufman,R.J., Brown,E., Shoemaker,C., Orr,E.C.,
   Amphlett,G.W., Foster,W.B., Coe,M.L., Knutson,G.J., Fass,D.N. and
   Hewick,R.M.
 TITLE   Molecular cloning of a cDNA encoding human antihaemophilic factor
 JOURNAL   Nature 312 (5992), 342-347 (1984)

Note: Numbering in all of these starts with the first aa of the signal peptide as aa 1. The signal peptide is 19 aa long. Standard numbering of the processed protein starts with the first aa of the processed protein as aa 1 (total aa 2332 instead of 2351) Thus in the swissprot file and the references all residues are numbered 19 higher than we number in the processed protein.

Factor V
   SwissProt Accession # P12259
   Ref

REFERENCE   2 (residues 1 to 2224)
 AUTHORS   Jenny,R.J., Pittman,D.D., Toole,J.J., Kriz,R.W., Aldape,R.A.,
   Hewick,R.M., Kaufman,R.J. and Mann,K.G.
 TITLE   Complete cDNA and derived amino acid sequence of human factor V
 JOURNAL   Proc. Natl. Acad. Sci. U.S.A. 84 (14), 4846-4850 (1987)

Same thing applies to the numbering here as in FVIII. The signal peptide is 28 aa long.

Prothrombin
   Swissprot Accession # P00734
   Ref

FIG. 7

REFERENCE 2 (residues 1 to 622)
 AUTHORS   Degen,S.J., MacGillivray,R.T. and Davie,E.W.
 TITLE     Characterization of the complementary deoxyribonucleic acid and
           gene coding for human prothrombin
 JOURNAL   Biochemistry 22 (9), 2087-2097 (1983)

Same thing applies to the numbering here as in FVIII. The signal and propeptide together are 43 aa long and are subtracted from the numbering for the processed polypepeptide

Factor XII

Swissprot Acc # P00748
   Ref

REFERENCE 3 (residues 1 to 615)
 AUTHORS   Cool,D.E., Edgell,C.J., Louie,G.V., Zoller,M.J., Brayer,G.D. and
           MacGillivray,R.T.
 TITLE     Characterization of human blood coagulation factor XII cDNA.
           Prediction of the primary structure of factor XII and the tertiary
           structure of beta-factor XIIa
 JOURNAL   J. Biol. Chem. 260 (25), 13666-13676 (1985)

HGFA

Swissprot Acc# Q04756
   Ref

REFERENCE 1 (residues 1 to 655)
 AUTHORS   Miyazawa,K., Shimomura,T., Kitamura,A., Kondo,J., Morimoto,Y. and
           Kitamura,N.
 TITLE     Molecular cloning and sequence analysis of the cDNA for a human
           serine protease reponsible for activation of hepatocyte growth
           factor. Structural similarity of the protease precursor to blood
           coagulation factor XII
 JOURNAL   J. Biol. Chem. 268 (14), 10024-10028 (1993)

PHBP

PIR Acc# JC4795
   Ref

REFERENCE 1 (residues 1 to 560)
 AUTHORS   Choi-Miura,N.H., Tobe,T., Sumiya,J., Nakano,Y., Sano,Y., Mazda,T.
           and Tomita,M.

FIG. 7A

TITLE  Purification and characterization of a novel hyaluronan-binding
protein (PHBP) from human plasma: it has three EGF, a kringle and a
serine protease domain, similar to hepatocyte growth factor
activator
JOURNAL  J. Biochem. 119 (6), 1157-1165 (1996)

FIG. 7B

NiceProt View of SWISS-PROT: P00451

General information about the entry

| | |
|---|---|
| Entry name | FA8_HUMAN |
| Primary accession number | P00451 |
| Secondary accession numbers | None |
| Entered in SWISS-PROT in | Release 01, July 1986 |
| Sequence was last modified in | Release 01, July 1986 |
| Annotations were last modified in | Release 40, October 2000 |

Name and origin of the protein

| | |
|---|---|
| Protein name | COAGULATION FACTOR VIII [Precursor] |
| Synonyms | PROCOAGULANT COMPONENT<br>ANTIHEMOPHILIC FACTOR<br>AHF |
| Gene name | F8 or F8C |
| From | Homo sapiens (Human) [TaxID: 9606] |
| Taxonomy | Eukaryota; Metazoa; Chordata; Craniata; Vertebrata; Euteleostomi; Mammalia; Eutheria; Primates; Catarrhini; Hominidae; Homo. |

References

[1] SEQUENCE FROM NUCLEIC ACID.
MEDLINE=86081164; PubMed=3935400;
Truett M.A., Blacher R., Burke R.L., Caput D., Chu C., Dina D., Hartog K., Kuo C.H., Masiarz F.R., Merryweather J.P., Najarian R., Pachl C., Potter S.J., Puma J., Quiroga M., Rall L.B., Randolph A., Urdea M.S., Valenzuela P., Dahl H.-H.M., Favalaro J., Hansen J., Nordfang O., Ezban M.;
"Characterization of the polypeptide composition of human factor VIII:C and the nucleotide sequence and expression of the human kidney cDNA.";
DNA 4:333-349(1985).

[2] SEQUENCE FROM NUCLEIC ACID.
MEDLINE=85061548; PubMed=6438526;
Wood W.I., Capon D.J., Simonsen C.C., Eaton D.L., Gitschier J., Keyt B., Seeburg P.H., Smith D.H., Hollingshead P., Wion K.L., Delwart E., Tuddenham E.G.D., Vehar G.A., Lawn R.M.;
"Expression of active human factor VIII from recombinant DNA clones.";
Nature 312:330-337(1984).

[3] SEQUENCE FROM NUCLEIC ACID.
MEDLINE=85061550; PubMed=6438528;
Toole J.J., Knopf J.L., Wozney J.M., Sultzman L.A., Buecker J.L., Pittman D.D., Kaufman R.J., Brown E., Shoemaker C., Orr E.C., Amphlett G.W., Foster W.B., Coe M.L., Knutson G.J., Fass D.N., Hewick R.M.;
"Molecular cloning of a cDNA encoding human antihaemophilic factor.";
Nature 312:342-347(1984).

[4] SEQUENCE FROM NUCLEIC ACID.
MEDLINE=93265012; PubMed=1303178;
Gitschier J., Wood W.I.;
"Sequence of the exon-containing regions of the human factor VIII gene.";
Hum. Mol. Genet. 1:199-200(1992).

[5] SEQUENCE OF 2064-2070 FROM NUCLEIC ACID.
de Water N.S., Williams R., Browett P.J.;
Submitted (JUN-1997) to the EMBL/GenBank/DDBJ databases.

[6] SULFATION OF 1699.
MEDLINE=91093266; PubMed=1898735;
Leyte A., van Schijndel H.B., Niehrs C., Huttner W.B., Verbeet M.P., Mertens K., van Mourik J.A.;
"Sulfation of Tyr1680 of human blood coagulation factor VIII is essential for the interaction of factor VIII with von Willebrand factor.";
J. Biol. Chem. 266:740-746(1991).

FIG. 8

[7] SULFATION.
  MEDLINE=92207952; PubMed=1554716;
  Pittman D.D., Wang J.H., Kaufman R.J.;
  "Identification and functional importance of tyrosine sulfate residues within recombinant factor VIII.";
  Biochemistry 31:3315-3325(1992).
[8] STRUCTURE BY NMR OF 2322-2343.
  MEDLINE=95200924; PubMed=7893714;
  Gilbert G.E., Baleja J.D.;
  "Membrane-binding peptide from the C2 domain of factor VIII forms an amphipathic structure as determined by NMR spectroscopy.";
  Biochemistry 34:3022-3031(1995).
[9] REVIEW ON MOLECULAR BASIS OF HEMOPHILIA A.
  MEDLINE=91221499; PubMed=1902642;
  Gitschier J.;
  "The molecular basis of hemophilia A.";
  Ann. N.Y. Acad. Sci. 614:89-96(1991).
[10] REVIEW ON MOLECULAR BASIS OF HEMOPHILIA A.
  MEDLINE=89088506; PubMed=2491949;
  White G.C. II, Shoemaker C.B.;
  "Factor VIII gene and hemophilia A.";
  Blood 73:1-12(1989).
[11] REVIEW ON MOLECULAR BASIS OF HEMOPHILIA A.
  MEDLINE=95245332; PubMed=7728145;
  Antonarakis S.E., Kazazian H.H., Tuddenham E.G.D.;
  "Molecular etiology of factor VIII deficiency in hemophilia A.";
  Hum. Mutat. 5:1-22(1995).
[12] VARIANT GLN-2326.
  MEDLINE=86235434; PubMed=3012775;
  Gitschier J., Wood W.I., Shuman M.A., Lawn R.M.;
  "Identification of a missense mutation in the factor VIII gene of a mild hemophiliac.";
  Science 232:1415-1416(1986).
[13] VARIANT PRO-2135.
  MEDLINE=88096539; PubMed=3122181;
  Levinson B., Janco R.L., Phillips J.A. III, Gitschier J.;
  "A novel missense mutation in the factor VIII gene identified by analysis of amplified hemophilia DNA sequences.";
  Nucleic Acids Res. 15:9797-9805(1987).
[14] VARIANT GLN-2228.
  MEDLINE=88191889; PubMed=2833855;
  Youssoufian H., Antonarakis S.E., Bell W., Griffin A.M., Kazazian H.H.;
  "Nonsense and missense mutations in hemophilia A: estimate of the relative mutation rate at CG dinucleotides.";
  Am. J. Hum. Genet. 42:718-725(1988).
[15] VARIANT GLY-291.
  MEDLINE=88220354; PubMed=2835904;
  Youssoufian H., Wong C., Aronis S., Platokoukis H., Kazazian H.H. Jr., Antonarakis S.E.;
  "Moderately severe hemophilia A resulting from Glu-->Gly substitution in exon 7 of the factor VIII gene.";
  Am. J. Hum. Genet. 42:867-871(1988).
[16] VARIANT CYS-1708.
  MEDLINE=89274393; PubMed=2499363;
  O'Brien D.P., Tuddenham E.G.;
  "Purification and characterization of factor VIII 1,689-Cys: a nonfunctional cofactor occurring in a patient with severe hemophilia A.";
  Blood 73:2117-2122(1989).
[17] VARIANT CYS-391.
  MEDLINE=90001543; PubMed=2506948;
  Shima M., Ware J., Yoshioka A., Fukui H., Fulcher C.A.;
  "An arginine to cysteine amino acid substitution at a critical thrombin cleavage site in a dysfunctional factor VIII molecule.";
  Blood 74:1612-1617(1989).
[18] VARIANT LEU-189.
  MEDLINE=90057680; PubMed=2510835;
  Chan V., Chan T.K., Tong T.M., Todd D.;

FIG. 8A

"A novel missense mutation in exon 4 of the factor VIII:C gene resulting in moderately severe hemophilia A.";
Blood 74:2688-2691(1989).

[19] VARIANT LEU-2326.
MEDLINE=89197216; PubMed=2495245;
Inaba H., Fujimaki M., Kazazian H.H. Jr., Antonarakis S.E.;
"Mild hemophilia A resulting from Arg-to-Leu substitution in exon 26 of the factor VIII gene.";
Hum. Genet. 81:335-338(1989).

[20] VARIANT HIS-391.
MEDLINE=89264602; PubMed=2498882;
Arai M., Inaba H., Higuchi M., Antonarakis S.E., Kazazian H.H. Jr., Fujimaki M., Hoyer L.W.;
"Direct characterization of factor VIII in plasma: detection of a mutation altering a thrombin cleavage site (arginine-372-->histidine).";
Proc. Natl. Acad. Sci. U.S.A. 86:4277-4281(1989).

[21] VARIANT CYS-1708.
MEDLINE=90105723; PubMed=2104766;
Arai M., Higuchi M., Antonarakis S.E., Kazazian H.H. Jr., Phillips J.A. III, Janco R.L., Hoyer L.W.;
"Characterization of a thrombin cleavage site mutation (Arg 1689 to Cys) in the factor VIII gene of two unrelated patients with cross-reacting material-positive hemophilia A.";
Blood 75:384-389(1990).

[22] VARIANTS GLN-2228 AND LEU-2326.
MEDLINE=90123183; PubMed=2105106;
Casula L., Murru S., Pecorara M., Ristaldi M.S., Restagno G., Mancuso G., Morfini M., de Biasi R., Baudo F., Carbonara A.;
"Recurrent mutations and three novel rearrangements in the factor VIII gene of hemophilia A patients of Italian descent.";
Blood 75:662-670(1990).

[23] VARIANT CYS-391.
MEDLINE=90329422; PubMed=1973901;
Pattinson J.K., McVey J.H., Boon M., Ajani A., Tuddenham E.G.;
"CRM+ haemophilia A due to a missense mutation (372-->Cys) at the internal heavy chain thrombin cleavage site.";
Br. J. Haematol. 75:73-77(1990).

[24] VARIANTS PHE-1699 AND CYS-1708.
MEDLINE=90152691; PubMed=2105906;
Higuchi M., Wong C., Kochhan L., Olek K., Aronis S., Kasper C.K., Kazazian H.H., Antonarakis S.E.;
"Characterization of mutations in the factor VIII gene by direct sequencing of amplified genomic DNA.";
Genomics 6:65-71(1990).

[25] VARIANTS CYS-1728 AND ASP-1941.
MEDLINE=90169988; PubMed=2106480;
Traystman M.D., Higuchi M., Kasper C.K., Antonarakis S.E., Kazazian H.H.;
"Use of denaturing gradient gel electrophoresis to detect point mutations in the factor VIII gene.";
Genomics 6:293-301(1990).

[26] VARIANTS LEU-345 AND ARG-348.
MEDLINE=90192753; PubMed=2107542;
Kogan S., Gitschier J.;
"Mutations and a polymorphism in the factor VIII gene discovered by denaturing gradient gel electrophoresis.";
Proc. Natl. Acad. Sci. U.S.A. 87:2092-2096(1990).

[27] VARIANTS LYS-1723 AND SER-2319.
MEDLINE=91348684; PubMed=1908817;
Paynton C., Sarkar G., Sommer S.S.;
"Identification of mutations in two families with sporadic hemophilia A.";
Hum. Genet. 87:397-400(1991).

[28] VARIANTS.
MEDLINE=91334474; PubMed=1908096;
Higuchi M., Kazazian H.H., Kasch L., Warren T.C., McGinniss M.J., Phillips J.A. III, Kasper C., Janco R., Antonarakis S.E.;
"Molecular characterization of severe hemophilia A suggests that about half the mutations are not within the coding regions and splice junctions of the factor VIII gene.";
Proc. Natl. Acad. Sci. U.S.A. 88:7405-7409(1991).

[29] VARIANTS.

FIG. 8B

MEDLINE=92020842; PubMed=1924291;
Higuchi M., Antonarakis S.E., Kasch L., Oldenburg J., Economou-Petersen E., Olek K., Arai M., Inaba H., Kazazian H.H.;
"Molecular characterization of mild-to-moderate hemophilia A: detection of the mutation in 25 of 29 patients by denaturing gradient gel electrophoresis.";
Proc. Natl. Acad. Sci. U.S.A. 88:8307-8311(1991).

[30] VARIANTS CYS-1708 AND HIS-1708.
MEDLINE=91228147; PubMed=1851341;
Schwaab R., Ludwig M., Kochhan L., Oldenburg J., McVey J.H., Egli H., Brackmann H.H., Olek K.;
"Detection and characterisation of two missense mutations at a cleavage site in the factor VIII light chain.";
Thromb. Res. 61:225-234(1991).

[31] VARIANT GLY-1715.
MEDLINE=92250024; PubMed=1349567;
Reiner A.P., Thompson A.R.;
"Screening for nonsense mutations in patients with severe hemophilia A can provide rapid, direct carrier detection.";
Hum. Genet. 89:88-94(1992).

[32] VARIANT LEU-1960.
MEDLINE=93244837; PubMed=1301194;
Nafa K., Baudis M., Deburgrave N., Bardin J.M., Sultan Y., Kaplan J.C., Delpech M.;
"A novel mutation (Arg-->Leu in exon 18) in factor VIII gene responsible for moderate hemophilia A.";
Hum. Mutat. 1:77-78(1992).

[33] VARIANTS V-89; D-104; V-164; M-181; W-717; F-1808 AND R-2065.
MEDLINE=93250816; PubMed=1301932;
Diamond C., Kogan S., Levinson B., Gitschier J.;
"Amino acid substitutions in conserved domains of factor VIII and related proteins: study of patients with mild and moderately severe hemophilia A.";
Hum. Mutat. 1:248-257(1992).

[34] VARIANTS CYS-1800 AND ILE-2173.
MEDLINE=93250855; PubMed=1301960;
Jonsdottir S., Diamond C., Levinson B., Magnusson S., Jensson O., Gitschier J.;
"Missense mutations causing mild hemophilia A in Iceland detected by denaturing gradient gel electrophoresis.";
Hum. Mutat. 1:506-508(1992).

[35] VARIANTS LEU-308; PHE-577; ALA-653; MET-653 AND PHE-671 DEL.
MEDLINE=93194188; PubMed=8449505;
McGinniss M.J., Kazazian H.H., Hoyer L.W., Bi L., Inaba H., Antonarakis S.E.;
"Spectrum of mutations in CRM-positive and CRM-reduced hemophilia A.";
Genomics 15:392-398(1993).

[36] VARIANTS ILE-299 AND ASN-450.
MEDLINE=93310754; PubMed=8322269;
Pieneman W.C., Reitsma P.H., Briet E.;
"Double strand conformation polymorphism (DSCP) detects two point mutations at codon 280 (AAC-->ATC) and at codon 431 (TAC-->AAC) of the blood coagulation factor VIII gene.";
Thromb. Haemost. 69:473-475(1993).

[37] VARIANTS VAL-129; LYS-631 AND HIS-1800.
MEDLINE=98111374; PubMed=9450898;
Maugard C., Tuffery S., Aguilar-Martinez P., Schved J.-F., Gris J.-C., Demaille J., Claustres M.;
"Protein truncation test: detection of severe haemophilia a mutation and analysis of factor VIII transcripts.";
Hum. Mutat. 11:18-22(1998).

[38] VARIANT HIS-2182.
Theophilus B.D.M., Enayat M.S., Higuchi M., Kazazian H.H., Antonarakis S.E., Hill F.G.H.;
"Independent occurrence of the novel Arg2163 to His mutation in the factor VIII gene in three unrelated families with haemophilia A with different phenotypes.";
Hum. Mutat. 11:334-334(1998).

[39] VARIANTS.
MEDLINE=98264603; PubMed=9603440;
Freson K., Peerlinck K., Aguirre T., Arnout J., Vermylen J., Cassiman J.-J., Matthijs G.;
"Fluorescent chemical cleavage of mismatches for efficient screening of the factor VIII gene.";
Hum. Mutat. 11:470-479(1998).

[40] VARIANTS GLY-550; THR-723; GLY-1894; SER-2107 AND THR-2204.

FIG. 8C

MEDLINE=98112483; PubMed=9452104;
Tavassoli K., Eigel A., Dworniczak B., Valtseva E., Horst J.;
"Identification of four novel mutations in the factor VIII gene: three missense mutations (E1875G, G2088S, I2185T) and a 2-bp deletion (1780delTC).";
Hum. Mutat. Suppl. 1:S260-S262(1998).

[41] VARIANTS.
MEDLINE=99006891; PubMed=9792405;
Tavassoli K., Eigel A., Wilke K., Pollmann H., Horst J.;
"Molecular diagnostics of 15 hemophilia A patients: characterization of eight novel mutations in the factor VIII gene, two of which result in exon skipping.";
Hum. Mutat. 12:301-303(1998).

[42] VARIANTS VAL-439; CYS-1800; HIS-2169; HIS-2182 AND SER-2319.
MEDLINE=99045373; PubMed=9829908;
Laprise S.L., Mak E.K., Killoran K.A., Layman L.C., Gray M.R.;
"Use of denaturing gradient gel blots to screen for point mutations in the factor VIII gene.";
Hum. Mutat. 12:393-402(1998).

[43] VARIANTS ARG-202 AND HIS-301.
MEDLINE=99335269; PubMed=10408784;
Moeller-Morlang K., Tavassoli K., Eigel A., Pollmann H., Horst J.;
"Mutational-screening in the factor VIII gene resulting in the identification of three novel mutations, one of which is a donor splice mutation.";
Hum. Mutat. 13:504-504(1999).

[44] VARIANTS TYR-561; VAL-1869 AND CYS-2344.
MEDLINE=20081067; PubMed=10612839;
Akkarapatumwong V., Oranwiroon S., Pung-amritt P., Treesucon A., Thanootarakul P., Veerakul G., Mahasandana C., Panyim S., Yenchitsomanus P.;
"Mutations of the factor VIII gene in Thai hemophilia A patients.";
Hum. Mutat. 15:117-118(2000).

Comments

- *FUNCTION*: FACTOR VIII, ALONG WITH CALCIUM AND PHOSPHOLIPID, ACTS AS A COFACTOR FOR FACTOR IXA WHEN IT CONVERTS FACTOR X TO THE ACTIVATED FORM, FACTOR XA.
- *SUBCELLULAR LOCATION*: EXTRACELLULAR.
- *DOMAIN*: DOMAIN F5/8 TYPE C 2 IS RESPONSIBLE FOR PHOSPHOLIPID-BINDING AND ESSENTIAL FOR FACTOR VIII ACTIVITY.
- *DISEASE*: HEMOPHILIA A IS A COMMON RECESSIVE X-LINKED COAGULATION DISORDER DUE TO DEFECTS IN F8C. THE FREQUENCY OF HEMOPHILIA A IS 1-2 IN 10,000 MALE BIRTHS IN ALL ETHNIC GROUPS. ABOUT 50% OF PATIENTS HAVE SEVERE HEMOPHILIA A WITH F8C ACTIVITY LESS THAN 1% OF NORMAL: THEY HAVE FREQUENT SPONTANEOUS BLEEDING INTO JOINTS, MUSCLES AND INTERNAL ORGANS. MODERATELY SEVERE HEMOPHILIA A OCCURS IN ABOUT 10% OF PATIENTS; F8C ACTIVITY IS 2-5% OF NORMAL, AND THERE IS BLEEDING AFTER MINOR TRAUMA. MILD HEMOPHILIA A, WHICH OCCURS IN 30-40% OF PATIENTS, IS ASSOCIATED WITH F8C ACTIVITY OF 5-30% AND BLEEDING OCCURS ONLY AFTER SIGNIFICANT TRAUMA OR SURGERY. OF PARTICULAR INTEREST FOR THE UNDERSTANDING OF THE FUNCTION OF F8C IS THE CATEGORY OF CRM (CROSS-REACTING MATERIAL) POSITIVE PATIENTS (APPROXIMATELY 5%) THAT HAVE CONSIDERABLE AMOUNT OF F8C IN THEIR PLASMA (AT LEAST 30% OF NORMAL), BUT THE PROTEIN IS NONFUNCTIONAL; I.E., THE F8C ACTIVITY IS MUCH LESS THAN THE PLASMA PROTEIN LEVEL. CRM-REDUCED IS ANOTHER CATEGORY OF PATIENTS IN WHICH THE F8C ANTIGEN AND ACTIVITY ARE REDUCED TO APPROXIMATELY THE SAME LEVEL. MOST MUTATIONS ARE CRM NEGATIVE, AND PROBABLY AFFECT THE FOLDING AND STABILITY OF THE PROTEIN.
- *PHARMACEUTICAL*: AVAILABLE UNDER THE NAMES KOGENATE (BAYER) AND RECOMBINATE (BAXTER AND AMERICAN HOME PRODUCTS). USED TO TREAT HEMOPHILIA A.
- *SIMILARITY*: CONTAINS 3 F5/8 TYPE A DOMAINS: EACH IS COMPOSED OF 2 PLASTOCYANIN-LIKE REPEATS.
- *SIMILARITY*: CONTAINS 2 F5/8 TYPE C DOMAINS.
- *SIMILARITY*: STRONG, TO COAGULATION FACTOR V.
- *DATABASE*: NAME=HAMSters; NOTE=Factor VIII mutation db; WWW="http://europium.mrc.rpms.ac.uk/".

FIG. 8D

Copyright

This SWISS-PROT entry is copyright. It is produced through a collaboration between the Swiss Institute of Bioinformatics and the EMBL outstation - the European Bioinformatics Institute. There are no restrictions on its use by non-profit institutions as long as its content is in no way modified and this statement is not removed. Usage by and for commercial entities requires a license agreement (See http://www.isb-sib.ch/announce/ or send an email to license@isb-sib.ch)

Cross-references

| | |
|---|---|
| EMBL | M14113; AAA52485.1; -. |
| | X01179; CAA25619.1; -. |
| | K01740; AAA52484.1; -. |
| | M88648; AAA52420.1; -. |
| | M88628; AAA52420.1; JOINED. |
| | M88629; AAA52420.1; JOINED. |
| | M88630; AAA52420.1; JOINED. |
| | M88631; AAA52420.1; JOINED. |
| | M88632; AAA52420.1; JOINED. |
| | M88633; AAA52420.1; JOINED. |
| | M88634; AAA52420.1; JOINED. |
| | M88635; AAA52420.1; JOINED. |
| | M88636; AAA52420.1; JOINED. |
| | M88638; AAA52420.1; JOINED. |
| | M88639; AAA52420.1; JOINED. |
| | M88640; AAA52420.1; JOINED. |
| | M88641; AAA52420.1; JOINED. |
| | M88642; AAA52420.1; JOINED. |
| | M88643; AAA52420.1; JOINED. |
| | M88644; AAA52420.1; JOINED. |
| | M88645; AAA52420.1; JOINED. |
| | M88646; AAA52420.1; JOINED. |
| | M88647; AAA52420.1; JOINED. |
| | U80228; AAB61261.1; -. |
| PIR | A00525; EZHU. |
| | A23584; A23584. |
| PDB | 1CFG; 02-NOV-95. |
| | 1FAC; 11-JAN-97. |
| GlycoSuiteDB | P00451; -. |
| MIM | 134430. |
| | 134500. |
| | 134510. |
| | 227310. |
| | 306700. |
| GeneCards | F8. |
| InterPro | IPR001117; Cu-oxidase. |
| | IPR000421; FA58_C. |
| Pfam | PF00394; Cu-oxidase; 3. |
| | PF00754; F5_F8_type_C; 2. |
| SMART | SM00231; FA58C; 2. |
| PROSITE | PS00079; MULTICOPPER_OXIDASE1; 3. |
| | PS01285; FA58C_1; 2. |
| | PS01286; FA58C_2; 2. |
| Implicit links to | ProDom; BLOCKS; DOMO; ProtoMap; PRESAGE; DIP; SWISS-2DPAGE. |

Keywords

Blood coagulation; Repeat; Plasma; Acute phase; Calcium; Hemophilia; Signal; Glycoprotein; Sulfation; Disease mutation; Polymorphism; Pharmaceutical; 3D-structure.

FIG. 8E

Features

| Key | From | To | Length | Description |
|---|---|---|---|---|
| SIGNAL | 1 | 19 | 19 | |
| CHAIN | 20 | 2351 | 2332 | COAGULATION FACTOR VIII. |
| CHAIN | 20 | 1332 | 1313 | FACTOR VIIIA HEAVY CHAIN (200 KDA). |
| CHAIN | 20 | 759 | 740 | FACTOR VIIIA HEAVY CHAIN (92 KDA). |
| CHAIN | 760 | 1332 | 573 | B. |
| CHAIN | 1668 | 2351 | 684 | FACTOR VIIIA LIGHT CHAIN (80 KDA). |
| DOMAIN | 20 | 348 | 329 | F5/8 TYPE A 1. |
| DOMAIN | 20 | 198 | 179 | PLASTOCYANIN-LIKE 1. |
| DOMAIN | 206 | 348 | 143 | PLASTOCYANIN-LIKE 2. |
| DOMAIN | 399 | 730 | 332 | F5/8 TYPE A 2. |
| DOMAIN | 399 | 573 | 175 | PLASTOCYANIN-LIKE 3. |
| DOMAIN | 583 | 730 | 148 | PLASTOCYANIN-LIKE 4. |
| DOMAIN | 760 | 1667 | 908 | B. |
| DOMAIN | 1713 | 2040 | 328 | F5/8 TYPE A 3. |
| DOMAIN | 1713 | 1877 | 165 | PLASTOCYANIN-LIKE 5. |
| DOMAIN | 1887 | 2040 | 154 | PLASTOCYANIN-LIKE 6. |
| DOMAIN | 2040 | 2188 | 149 | F5/8 TYPE C 1. |
| DOMAIN | 2193 | 2345 | 153 | F5/8 TYPE C 2. |
| SITE | 1332 | 1333 | 2 | CLEAVAGE (ACTIVATION). |
| SITE | 1667 | 1668 | 2 | CLEAVAGE (ACTIVATION). |
| SITE | 391 | 392 | 2 | CLEAVAGE (BY THROMBIN). |
| SITE | 759 | 760 | 2 | CLEAVAGE (BY THROMBIN). |
| SITE | 1708 | 1709 | 2 | CLEAVAGE (BY THROMBIN). |
| MOD_RES | 365 | 365 | | SULFATION. |
| MOD_RES | 737 | 737 | | SULFATION (PROBABLE). |
| MOD_RES | 738 | 738 | | SULFATION (PROBABLE). |
| MOD_RES | 742 | 742 | | SULFATION (PROBABLE). |
| MOD_RES | 1683 | 1683 | | SULFATION. |
| MOD_RES | 1699 | 1699 | | SULFATION. |
| DISULFID | 172 | 198 | | PROBABLE. |
| DISULFID | 547 | 573 | | PROBABLE. |
| DISULFID | 1851 | 1877 | | PROBABLE. |
| DISULFID | 2040 | 2188 | | BY SIMILARITY. |
| DISULFID | 2193 | 2345 | | BY SIMILARITY. |
| CARBOHYD | 60 | 60 | | N-LINKED (GLCNAC...) (POTENTIAL). |
| CARBOHYD | 258 | 258 | | N-LINKED (GLCNAC...) (POTENTIAL). |
| CARBOHYD | 601 | 601 | | N-LINKED (GLCNAC...) (POTENTIAL). |
| CARBOHYD | 776 | 776 | | N-LINKED (GLCNAC...) (POTENTIAL). |
| CARBOHYD | 803 | 803 | | N-LINKED (GLCNAC...) (POTENTIAL). |
| CARBOHYD | 847 | 847 | | N-LINKED (GLCNAC...) (POTENTIAL). |
| CARBOHYD | 919 | 919 | | N-LINKED (GLCNAC...) (POTENTIAL). |
| CARBOHYD | 962 | 962 | | N-LINKED (GLCNAC...) (POTENTIAL). |
| CARBOHYD | 982 | 982 | | N-LINKED (GLCNAC...) (POTENTIAL). |
| CARBOHYD | 1020 | 1020 | | N-LINKED (GLCNAC...) (POTENTIAL). |
| CARBOHYD | 1024 | 1024 | | N-LINKED (GLCNAC...) (POTENTIAL). |
| CARBOHYD | 1074 | 1074 | | N-LINKED (GLCNAC...) (POTENTIAL). |
| CARBOHYD | 1085 | 1085 | | N-LINKED (GLCNAC...) (POTENTIAL). |
| CARBOHYD | 1204 | 1204 | | N-LINKED (GLCNAC...) (POTENTIAL). |
| CARBOHYD | 1274 | 1274 | | N-LINKED (GLCNAC...) (POTENTIAL). |
| CARBOHYD | 1278 | 1278 | | N-LINKED (GLCNAC...) (POTENTIAL). |
| CARBOHYD | 1301 | 1301 | | N-LINKED (GLCNAC...) (POTENTIAL). |
| CARBOHYD | 1319 | 1319 | | N-LINKED (GLCNAC...) (POTENTIAL). |
| CARBOHYD | 1431 | 1431 | | N-LINKED (GLCNAC...) (POTENTIAL). |
| CARBOHYD | 1461 | 1461 | | N-LINKED (GLCNAC...) (POTENTIAL). |
| CARBOHYD | 1829 | 1829 | | N-LINKED (GLCNAC...) (POTENTIAL). |
| CARBOHYD | 2137 | 2137 | | N-LINKED (GLCNAC...) (POTENTIAL). |

FIG. 8F

| | | | |
|---|---|---|---|
| VARIANT | 26 | 26 | L -> R (SEVERE HEMOPHILIA). /FTId=VAR_001045. |
| VARIANT | 30 | 30 | E -> V (MILD HEMOPHILIA). /FTId=VAR_001046. |
| VARIANT | 41 | 41 | G -> C (SEVERE/MODERATE HEMOPHILIA). /FTId=VAR_001047. |
| VARIANT | 48 | 48 | R -> C (SEVERE HEMOPHILIA). /FTId=VAR_001048. |
| VARIANT | 75 | 75 | D -> V. /FTId=VAR_001049. |
| VARIANT | 89 | 89 | G -> D (SEVERE HEMOPHILIA). /FTId=VAR_001050. |
| VARIANT | 89 | 89 | G -> V (MILD HEMOPHILIA). /FTId=VAR_001051. |
| VARIANT | 99 | 99 | V -> D (SEVERE HEMOPHILIA). /FTId=VAR_001052. |
| VARIANT | 104 | 104 | V -> D (MILD HEMOPHILIA). /FTId=VAR_001053. |
| VARIANT | 108 | 108 | K -> T (MILD HEMOPHILIA). /FTId=VAR_001054. |
| VARIANT | 110 | 110 | M -> V (MODERATE HEMOPHILIA). /FTId=VAR_001055. |
| VARIANT | 117 | 117 | L -> R (SEVERE HEMOPHILIA). /FTId=VAR_001056. |
| VARIANT | 129 | 129 | E -> V (SEVERE HEMOPHILIA). /FTId=VAR_001057. |
| VARIANT | 130 | 130 | G -> R (SEVERE HEMOPHILIA). /FTId=VAR_001058. |
| VARIANT | 132 | 132 | E -> D (SEVERE HEMOPHILIA). /FTId=VAR_001059. |
| VARIANT | 133 | 133 | Y -> C (MILD HEMOPHILIA). /FTId=VAR_001060. |
| VARIANT | 135 | 135 | D -> G (SEVERE HEMOPHILIA). /FTId=VAR_001061. |
| VARIANT | 137 | 137 | T -> I (MODERATE HEMOPHILIA). /FTId=VAR_001062. |
| VARIANT | 164 | 164 | G -> V (MILD HEMOPHILIA). /FTId=VAR_001063. |
| VARIANT | 165 | 165 | P -> S (SEVERE HEMOPHILIA). /FTId=VAR_001064. |
| VARIANT | 181 | 181 | V -> M (MODERATE HEMOPHILIA). /FTId=VAR_001065. |
| VARIANT | 185 | 185 | K -> T (MILD HEMOPHILIA). /FTId=VAR_001066. |
| VARIANT | 189 | 189 | S -> L (MODERATE HEMOPHILIA). /FTId=VAR_001067. |
| VARIANT | 202 | 202 | S -> R (MILD HEMOPHILIA). /FTId=VAR_008123. |
| VARIANT | 222 | 222 | D -> V (MODERATE HEMOPHILIA). /FTId=VAR_001068. |
| VARIANT | 224 | 224 | G -> W (MODERATE HEMOPHILIA). /FTId=VAR_001069. |
| VARIANT | 253 | 253 | V -> F (SEVERE HEMOPHILIA). /FTId=VAR_001070. |
| VARIANT | 266 | 266 | G -> Q (SEVERE HEMOPHILIA). /FTId=VAR_001071. |
| VARIANT | 278 | 278 | G -> R (SEVERE HEMOPHILIA). /FTId=VAR_001072. |
| VARIANT | 285 | 285 | V -> G (MILD HEMOPHILIA). /FTId=VAR_001073. |
| VARIANT | 291 | 291 | E -> G (MODERATE/MILD HEMOPHILIA). /FTId=VAR_001074. |
| VARIANT | 294 | 294 | T -> I (MODERATE HEMOPHILIA). /FTId=VAR_001075. |
| VARIANT | 299 | 299 | N -> I (MILD HEMOPHILIA). /FTId=VAR_001076. |
| VARIANT | 301 | 301 | R -> H (SEVERE HEMOPHILIA). /FTId=VAR_001077. |
| VARIANT | 301 | 301 | R -> L (SEVERE HEMOPHILIA). /FTId=VAR_001078. |
| VARIANT | 308 | 308 | S -> L (MODERATE HEMOPHILIA). /FTId=VAR_001079. |
| VARIANT | 312 | 312 | F -> S (MODERATE HEMOPHILIA). /FTId=VAR_001080. |
| VARIANT | 314 | 314 | T -> A (MILD HEMOPHILIA). /FTId=VAR_001081. |
| VARIANT | 314 | 314 | T -> I (MODERATE HEMOPHILIA). /FTId=VAR_001082. |
| VARIANT | 327 | 327 | L -> P (SEVERE HEMOPHILIA). /FTId=VAR_001083. |

FIG. 8G

| | | | |
|---|---|---|---|
| VARIANT | 331 | 331 | I -> V (MILD HEMOPHILIA). /FTId=VAR_001084. |
| VARIANT | 345 | 345 | V -> L (SEVERE HEMOPHILIA). /FTId=VAR_001085. |
| VARIANT | 348 | 348 | C -> R (SEVERE HEMOPHILIA). /FTId=VAR_001086. |
| VARIANT | 348 | 348 | C -> S (MODERATE HEMOPHILIA). /FTId=VAR_001087. |
| VARIANT | 348 | 348 | C -> Y (SEVERE HEMOPHILIA). /FTId=VAR_001088. |
| VARIANT | 391 | 391 | R -> C (OKAYAMA; MODERATE HEMOPHILIA; ABOLISHES THE NORMAL CLEAVAGE BY THROMBIN). /FTId=VAR_001089. |
| VARIANT | 391 | 391 | R -> H (KUMAMOTO; MODERATE/MILD HEMOPHILIA; ABOLISHES THE NORMAL CLEAVAGE BY THROMBIN). /FTId=VAR_001090. |
| VARIANT | 391 | 391 | R -> P (SEVERE HEMOPHILIA; ABOLISHES THE NORMAL CLEAVAGE BY THROMBIN). /FTId=VAR_001091. |
| VARIANT | 392 | 392 | S -> L (MILD HEMOPHILIA; ABOLISHES NORMAL CLEAVAGE BY THROMBIN). /FTId=VAR_001092. |
| VARIANT | 392 | 392 | S -> P (MILD HEMOPHILIA). /FTId=VAR_001093. |
| VARIANT | 405 | 405 | I -> S (SEVERE HEMOPHILIA). /FTId=VAR_001094. |
| VARIANT | 409 | 409 | E -> G (SEVERE/MODERATE HEMOPHILIA). /FTId=VAR_001095. |
| VARIANT | 431 | 431 | L -> F (MODERATE/MILD HEMOPHILIA). /FTId=VAR_001096. |
| VARIANT | 439 | 439 | G -> V (SEVERE HEMOPHILIA). /FTId=VAR_001097. |
| VARIANT | 444 | 444 | K -> R (SEVERE HEMOPHILIA). /FTId=VAR_001098. |
| VARIANT | 450 | 450 | Y -> N (MODERATE HEMOPHILIA). /FTId=VAR_001099. |
| VARIANT | 474 | 474 | G -> R (SEVERE HEMOPHILIA). /FTId=VAR_001100. |
| VARIANT | 488 | 488 | A -> G (MODERATE HEMOPHILIA). /FTId=VAR_001101. |
| VARIANT | 492 | 492 | Y -> H (MILD HEMOPHILIA). /FTId=VAR_001102. |
| VARIANT | 492 | 492 | Y -> C (MODERATE HEMOPHILIA). /FTId=VAR_001103. |
| VARIANT | 494 | 494 | I -> T (MILD HEMOPHILIA). /FTId=VAR_001104. |
| VARIANT | 498 | 498 | G -> R (SEVERE/MODERATE HEMOPHILIA). /FTId=VAR_001105. |
| VARIANT | 544 | 544 | D -> N (MODERATE HEMOPHILIA). /FTId=VAR_001106. |
| VARIANT | 546 | 546 | R -> W (MILD HEMOPHILIA). /FTId=VAR_001107. |
| VARIANT | 550 | 550 | R -> C (MODERATE/MILD HEMOPHILIA). /FTId=VAR_001108. |
| VARIANT | 550 | 550 | R -> G (MILD HEMOPHILIA). /FTId=VAR_001109. |
| VARIANT | 550 | 550 | R -> H (MILD HEMOPHILIA). /FTId=VAR_001110. |
| VARIANT | 554 | 554 | S -> G (MILD HEMOPHILIA). /FTId=VAR_001111. |
| VARIANT | 556 | 556 | V -> D (MODERATE HEMOPHILIA). /FTId=VAR_001112. |
| VARIANT | 561 | 561 | D -> Y (IN SEVERE HEMOPHILIA). /FTId=VAR_008967. |
| VARIANT | 577 | 577 | S -> F (MILD HEMOPHILIA). /FTId=VAR_001113. |
| VARIANT | 584 | 584 | Q -> K (MODERATE/MILD HEMOPHILIA). /FTId=VAR_001114. |
| VARIANT | 585 | 585 | I -> T (SEVERE/MODERATE HEMOPHILIA). /FTId=VAR_001115. |
| VARIANT | 596 | 596 | S -> P (SEVERE HEMOPHILIA). /FTId=VAR_001116. |
| VARIANT | 603 | 603 | S -> I (HEMOPHILIA). /FTId=VAR_001117. |
| VARIANT | 604 | 604 | W -> C (SEVERE HEMOPHILIA). /FTId=VAR_001118. |
| VARIANT | 605 | 605 | Y -> S (SEVERE HEMOPHILIA). /FTId=VAR_001119. |
| VARIANT | 612 | 612 | R -> C (MILD/MODERATE HEMOPHILIA). /FTId=VAR_001120. |

FIG. 8H

| | | | |
|---|---|---|---|
| VARIANT | 631 | 631 | N -> K (SEVERE HEMOPHILIA).<br>/FTId=VAR_001121. |
| VARIANT | 631 | 631 | N -> S (HEMOPHILIA).<br>/FTId=VAR_001122. |
| VARIANT | 644 | 644 | L -> V (MILD HEMOPHILIA).<br>/FTId=VAR_001123. |
| VARIANT | 653 | 653 | V -> A (MILD HEMOPHILIA).<br>/FTId=VAR_001124. |
| VARIANT | 653 | 653 | V -> M (SEVERE HEMOPHILIA).<br>/FTId=VAR_001125. |
| VARIANT | 663 | 663 | A -> V (MILD HEMOPHILIA).<br>/FTId=VAR_001126. |
| VARIANT | 671 | 671 | MISSING (SEVERE HEMOPHILIA).<br>/FTId=VAR_001127. |
| VARIANT | 677 | 677 | F -> L (MODERATE HEMOPHILIA).<br>/FTId=VAR_001128. |
| VARIANT | 699 | 699 | M -> V (SEVERE HEMOPHILIA).<br>/FTId=VAR_001129. |
| VARIANT | 717 | 717 | R -> W (MILD HEMOPHILIA).<br>/FTId=VAR_001130. |
| VARIANT | 720 | 720 | G -> D (SEVERE/MODERATE HEMOPHILIA).<br>/FTId=VAR_001131. |
| VARIANT | 723 | 723 | A -> T (MILD/MODERATE HEMOPHILIA).<br>/FTId=VAR_001132. |
| VARIANT | 727 | 727 | V -> F (SEVERE HEMOPHILIA).<br>/FTId=VAR_001133. |
| VARIANT | 739 | 739 | E -> K (MILD HEMOPHILIA).<br>/FTId=VAR_001134. |
| VARIANT | 1057 | 1057 | E -> K (MODERATE HEMOPHILIA).<br>/FTId=VAR_001135. |
| VARIANT | 1260 | 1260 | D -> E.<br>/FTId=VAR_001136. |
| VARIANT | 1481 | 1481 | L -> P.<br>/FTId=VAR_001137. |
| VARIANT | 1699 | 1699 | Y -> C (SEVERE HEMOPHILIA).<br>/FTId=VAR_001138. |
| VARIANT | 1699 | 1699 | Y -> F (MILD/MODERATE HEMOPHILIA).<br>/FTId=VAR_001139. |
| VARIANT | 1708 | 1708 | R -> C (EAST HARTFORD; SEVERE/MODERATE HEMOPHILIA; ABOLISHES THROMBIN CLEAVAGE AT THE LIGHT CHAIN).<br>/FTId=VAR_001140. |
| VARIANT | 1708 | 1708 | R -> H (MILD HEMOPHILIA; ABOLISHES THROMBIN CLEAVAGE AT THE LIGHT CHAIN).<br>/FTId=VAR_001141. |
| VARIANT | 1715 | 1715 | R -> G (MILD HEMOPHILIA).<br>/FTId=VAR_001142. |
| VARIANT | 1723 | 1723 | E -> K (SEVERE HEMOPHILIA).<br>/FTId=VAR_001143. |
| VARIANT | 1728 | 1728 | Y -> C (MODERATE HEMOPHILIA).<br>/FTId=VAR_001144. |
| VARIANT | 1769 | 1769 | G -> R (MILD HEMOPHILIA).<br>/FTId=VAR_001145. |
| VARIANT | 1775 | 1775 | L -> V (MODERATE HEMOPHILIA).<br>/FTId=VAR_001146. |
| VARIANT | 1775 | 1775 | L -> F (MILD HEMOPHILIA).<br>/FTId=VAR_001147. |
| VARIANT | 1779 | 1779 | G -> E (SEVERE HEMOPHILIA).<br>/FTId=VAR_001148. |
| VARIANT | 1791 | 1791 | M -> T (SEVERE HEMOPHILIA).<br>/FTId=VAR_001149. |
| VARIANT | 1800 | 1800 | R -> H (MODERATE HEMOPHILIA).<br>/FTId=VAR_001150. |
| VARIANT | 1800 | 1800 | R -> C (MILD HEMOPHILIA).<br>/FTId=VAR_001151. |
| VARIANT | 1800 | 1800 | R -> G (MILD HEMOPHILIA).<br>/FTId=VAR_001152. |
| VARIANT | 1803 | 1803 | S -> Y (SEVERE HEMOPHILIA).<br>/FTId=VAR_001153. |
| VARIANT | 1808 | 1808 | L -> F (MILD HEMOPHILIA).<br>/FTId=VAR_001154. |
| VARIANT | 1842 | 1842 | M -> I (MODERATE HEMOPHILIA).<br>/FTId=VAR_001155. |
| VARIANT | 1844 | 1844 | P -> S (MILD HEMOPHILIA).<br>/FTId=VAR_001156. |
| VARIANT | 1845 | 1845 | T -> P (MILD HEMOPHILIA).<br>/FTId=VAR_001157. |
| VARIANT | 1853 | 1853 | A -> T (SEVERE HEMOPHILIA).<br>/FTId=VAR_001158. |
| VARIANT | 1853 | 1853 | A -> V (MILD HEMOPHILIA).<br>/FTId=VAR_001159. |

FIG. 8I

| | | | |
|---|---|---|---|
| VARIANT | 1865 | 1865 | D -> N (SEVERE HEMOPHILIA).<br>/FTId=VAR_001160. |
| VARIANT | 1865 | 1865 | D -> Y (SEVERE HEMOPHILIA).<br>/FTId=VAR_001161. |
| VARIANT | 1867 | 1867 | H -> R (MODERATE HEMOPHILIA).<br>/FTId=VAR_001162. |
| VARIANT | 1869 | 1869 | G -> V (SEVERE HEMOPHILIA).<br>/FTId=VAR_001163. |
| VARIANT | 1873 | 1873 | P -> R (SEVERE HEMOPHILIA).<br>/FTId=VAR_001164. |
| VARIANT | 1888 | 1888 | R -> I (SEVERE HEMOPHILIA).<br>/FTId=VAR_001165. |
| VARIANT | 1894 | 1894 | E -> G (MODERATE HEMOPHILIA).<br>/FTId=VAR_001166. |
| VARIANT | 1904 | 1904 | E -> K (SEVERE HEMOPHILIA).<br>/FTId=VAR_001167. |
| VARIANT | 1941 | 1941 | N -> D (SEVERE/MODERATE HEMOPHILIA).<br>/FTId=VAR_001168. |
| VARIANT | 1941 | 1941 | N -> S (SEVERE/MODERATE HEMOPHILIA).<br>/FTId=VAR_001169. |
| VARIANT | 1960 | 1960 | R -> Q (MILD/MODERATE HEMOPHILIA).<br>/FTId=VAR_001170. |
| VARIANT | 1960 | 1960 | R -> L (MODERATE HEMOPHILIA).<br>/FTId=VAR_001171. |
| VARIANT | 1967 | 1967 | G -> D (MODERATE HEMOPHILIA).<br>/FTId=VAR_001172. |
| VARIANT | 1979 | 1979 | G -> V (MODERATE HEMOPHILIA).<br>/FTId=VAR_001173. |
| VARIANT | 1980 | 1980 | H -> Y (MILD HEMOPHILIA).<br>/FTId=VAR_001174. |
| VARIANT | 2016 | 2016 | R -> W (MODERATE/SEVERE HEMOPHILIA).<br>/FTId=VAR_001175. |
| VARIANT | 2038 | 2038 | N -> S (MODERATE HEMOPHILIA).<br>/FTId=VAR_001176. |
| VARIANT | 2065 | 2065 | W -> R (MODERATE HEMOPHILIA).<br>/FTId=VAR_001177. |
| VARIANT | 2088 | 2088 | S -> F (SEVERE HEMOPHILIA).<br>/FTId=VAR_001178. |
| VARIANT | 2093 | 2093 | D -> G (MILD HEMOPHILIA).<br>/FTId=VAR_001179. |
| VARIANT | 2105 | 2105 | T -> N (MODERATE HEMOPHILIA).<br>/FTId=VAR_001180. |
| VARIANT | 2107 | 2107 | G -> S (SEVERE HEMOPHILIA).<br>/FTId=VAR_001181. |
| VARIANT | 2120 | 2120 | F -> L (MILD HEMOPHILIA).<br>/FTId=VAR_001182. |
| VARIANT | 2124 | 2124 | Y -> C (MILD HEMOPHILIA).<br>/FTId=VAR_001183. |
| VARIANT | 2135 | 2135 | R -> P (SEVERE HEMOPHILIA).<br>/FTId=VAR_001184. |
| VARIANT | 2138 | 2138 | S -> Y (MILD/MODERATE HEMOPHILIA).<br>/FTId=VAR_001185. |
| VARIANT | 2148 | 2148 | N -> S (MODERATE HEMOPHILIA).<br>/FTId=VAR_001186. |
| VARIANT | 2169 | 2169 | R -> H (SEVERE/MILD HEMOPHILIA).<br>/FTId=VAR_001187. |
| VARIANT | 2172 | 2172 | P -> Q (MODERATE HEMOPHILIA).<br>/FTId=VAR_001188. |
| VARIANT | 2173 | 2173 | T -> I (MILD HEMOPHILIA).<br>/FTId=VAR_001189. |
| VARIANT | 2178 | 2178 | R -> C (MILD HEMOPHILIA).<br>/FTId=VAR_001190. |
| VARIANT | 2178 | 2178 | R -> H (MILD HEMOPHILIA).<br>/FTId=VAR_001191. |
| VARIANT | 2178 | 2178 | R -> L (MILD HEMOPHILIA).<br>/FTId=VAR_001192. |
| VARIANT | 2182 | 2182 | R -> C (MODERATE HEMOPHILIA).<br>/FTId=VAR_001193. |
| VARIANT | 2182 | 2182 | R -> H (MODERATE/SEVERE HEMOPHILIA).<br>/FTId=VAR_001194. |
| VARIANT | 2183 | 2183 | M -> V (MILD HEMOPHILIA).<br>/FTId=VAR_001195. |
| VARIANT | 2185 | 2185 | L -> S (SEVERE HEMOPHILIA).<br>/FTId=VAR_001196. |
| VARIANT | 2204 | 2204 | I -> T (MILD HEMOPHILIA).<br>/FTId=VAR_001197. |
| VARIANT | 2209 | 2209 | I -> N (MODERATE HEMOPHILIA).<br>/FTId=VAR_001198. |
| VARIANT | 2211 | 2211 | A -> P (MODERATE HEMOPHILIA).<br>/FTId=VAR_001199. |

FIG. 8J

```
VARIANT      2223   2223    MISSING (SEVERE/MODERATE HEMOPHILIA).
                            /FTId=VAR_001200.
VARIANT      2228   2228    R -> G (SEVERE HEMOPHILIA).
                            /FTId=VAR_001201.
VARIANT      2228   2228    R -> L (MODERATE HEMOPHILIA).
                            /FTId=VAR_001202.
VARIANT      2228   2228    R -> Q (SEVERE/MODERATE HEMOPHILIA).
                            /FTId=VAR_001203.
VARIANT      2242   2242    V -> M.
                            /FTId=VAR_001204.
VARIANT      2248   2248    W -> C (MODERATE HEMOPHILIA).
                            /FTId=VAR_001205.
VARIANT      2265   2265    Q -> R (MODERATE HEMOPHILIA).
                            /FTId=VAR_001206.
VARIANT      2319   2319    P -> L (MILD/SEVERE HEMOPHILIA).
                            /FTId=VAR_001207.
VARIANT      2319   2319    P -> S (MILD HEMOPHILIA).
                            /FTId=VAR_001208.
VARIANT      2323   2323    R -> C (SEVERE HEMOPHILIA; MAY CAUSE REDUCED
                            PHOSPHOLIPID BINDING).
                            /FTId=VAR_001209.
VARIANT      2323   2323    R -> H (MILD HEMOPHILIA; MAY CAUSE REDUCED
                            PHOSPHOLIPID BINDING).
                            /FTId=VAR_001210.
VARIANT      2326   2326    R -> L (SEVERE/MODERATE HEMOPHILIA; MAY CAUSE
                            REDUCED PHOSPHOLIPID BINDING).
                            /FTId=VAR_001211.
VARIANT      2326   2326    R -> Q (MILD/MODERATE HEMOPHILIA; MAY CAUSE
                            REDUCED PHOSPHOLIPID BINDING).
                            /FTId=VAR_001212.
VARIANT      2344   2344    G -> C (MODERATE HEMOPHILIA).
                            /FTId=VAR_008968.
CONFLICT     768    768     P -> R (IN REF. 2).
CONFLICT     1922   1922    C -> S (IN REF. 4).
```

Sequence information

Length: 2351 AA [This is the length of the unprocessed precursor]
Molecular weight: 267007 Da [This is the MW of the unprocessed precursor]
CRC64: 75FB6A2955C74CB0 [This is a checksum on the sequence]

```
            10         20         30         40         50         60
            |          |          |          |          |          |
     MQIELSTCFF LCLLRFCFSA TRRYYLGAVE LSWDYMQSDL GELPVDARFP PRVPKSFPFN 70         80         90        100        110        120
            |          |          |          |          |          |
     TSVVYKKTLF VEFTDHLFNI AKPRPPWMGL LGPTIQAEVY DTVVITLKNM ASHPVSLHAV 130        140        150        160        170        180
            |          |          |          |          |          |
     GVSYWKASEG AEYDDQTSQR EKEDDKVFPG GSHTYVWQVL KENGPMASDP LCLTYSYLSH 190        200        210        220        230        240
            |          |          |          |          |          |
     VDLVKDLNSG LIGALLVCRE GSLAKEKTQT LHKFILLFAV FDEGKSWHSE TKNSLMQDRD 250        260        270        280        290        300
            |          |          |          |          |          |
     AASARAWPKM HTVNGYVNRS LPGLIGCHRK SVYWHVIGMG TTPEVHSIFL EGHTFLVRNH 310        320        330        340        350        360
            |          |          |          |          |          |
     RQASLEISPI TFLTAQTLLM DLGQFLLFCH ISSHQHDGME AYVKVDSCPE EPQLRMKNNE 370        380        390        400        410        420
            |          |          |          |          |          |
     EAEDYDDDLT DSEMDVVRFD DDNSPSFIQI RSVAKKHPKT WVHYIAAEEE DWDYAPLVLA 430        440        450        460        470        480
            |          |          |          |          |          |
     PDDRSYKSQY LNNGPQRIGR KYKKVRFMAY TDETFKTREA IQHESGILGP LLYGEVGDTL 490        500        510        520        530        540
            |          |          |          |          |          |
     LIIFKNQASR PYNIYPHGIT DVRPLYSRRL PKGVKHLKDF PILPGEIFKY KWTVTVEDGP 550        560        570        580        590        600
            |          |          |          |          |          |
     TKSDPRCLTR YYSSFVNMER DLASGLIGFL LICYKESVDQ RGNQIMSDKR NVILFSVFDE
```

FIG. 8K

```
            610        620        630        640        650        660
             |          |          |          |          |          |
        NRSWYLTENI QRFLPNPAGV QLEDPEFQAS NIMHSINGYV FDSLQLSVCL HEVAYWYILS 670        680        690        700        710        720
             |          |          |          |          |          |
        IGAQTDFLSV FFSGYTFKHK MVYEDTLTLF PFSGETVFMS MENPGLWILG CHNSDFRNRG 730        740        750        760        770        780
             |          |          |          |          |          |
        MTALLKVSSC DKNTGDYYED SYEDISAYLL SKNNAIEPRS FSQNSRHPST RQKQFNATTI 790        800        810        820        830        840
             |          |          |          |          |          |
        PENDIEKTDP WFAHRTPMPK IQNVSSSDLL MLLRQSPTPH GLSLSDLQEA KYETFSDDPS 850        860        870        880        890        900
             |          |          |          |          |          |
        PGAIDSNNSL SEMTHFRPQL HHSGDMVFTP ESGLQLRLNE KLGTTAATEL KKLDFKVSST 910        920        930        940        950        960
             |          |          |          |          |          |
        SNNLISTIPS DNLAAGTDNT SSLGPPSMPV HYDSQLDTTL FGKKSSPLTE SGGPLSLSEE 970        980        990       1000       1010       1020
             |          |          |          |          |          |
        NNDSKLLESG LMNSQESSWG KNVSSTESGR LFKGKRAHGP ALLTKDNALF KVSISLLKTN 1030       1040       1050       1060       1070       1080
             |          |          |          |          |          |
        KTSNNSATNR KTHIDGPSLL IENSPSVWQN ILESDTEFKK VTPLIHDRML MDKNATALRL 1090       1100       1110       1120       1130       1140
             |          |          |          |          |          |
        NHMSNKTTSS KNMEMVQQKK EGPIPPDAQN PDMSFFKMLF LPESARWIQR THGKNSLNSG 1150       1160       1170       1180       1190       1200
             |          |          |          |          |          |
        QGPSPKQLVS LGPEKSVEGQ NFLSEKNKVV VGKGEFTKDV GLKEMVFPSS RNLFLTNLDN 1210       1220       1230       1240       1250       1260
             |          |          |          |          |          |
        LHENNTHNQE KKIQEEIEKK ETLIQENVVL PQIHTVTGTK NFMKNLFLLS TRQNVEGSYD 1270       1280       1290       1300       1310       1320
             |          |          |          |          |          |
        GAYAPVLQDF RSLNDSTNRT KKHTAHFSKK GEEENLEGLG NQTKQIVEKY ACTTRISPNT 1330       1340       1350       1360       1370       1380
             |          |          |          |          |          |
        SQQNFVTQRS KRALKQFRLP LEETELEKRI IVDDTSTQWS KNMKHLTPST LTQIDYNEKE 1390       1400       1410       1420       1430       1440
             |          |          |          |          |          |
        KGAITQSPLS DCLTRSHSIP QANRSPLPIA KVSSFPSIRP IYLTRVLFQD NSSHLPAASY 1450       1460       1470       1480       1490       1500
             |          |          |          |          |          |
        RKKDSGVQES SHFLQGAKKN NLSLAILTLE MTGDQREVGS LGTSATNSVT YKKVENTVLP 1510       1520       1530       1540       1550       1560
             |          |          |          |          |          |
        KPDLPKTSGK VELLPKVHIY QKDLFPTETS NGSPGHLDLV EGSLLQGTEG AIKWNEANRP 1570       1580       1590       1600       1610       1620
             |          |          |          |          |          |
        GKVPFLRVAT ESSAKTPSKL LDPLAWDNHY GTQIPKEEWK SQEKSPEKTA FKKKDTILSL 1630       1640       1650       1660       1670       1680
             |          |          |          |          |          |
        NACESNHAIA AINEGQNKPE IEVTWAKQGR TERLCSQNPP VLKRHQREIT RTTLQSDQEE 1690       1700       1710       1720       1730       1740
             |          |          |          |          |          |
        IDYDDTISVE MKKEDFDIYD EDENQSPRSF QKKTRHYFIA AVERLWDYGM SSSPHVLRNR 1750       1760       1770       1780       1790       1800
             |          |          |          |          |          |
        AQSGSVPQFK KVVFQEFTDG SFTQPLYRGE LNEHLGLLGP YIRAEVEDNI MVTFRNQASR 1810       1820       1830       1840       1850       1860
             |          |          |          |          |          |
        PYSFYSSLIS YEEDQRQGAE PRKNFVKPNE TKTYFWKVQH HMAPTKDEFD CKAWAYFSDV
```

FIG. 8L

```
         1870       1880       1890       1900       1910       1920
          |          |          |          |          |          |
     DLEKDVHSGL IGPLLVCHTN TLNPAHGRQV TVQEFALFFT IFDETKSWYF TENMERNCRA 1930       1940       1950       1960       1970       1980
          |          |          |          |          |          |
     PCNIQMEDPT FKENYRFHAI NGYIMDTLPG LVMAQDQRIR WYLLSMGSNE NIHSIHFSGH 1990       2000       2010       2020       2030       2040
          |          |          |          |          |          |
     VFTVRKKEEY KMALYNLYPG VFETVEMLPS KAGIWRVECL IGEHLHAGMS TLFLVYSNKC 2050       2060       2070       2080       2090       2100
          |          |          |          |          |          |
     QTPLGMASGH IRDFQITASG QYGQWAPKLA RLHYSGSINA WSTKEPFSWI KVDLLAPMII 2110       2120       2130       2140       2150       2160
          |          |          |          |          |          |
     HGIKTQGARQ KFSSLYISQF IIMYSLDGKK WQTYRGNSTG TLMVFFGNVD SSGIKHNIFN 2170       2180       2190       2200       2210       2220
          |          |          |          |          |          |
     PPIIARYIRL HPTHYSIRST LRMELMGCDL NSCSMPLGME SKAISDAQIT ASSYFTNMFA 2230       2240       2250       2260       2270       2280
          |          |          |          |          |          |
     TWSPSKARLH LQGRSNAWRP QVNNPKEWLQ VDFQKTMKVT GVTTQGVKSL LTSMYVKEFL 2290       2300       2310       2320       2330       2340
          |          |          |          |          |          |
     ISSSQDGHQW TLFFQNGKVK VFQGNQDSFT PVVNSLDPPL LTRYLRIHPQ SWVHQIALRM

2350
          |
     EVLGCEAQDL Y
```

FIG. 8M

| ExPASy Home page | Site Map | Search ExPASy | Contact us | SWISS-PROT |

Hosted by SIB Switzerland Mirror sites: Australia Canada China Korea Taiwan

NiceProt View of SWISS-PROT: P12259

| Printer-friendly view | Quick BlastP search |

[General] [Name and origin] [References] [Comments] [Cross-references] [Keywords] [Features] [Sequence] [Tools]

General information about the entry

| | |
|---|---|
| Entry name | FAS_HUMAN |
| Primary accession number | P12259 |
| Secondary accession number | Q14285 |
| Entered in SWISS-PROT in | Release 12, October 1989 |
| Sequence was last modified in | Release 28, February 1994 |
| Annotations were last modified in | Release 40, October 2000 |

Name and origin of the protein

| | |
|---|---|
| Protein name | COAGULATION FACTOR V [Precursor] |
| Synonym | ACTIVATED PROTEIN C COFACTOR |
| Gene name | F5 |
| From | Homo sapiens (Human) [TaxID: 9606] |
| Taxonomy | Eukaryota; Metazoa; Chordata; Craniata; Vertebrata; Euteleostomi; Mammalia; Eutheria; Primates; Catarrhini; Hominidae; Homo. |

References

FIG. 9

[1] SEQUENCE FROM NUCLEIC ACID.
MEDLINE=92232668; PubMed=1567832; [NCBI, ExPASy, EBI, Israel, Japan]
Cripe L.D., Moore K.D., Kane W.H.;
"Structure of the gene for human coagulation factor V.";
Biochemistry 31:3777-3785(1992).

[2] SEQUENCE FROM NUCLEIC ACID.
MEDLINE=87260886; PubMed=3110773; [NCBI, ExPASy, EBI, Israel, Japan]
Jenny R.J., Pittman D.D., Toole J.J., Kriz R.W., Aldape R.A., Hewick R.M., Kaufman R.J., Mann K.G.;
"Complete cDNA and derived amino acid sequence of human factor V.";
Proc. Natl. Acad. Sci. U.S.A. 84:4846-4850(1987).

[3] SEQUENCE OF 1-1600 FROM NUCLEIC ACID.
MEDLINE=88107560; PubMed=2827731; [NCBI, ExPASy, EBI, Israel, Japan]
Kane W.H., Ichinose A., Hagen F.S., Davie E.W.;
"Cloning of cDNAs coding for the heavy chain region and connecting region of human factor V, a blood coagulation factor with four types of internal repeats.";
Biochemistry 26:6508-6514(1987).

[4] SEQUENCE OF 1188-1215 AND 1315-2224 FROM NUCLEIC ACID.
MEDLINE=86313665; PubMed=3092220; [NCBI, ExPASy, EBI, Israel, Japan]
Kane W.H., Davie E.W.;
"Cloning of a cDNA coding for human factor V, a blood coagulation factor homologous to factor VIII and ceruloplasmin.";
Proc. Natl. Acad. Sci. U.S.A. 83:6800-6804(1986).

[5] PARTIAL SEQUENCE FROM NUCLEIC ACID.
TISSUE=Fibroblast;
MEDLINE=93203619; PubMed=8454869; [NCBI, ExPASy, EBI, Israel, Japan]
Shen N.L.L., Fan S.-T., Pyati J., Graff R., Lapolla R.J., Edgington T.S.;
"The serine protease cofactor factor V is synthesized by lymphocytes.";
J. Immunol. 150:2992-3001(1993).

[6] VARIANT APCR GLN-534.
MEDLINE=94217810; PubMed=8164741; [NCBI, ExPASy, EBI, Israel, Japan]
Bertina R.M., Koeleman B.P.C., Koster T., Rosendaal F.R., Dirven R.J., de Ronde H., van der Velden P.A., Reitsma P.H.;
"Mutation in blood coagulation factor V associated with resistance to activated protein C.";
Nature 369:64-67(1994).

Comments

- *FUNCTION*: COAGULATION FACTOR V IS A COFACTOR THAT PARTICIPATES WITH FACTOR XA TO ACTIVATE PROTHROMBIN TO THROMBIN.
- *SUBUNIT*: FACTOR VA IS COMPOSED OF AN HEAVY CHAIN AND OF A LIGHT CHAIN NONCOVALENTLY BOUND. THE INTERACTION BETWEEN THE TWO CHAINS IS CALCIUM-DEPENDENT.
- *DOMAIN*: DOMAIN B CONTAINS 35 X 9 AA TANDEM REPEATS, AND 2 X 17 AA REPEATS.
- *PTM*: THROMBIN ACTIVATES FACTOR V PROTEOLYTICALLY TO THE ACTIVE COFACTOR, FACTOR V(A) (FORMATION OF A HEAVY CHAIN AT THE N-TERMINUS AND A LIGHT CHAIN AT THE C-TERMINUS).
- *DISEASE*: OWREN PARAHEMOPHILIA, AN HEMORRHAGIC DIASTESIS, IS DUE TO A DEFICIENCY OF FACTOR V. OTHER DEFECTS IN F5 RESULTS IN A FORM OF THROMBOPHILIA KNOWN AS APC RESISTANCE (APCR). THE APCR MUTATION IS FOUND IN ABOUT 5% OF THE POPULATION WHICH SUGGEST THAT A SLIGHT THROMBOTIC TENDENCY MAY CONFER SOME ADVANTAGE IN FETAL IMPLANTATION.
- *SIMILARITY*: CONTAINS 3 F5/8 TYPE A DOMAINS; EACH IS COMPOSED OF 2 PLASTOCYANIN-LIKE REPEATS.
- *SIMILARITY*: CONTAINS 2 F5/8 TYPE C DOMAINS.
- *SIMILARITY*: STRONG, TO COAGULATION FACTOR VIII.

Copyright

This SWISS-PROT entry is copyright. It is produced through a collaboration between the Swiss Institute of Bioinformatics and the EMBL outstation - the European Bioinformatics Institute. There are no restrictions on its use by non-profit institutions as long as its content is in no way modified and this statement is not removed. Usage by and for commercial entities requires a license agreement (See http://www.isb-sib.ch/announce/ or send an email to license@isb-sib.ch)

Cross-references

FIG. 9A

| | | |
|---|---|---|
| | L32779; AAB59401.1; -. | [EMBL / GenBank / DDBJ] [CoDingSequence] |
| | L32755; AAB59401.1; JOINED. | [EMBL / GenBank / DDBJ] [CoDingSequence] |
| | L32756; AAB59401.1; JOINED. | [EMBL / GenBank / DDBJ] [CoDingSequence] |
| | L32757; AAB59401.1; JOINED. | [EMBL / GenBank / DDBJ] [CoDingSequence] |
| | L32758; AAB59401.1; JOINED. | [EMBL / GenBank / DDBJ] [CoDingSequence] |
| | L32759; AAB59401.1; JOINED. | [EMBL / GenBank / DDBJ] [CoDingSequence] |
| | L32760; AAB59401.1; JOINED. | [EMBL / GenBank / DDBJ] [CoDingSequence] |
| | L32761; AAB59401.1; JOINED. | [EMBL / GenBank / DDBJ] [CoDingSequence] |
| | L32762; AAB59401.1; JOINED. | [EMBL / GenBank / DDBJ] [CoDingSequence] |
| | L32763; AAB59401.1; JOINED. | [EMBL / GenBank / DDBJ] [CoDingSequence] |
| | L32764; AAB59401.1; JOINED. | [EMBL / GenBank / DDBJ] [CoDingSequence] |
| | L32765; AAB59401.1; JOINED. | [EMBL / GenBank / DDBJ] [CoDingSequence] |
| | L32766; AAB59401.1; JOINED. | [EMBL / GenBank / DDBJ] [CoDingSequence] |
| EMBL | L32767; AAB59401.1; JOINED. | [EMBL / GenBank / DDBJ] [CoDingSequence] |
| | L32768; AAB59401.1; JOINED. | [EMBL / GenBank / DDBJ] [CoDingSequence] |
| | L32769; AAB59401.1; JOINED. | [EMBL / GenBank / DDBJ] [CoDingSequence] |
| | L32770; AAB59401.1; JOINED. | [EMBL / GenBank / DDBJ] [CoDingSequence] |
| | L32771; AAB59401.1; JOINED. | [EMBL / GenBank / DDBJ] [CoDingSequence] |
| | L32772; AAB59401.1; JOINED. | [EMBL / GenBank / DDBJ] [CoDingSequence] |
| | L32773; AAB59401.1; JOINED. | [EMBL / GenBank / DDBJ] [CoDingSequence] |
| | L32774; AAB59401.1; JOINED. | [EMBL / GenBank / DDBJ] [CoDingSequence] |
| | L32775; AAB59401.1; JOINED. | [EMBL / GenBank / DDBJ] [CoDingSequence] |
| | L32776; AAB59401.1; JOINED. | [EMBL / GenBank / DDBJ] [CoDingSequence] |
| | L32777; AAB59401.1; JOINED. | [EMBL / GenBank / DDBJ] [CoDingSequence] |
| | L32778; AAB59401.1; JOINED. | [EMBL / GenBank / DDBJ] [CoDingSequence] |
| | M16967; AAA52424.1; -. | [EMBL / GenBank / DDBJ] [CoDingSequence] |
| | M14335; AAB59532.1; -. | [EMBL / GenBank / DDBJ] [CoDingSequence] |
| PIR | A25897; A25897. | |
| | A28028; A28028. | |
| HSSP | P00450: 1KCW. [HSSP ENTRY / PDB] | |
| | 134400 [NCBI / EBI]. | |
| MIM | 188055 [NCBI / EBI]. | |
| | 227310 [NCBI / EBI]. | |
| | 227400 [NCBI / EBI]. | |
| GeneCards | F5. | |
| | IPR001117: Cu-oxidase. | |
| InterPro | IPR000421: FA58_C. | |
| | Graphical view of domain structure. | |
| Pfam | PF00394: Cu-oxidase: 3. | |
| | PF00754: F5_F8_type_C: 2. | |
| SMART | SM00231: FA58C: 2. | |
| | PS00079: MULTICOPPER_OXIDASE1: 2. | |
| PROSITE | PS01285: FA58C_1: 2. | |
| | PS01286: FA58C_2: 2. | |
| ProDom | [Domain structure / List of seq. sharing at least 1 domain]. | |
| BLOCKS | P12259. | |
| DOMO | P12259. | |
| ProtoMap | P12259. | |
| PRESAGE | P12259. | |
| DIP | P12259. | |
| SWISS-2DPAGE | GET REGION ON 2D PAGE. | |

Keywords

Blood coagulation; Plasma; Glycoprotein; Calcium; Signal; Zymogen; Repeat; Polymorphism; Disease mutation; Thrombophilia.

Features

| Key | From | To | Length | Description |
|---|---|---|---|---|
| SIGNAL | 1 | 28 | 28 | |
| CHAIN | 29 | 2224 | 2196 | COAGULATION FACTOR V. |
| CHAIN | 29 | 737 | 709 | HEAVY CHAIN. |

FIG. 9B

| | | | |
|---|---|---|---|
| PEPTIDE | 738 | 1573 | 836 | ACTIVATION PEPTIDE (CONNECTING REGION). |
| CHAIN | 1574 | 2224 | 651 | LIGHT CHAIN. |
| DOMAIN | 30 | 329 | 300 | F5/8 TYPE A 1. |
| DOMAIN | 30 | 193 | 164 | PLASTOCYANIN-LIKE 1. |
| DOMAIN | 203 | 329 | 127 | PLASTOCYANIN-LIKE 2. |
| DOMAIN | 348 | 684 | 337 | F5/8 TYPE A 2. |
| DOMAIN | 348 | 526 | 179 | PLASTOCYANIN-LIKE 3. |
| DOMAIN | 536 | 684 | 149 | PLASTOCYANIN-LIKE 4. |
| DOMAIN | 692 | 1573 | 882 | B. |
| DOMAIN | 895 | 928 | 34 | 2 X 17 AA TANDEM REPEATS. |
| REPEAT | 895 | 911 | 17 | 1. |
| REPEAT | 912 | 928 | 17 | 2. |
| SIMILAR | 1135 | 1148 | 14 | TO 14 AA REPEATS IN BOVINE FA5. |
| DOMAIN | 1185 | 1463 | 279 | 35 X 9 AA TANDEM REPEATS OF (TNP)-L-S-P-D-L-S-Q-T (APPROXIMATE). |
| REPEAT | 1185 | 1193 | 9 | 1. |
| REPEAT | 1194 | 1202 | 9 | 2. |
| REPEAT | 1203 | 1211 | 9 | 3. |
| REPEAT | 1212 | 1220 | 9 | 4. |
| REPEAT | 1221 | 1229 | 9 | 5. |
| REPEAT | 1230 | 1238 | 9 | 6. |
| REPEAT | 1239 | 1247 | 9 | 7. |
| REPEAT | 1248 | 1256 | 9 | 8. |
| REPEAT | 1257 | 1265 | 9 | 9. |
| REPEAT | 1266 | 1274 | 9 | 10. |
| REPEAT | 1275 | 1283 | 9 | 11. |
| REPEAT | 1284 | 1292 | 9 | 12. |
| REPEAT | 1293 | 1301 | 9 | 13. |
| REPEAT | 1302 | 1310 | 9 | 14. |
| REPEAT | 1311 | 1319 | 9 | 15. |
| REPEAT | 1320 | 1328 | 9 | 16. |
| REPEAT | 1329 | 1337 | 9 | 17. |
| REPEAT | 1338 | 1346 | 9 | 18. |
| REPEAT | 1347 | 1355 | 9 | 19. |
| REPEAT | 1356 | 1364 | 9 | 20. |
| REPEAT | 1365 | 1373 | 9 | 21. |
| REPEAT | 1374 | 1382 | 9 | 22. |
| REPEAT | 1383 | 1391 | 9 | 23. |
| REPEAT | 1392 | 1400 | 9 | 24. |
| REPEAT | 1401 | 1409 | 9 | 25. |
| REPEAT | 1410 | 1418 | 9 | 26. |
| REPEAT | 1419 | 1427 | 9 | 27. |
| REPEAT | 1428 | 1436 | 9 | 28. |
| REPEAT | 1437 | 1445 | 9 | 29. |
| REPEAT | 1446 | 1454 | 9 | 30. |
| REPEAT | 1455 | 1463 | 9 | 31. |
| REPEAT | 1464 | 1472 | 9 | 32. |
| REPEAT | 1473 | 1481 | 9 | 33. |
| REPEAT | 1482 | 1490 | 9 | 34. |
| REPEAT | 1493 | 1501 | 9 | 35. |
| DOMAIN | 1578 | 1907 | 330 | F5/8 TYPE A 3. |
| DOMAIN | 1578 | 1751 | 174 | PLASTOCYANIN-LIKE 5. |
| DOMAIN | 1761 | 1907 | 147 | PLASTOCYANIN-LIKE 6. |
| DOMAIN | 1907 | 2061 | 155 | F5/8 TYPE C 1. |
| DOMAIN | 2066 | 2221 | 156 | F5/8 TYPE C 2. |
| SITE | 737 | 738 | 2 | CLEAVAGE (BY THROMBIN). |
| SITE | 1046 | 1047 | 2 | CLEAVAGE (BY THROMBIN). |
| SITE | 1573 | 1574 | 2 | CLEAVAGE (BY THROMBIN). |
| DISULFID | 167 | 193 | | PROBABLE. |

 Feature aligner

 Feature table viewer

FIG. 9C

| | | | |
|---|---|---|---|
| DISULFID | 500 | 526 | PROBABLE. |
| DISULFID | 1725 | 1751 | PROBABLE. |
| DISULFID | 1907 | 2061 | BY SIMILARITY. |
| DISULFID | 2066 | 2221 | BY SIMILARITY. |
| CARBOHYD | 51 | 51 | N-LINKED (GLCNAC...) (POTENTIAL). |
| CARBOHYD | 55 | 55 | N-LINKED (GLCNAC...) (POTENTIAL). |
| CARBOHYD | 239 | 239 | N-LINKED (GLCNAC...) (POTENTIAL). |
| CARBOHYD | 297 | 297 | N-LINKED (GLCNAC...) (POTENTIAL). |
| CARBOHYD | 382 | 382 | N-LINKED (GLCNAC...) (POTENTIAL). |
| CARBOHYD | 460 | 460 | N-LINKED (GLCNAC...) (POTENTIAL). |
| CARBOHYD | 468 | 468 | N-LINKED (GLCNAC...) (POTENTIAL). |
| CARBOHYD | 554 | 554 | N-LINKED (GLCNAC...) (POTENTIAL). |
| CARBOHYD | 741 | 741 | N-LINKED (GLCNAC...) (POTENTIAL). |
| CARBOHYD | 752 | 752 | N-LINKED (GLCNAC...) (POTENTIAL). |
| CARBOHYD | 760 | 760 | N-LINKED (GLCNAC...) (POTENTIAL). |
| CARBOHYD | 776 | 776 | N-LINKED (GLCNAC...) (POTENTIAL). |
| CARBOHYD | 782 | 782 | N-LINKED (GLCNAC...) (POTENTIAL). |
| CARBOHYD | 821 | 821 | N-LINKED (GLCNAC...) (POTENTIAL). |
| CARBOHYD | 938 | 938 | N-LINKED (GLCNAC...) (POTENTIAL). |
| CARBOHYD | 977 | 977 | N-LINKED (GLCNAC...) (POTENTIAL). |
| CARBOHYD | 1074 | 1074 | N-LINKED (GLCNAC...) (POTENTIAL). |
| CARBOHYD | 1083 | 1083 | N-LINKED (GLCNAC...) (POTENTIAL). |
| CARBOHYD | 1103 | 1103 | N-LINKED (GLCNAC...) (POTENTIAL). |
| CARBOHYD | 1106 | 1106 | N-LINKED (GLCNAC...) (POTENTIAL). |
| CARBOHYD | 1479 | 1479 | N-LINKED (GLCNAC...) (POTENTIAL). |
| CARBOHYD | 1499 | 1499 | N-LINKED (GLCNAC...) (POTENTIAL). |
| CARBOHYD | 1559 | 1559 | N-LINKED (GLCNAC...) (POTENTIAL). |
| CARBOHYD | 1703 | 1703 | N-LINKED (GLCNAC...) (POTENTIAL). |
| CARBOHYD | 2010 | 2010 | N-LINKED (GLCNAC...) (POTENTIAL). |
| CARBOHYD | 2209 | 2209 | N-LINKED (GLCNAC...) (POTENTIAL). |
| VARIANT | 534 | 534 | R -> Q (IN APCR; LEIDEN). /FTId=VAR_001213. |
| VARIANT | 858 | 858 | K -> R. /FTId=VAR_001214. |
| VARIANT | 865 | 865 | H -> R. /FTId=VAR_001215. |
| CONFLICT | 925 | 925 | K -> E (IN REF. 2 AND 3). |
| CONFLICT | 1285 | 1285 | L -> I (IN REF. 3). |
| CONFLICT | 1764 | 1764 | V -> M (IN REF. 1). |
| CONFLICT | 2213 | 2213 | T -> A (IN REF. 4). |

Sequence information

Length: 2224 AA [This is the length of the unprocessed precursor]    Molecular weight: 251699 Da [This is the MW of the unprocessed precursor]    CRC64: 470DD8CD00D2303B [This is a checksum on the sequence]

```
         10         20         30         40         50         60
          |          |          |          |          |          |
MFPGCPRLWV LVVLGTSWVG WGSQGTEAAQ LRQFYVAAQG ISWSYRPEPT NSSLNLSVTS
```

FIG. 9D

```
         70         80         90        100        110        120
          |          |          |          |          |          |
FKKIVYREYE PYFKKEKPQS TISGLLGPTL YAEVGDIIKV HFKNKADKPL SIHPQGIRYS 130        140        150        160        170        180
          |          |          |          |          |          |
KLSEGASYLD HTFPAEKMDD AVAPGREYTY EWSISEDSGP THDDPPCLTH IYYSHENLIE 190        200        210        220        230        240
          |          |          |          |          |          |
DFNSGLIGPL LICKKGTLTE GGTQKTFDKQ IVLLFAVFDE SKSWSQSSSL MYTVNGYVNG 250        260        270        280        290        300
          |          |          |          |          |          |
TMPDITVCAH DHISWHLLGM SSGPELFSIH FNGQVLEQNH HKVSAITLVS ATSTTANMTV 310        320        330        340        350        360
          |          |          |          |          |          |
GPEGKWIISS LTPKHLQAGM QAYIDIKNCP KKTRNLKKIT REQRRHMKRW EYFIAAEEVI 370        380        390        400        410        420
          |          |          |          |          |          |
WDYAPVIPAN MDKKYRSQHL DNFSNQIGKH YKKVMYTQYE DESFTKHTVN PNMKEDGILG 430        440        450        460        470        480
          |          |          |          |          |          |
PIIRAQVRDT LKIVFKNMAS RPYSIYPHGV TFSPYEDEVN SSFTSGRNNT MIRAVQPGET 490        500        510        520        530        540
          |          |          |          |          |          |
YTYKWNILEF DEPTENDAQC LTRPYYSDVD IMRDIASGLI GLLLICKSRS LDRRGIQRAA 550        560        570        580        590        600
          |          |          |          |          |          |
DIEQQAVFAV FDENKSWYLE DNINKFCENP DEVKRDDPKF YESNIMSTIN GYVPESITTL 610        620        630        640        650        660
          |          |          |          |          |          |
GFCFDDTVQW HFCSVGTQNE ILTIHFTGHS FIYGKRHEDT LTLFPMRGES VTVTMDNVGT 670        680        690        700        710        720
          |          |          |          |          |          |
WMLTSMNSSP RSKKLRLKFR DVKCIPDDDE DSYEIFEPPE STVMATRKMH DRLEPEDEES 730        740        750        760        770        780
          |          |          |          |          |          |
DADYDYQNRL AAALGIRSFR NSSLNQEEEE FNLTALALEN GTEFVSSNTD IIVGSNYSSP 790        800        810        820        830        840
          |          |          |          |          |          |
SNISKFTVNN LAEPQKAPSH QQATTAGSPL RHLIGKNSVL NSSTAEHSSP YSEDPIEDPL 850        860        870        880        890        900
          |          |          |          |          |          |
QPDVTGIRLL SLGAGEFKSQ EHAKHKGPKV ERDQAAKHRF SWMKLLAHKV GRHLSQDTGS 910        920        930        940        950        960
          |          |          |          |          |          |
PSGMRPWEDL PSQDTGSPSR MRPWKDPPSD LLLLKQSNSS KILVGRWHLA SEKGSYEIIQ 970        980        990       1000       1010       1020
          |          |          |          |          |          |
DTDEDTAVNN WLISPQNASR AWGESTPLAN KPGKQSGHPK FPRVRHKSLQ VRQDGGKSRL 1030       1040       1050       1060       1070       1080
          |          |          |          |          |          |
KKSQFLIKTR KKKKEKHTHH APLSPRTFHP LRSEAYNTFS ERRLKHSLVL HKSNETSLPT 1090       1100       1110       1120       1130       1140
          |          |          |          |          |          |
DLNQTLPSMD FGWIASLPDH NQNSSNDTGQ ASCPPGLYQT VPPEEHYQTF PIQDPDQMHS 1150       1160       1170       1180       1190       1200
          |          |          |          |          |          |
TSDPSHRSSS PELSEMLEYD RSHKSFPTDI SQMSPSSEHE VWQTVISPDL SQVTLSPELS 1210       1220       1230       1240       1250       1260
          |          |          |          |          |          |
QTNLSPDLSH TTLSPELIQR NLSPALGQMP ISPDLSHTTL SPDLSHTTLS LDLSQTNLSP 1270       1280       1290       1300       1310       1320
          |          |          |          |          |          |
ELSQTNLSPA LGQMPLSPDL SHTTLSLDFS QTNLSPELSH MTLSPELSQT NLSPALGQMP 1330       1340       1350       1360       1370       1380
```

FIG. 9E

```
        |           |           |           |           |           |
ISPDLSHTTL SLDFSQTNLS PELSQTNLSP ALGQMPLSPD PSHTTLSLDL SQTNLSPELS 1390        1400        1410        1420        1430        1440
        |           |           |           |           |           |
QTNLSPDLSE MPLFADLSQI PLTPDLDQMT LSPDLGETDL SPNFGQMSLS PDLSQVTLSP 1450        1460        1470        1480        1490        1500
        |           |           |           |           |           |
DISDTTLLPD LSQISPPPDL DQIFYPSESS QSLLLQEFNE SFPYPDLGQM PSPSSPTLND 1510        1520        1530        1540        1550        1560
        |           |           |           |           |           |
TFLSKEFNPL VIVGLSKDGT DYIEIIPKEE VQSSEDDYAE IDYVPYDDPY KTDVRTNINS 1570        1580        1590        1600        1610        1620
        |           |           |           |           |           |
SRDPDNIAAW YLRSNNGNRR NYYIAAEEIS WDYSEFVQRE TDIEDSDDIP EDTTYKKVVF 1630        1640        1650        1660        1670        1680
        |           |           |           |           |           |
RKYLDSTFTK RDPRGEYEEH LGILGPIIRA EVDDVIQVRF KNLASRPYSL HAHGLSYEKS 1690        1700        1710        1720        1730        1740
        |           |           |           |           |           |
SEGKTYEDDS PEWFKEDNAV QPNSSYTYVW HATERSGPES PGSACRAWAY YSAVNPEKDI 1750        1760        1770        1780        1790        1800
        |           |           |           |           |           |
HSGLIGPLLI CQKGILHKDS NMPVDMREFV LLFMTFDEKK SWYYEKKSRS SWRLTSSEMK 1810        1820        1830        1840        1850        1860
        |           |           |           |           |           |
KSHEFHAING MIYSLPGLKM YEQEWVRLHL LNIGGSQDIH VVHFHGQTLL ENGNKQHQLG 1870        1880        1890        1900        1910        1920
        |           |           |           |           |           |
VWPLLPGSFK TLEMKASKPG WWLLNTEVGE NQRAGMQTPF LIMDRDCRMP MGLSTGIISD 1930        1940        1950        1960        1970        1980
        |           |           |           |           |           |
SQIKASEFLG YWEPRLARLN NGGSYNAWSV EKLAAEFASK PWIQVDMQKE VIITGIQTQG 1990        2000        2010        2020        2030        2040
        |           |           |           |           |           |
AKHYLKSCYT TEFYVAYSSN QINWQIFKGN STRNVMYFNG NSDASTIKEN QFDPPIVARY 2050        2060        2070        2080        2090        2100
        |           |           |           |           |           |
IRISPTRAYN RPTLRLELQG CEVNGCSTPL GMENGKIENK QITASSFKKS WWGDYWEPFR 2110        2120        2130        2140        2150        2160
        |           |           |           |           |           |
ARLNAQGRVN AWQAKANNNK QWLEIDLLKI KKITAIITQG CKSLSSEMYV KSYTIHYSEQ 2170        2180        2190        2200        2210        2220
        |           |           |           |           |           |
GVEWKPYRLK SSMVDKIFEG NTNTKGHVKN FFNPPIISRF IRVIPKTWNQ SITLRLELFG

CDIY                                                         P12259 in FASTA
                                                                    format
```

*View entry in original SWISS-PROT format*
*View entry in raw text format (no links)*
*Report form for errors/updates in this SWISS-PROT entry*

 Direct BLAST submission at EMBnet-CH and CSCS (Switzerland)

 Direct BLAST submission at NCBI (Bethesda, USA)

 ScanProsite, ProfileScan

 Tools Sequence analysis tools: ProtParam, ProtScale, Compute pI/Mw, PeptideMass, Dotlet (Java)

 Feature table viewer (Java)

 Search the SWISS-MODEL Repository

FIG. 9F

| ExPASy Home page | Site Map | Search ExPASy | Contact us | SWISS-PROT |

Hosted by SIB Switzerland Mirror sites: Australia Canada China Korea Taiwan

NiceProt View of SWISS-PROT: P00734

| Printer-friendly view | Quick BlastP search |

[General] [Name and origin] [References] [Comments] [Cross-references] [Keywords] [Features] [Sequence] [Tools]

General information about the entry

| | |
|---|---|
| Entry name | THRB_HUMAN |
| Primary accession number | P00734 |
| Secondary accession numbers | None |
| Entered in SWISS-PROT in | Release 01, July 1986 |
| Sequence was last modified in | Release 13, January 1990 |
| Annotations were last modified in | Release 40, October 2000 |

Name and origin of the protein

| | |
|---|---|
| Protein name | PROTHROMBIN [Precursor] |
| Synonyms | EC 3.4.21.5<br>COAGULATION FACTOR II |
| Gene name | F2 |
| From | Homo sapiens (Human) [TaxID: 9606] |
| Taxonomy | Eukaryota; Metazoa; Chordata; Craniata; Vertebrata; Euteleostomi; Mammalia; Eutheria; Primates; Catarrhini; Hominidae; Homo. |

References

[1] SEQUENCE FROM NUCLEIC ACID.
MEDLINE=88077877; PubMed=2825773; [NCBI, ExPASy, EBI, Israel, Japan]
Degen S.J.F., Davie E.W.;
"Nucleotide sequence of the gene for human prothrombin.";
Biochemistry 26:6165-6177(1987).

[2] SEQUENCE OF 8-622 FROM NUCLEIC ACID.
MEDLINE=83231469; PubMed=6305407; [NCBI, ExPASy, EBI, Israel, Japan]
Degen S.J.F., McGillivray R.T.A., Davie E.W.;
"Characterization of the complementary deoxyribonucleic acid and gene coding for human prothrombin.";
Biochemistry 22:2087-2097(1983).

[3] SEQUENCE OF 44-314.
MEDLINE=77193964; PubMed=266717; [NCBI, ExPASy, EBI, Israel, Japan]
Walz D.A., Hewett-Emmett D., Seegers W.H.;
"Amino acid sequence of human prothrombin fragments 1 and 2.";
Proc. Natl. Acad. Sci. U.S.A. 74:1969-1972(1977).

[4] SEQUENCE OF 315-622.
MEDLINE=77207112; PubMed=873923; [NCBI, ExPASy, EBI, Israel, Japan]
Butkowski R.J., Elion J., Downing M.R., Mann K.G.;
"Primary structure of human prethrombin 2 and alpha-thrombin.";
J. Biol. Chem. 252:4942-4957(1977).

[5] PROCESSING.
MEDLINE=87008532; PubMed=3759958; [NCBI, ExPASy, EBI, Israel, Japan]
Rabiet M.J., Blashill A., Furie B., Furie B.C.;
"Prothrombin fragment 1 X 2 X 3, a major product of prothrombin activation in human plasma.";
J. Biol. Chem. 261:13210-13215(1986).

[6] X-RAY CRYSTALLOGRAPHY (1.9 ANGSTROMS).
MEDLINE=90059942; PubMed=2583108; [NCBI, ExPASy, EBI, Israel, Japan]
Bode W., Mayr I., Baumann U., Huber R., Stone S.R., Hofsteenge J.;
"The refined 1.9 A crystal structure of human alpha-thrombin: interaction with D-Phe-Pro-Arg

FIG. 10 chloromethylketone and significance of the Tyr-Pro-Pro-Trp insertion segment.";
EMBO J. 8:3467-3475(1989).

[7] X-RAY CRYSTALLOGRAPHY (2.3 ANGSTROMS).
MEDLINE=90327074; PubMed=2374926; [NCBI, ExPASy, EBI, Israel, Japan]
Rydel T.J., Ravichandran K.G., Tulinsky A., Bode W., Huber R., Roitsch C., Fenton J.W. II;
"The structure of a complex of recombinant hirudin and human alpha-thrombin.";
Science 249:277-280(1990).

[8] X-RAY CRYSTALLOGRAPHY (2.5 ANGSTROMS).
MEDLINE=94350942; PubMed=8071320; [NCBI, ExPASy, EBI, Israel, Japan]
Rydel T.J., Yin M., Padmanabhan K.P., Blankenship D.T., Cardin A.D., Correa P.E., Fenton J.W. II, Tulinsky A.;
"Crystallographic structure of human gamma-thrombin.";
J. Biol. Chem. 269:22000-22006(1994).

[9] X-RAY CRYSTALLOGRAPHY (2.3 ANGSTROMS).
MEDLINE=97357286; PubMed=9214615; [NCBI, ExPASy, EBI, Israel, Japan]
van de Locht A., Bode W., Huber R., le Bonniec B.F., Stone S.R., Esmon C.T., Stubbs M.T.;
"The thrombin E192Q-BPTI complex reveals gross structural rearrangements: implications for the interaction with antithrombin and thrombomodulin.";
EMBO J. 16:2977-2984(1997).

[10] X-RAY CRYSTALLOGRAPHY (2.1 ANGSTROMS) OF 328-601.
MEDLINE=99162521; PubMed=10051558; [NCBI, ExPASy, EBI, Israel, Japan]
Guinto E.R., Caccia S., Rose T., Fuetterer K., Waksman G., di Cera E.;
"Unexpected crucial role of residue 225 in serine proteases.";
Proc. Natl. Acad. Sci. U.S.A. 96:1852-1857(1999).

[11] VARIANT BARCELONA.
MEDLINE=87033739; PubMed=3771562; [NCBI, ExPASy, EBI, Israel, Japan]
Rabiet M.-J., Furie B.C., Furie B.;
"Molecular defect of prothrombin Barcelona. Substitution of cysteine for arginine at residue 273.";
J. Biol. Chem. 261:15045-15048(1986).

[12] VARIANT FRANKFURT.
MEDLINE=95313001; PubMed=7792730; [NCBI, ExPASy, EBI, Israel, Japan]
Degen S.J.F., McDowell S.A., Sparks L.M., Scharrer I.;
"Prothrombin Frankfurt: a dysfunctional prothrombin characterized by substitution of Glu-466 by Ala.";
Thromb. Haemost. 73:203-209(1995).

[13] VARIANTS HIMI-1 AND HIMI-2.
MEDLINE=93043342; PubMed=1421398; [NCBI, ExPASy, EBI, Israel, Japan]
Morishita E., Saito M., Kumabashiri I., Asakura H., Matsuda T., Yamaguchi K.;
"Prothrombin Himi: a compound heterozygote for two dysfunctional prothrombin molecules (Met-337-->Thr and Arg-388-->His).";
Blood 80:2275-2280(1992).

[14] VARIANT PADUA-1.
MEDLINE=95169898; PubMed=7865694; [NCBI, ExPASy, EBI, Israel, Japan]
James H.L., Kim D.J., Zheng D.-Q., Girolami A.;
"Prothrombin Padua I: incomplete activation due to an amino acid substitution at a factor Xa cleavage site.";
Blood Coagul. Fibrinolysis 5:841-844(1994).

[15] VARIANT QUICK-1.
MEDLINE=89207504; PubMed=3242619; [NCBI, ExPASy, EBI, Israel, Japan]
Henriksen R.A., Mann K.G.;
"Identification of the primary structural defect in the dysthrombin thrombin Quick 1: substitution of cysteine for arginine-382.";
Biochemistry 27:9160-9165(1988).

[16] VARIANT QUICK-2.
MEDLINE=89247398; PubMed=2719946; [NCBI, ExPASy, EBI, Israel, Japan]
Henriksen R.A., Mann K.G.;
"Substitution of valine for glycine-558 in the congenital dysthrombin thrombin Quick II alters primary substrate specificity.";
Biochemistry 28:2078-2082(1989).

[17] VARIANT SALAKTA.
MEDLINE=92378975; PubMed=1354985; [NCBI, ExPASy, EBI, Israel, Japan]
Miyata T., Aruga R., Umeyama H., Bezeaud A., Guillin M.-C., Iwanaga S.;
"Prothrombin Salakta: substitution of glutamic acid-466 by alanine reduces the fibrinogen clotting activity and the esterase activity.";
Biochemistry 31:7457-7462(1992).

FIG. 10A

[18] VARIANT TOKUSHIMA.
   MEDLINE=87185407; PubMed=3567158; [NCBI, ExPASy, EBI, Israel, Japan]
   Miyata T., Morita T., Inomoto T., Kawauchi S., Shirakami A., Iwanaga S.;
   "Prothrombin Tokushima, a replacement of arginine-418 by tryptophan that impairs the fibrinogen clotting activity of derived thrombin Tokushima.";
   Biochemistry 26:1117-1122(1987).

[19] VARIANT TOKUSHIMA.
   MEDLINE=87101511; PubMed=3801671; [NCBI, ExPASy, EBI, Israel, Japan]
   Inomoto T., Shirakami A., Kawauchi S., Shigekiyo T., Saito S., Miyoshi K., Morita T., Iwanaga S.;
   "Prothrombin Tokushima: characterization of dysfunctional thrombin derived from a variant of human prothrombin.";
   Blood 69:565-569(1987).

[20] VARIANT TOKUSHIMA.
   MEDLINE=92256895; PubMed=1349838; [NCBI, ExPASy, EBI, Israel, Japan]
   Iwahana H., Yoshimoto K., Shigekiyo T., Shirakami A., Saito S., Itakura M.;
   "Detection of a single base substitution of the gene for prothrombin Tokushima. The application of PCR-SSCP for the genetic and molecular analysis of dysprothrombinemia.";
   Int. J. Hematol. 55:93-100(1992).

[21] VARIANT TYPE-3.
   MEDLINE=83204687; PubMed=6405779; [NCBI, ExPASy, EBI, Israel, Japan]
   Board P.G., Shaw D.C.;
   "Determination of the amino acid substitution in human prothrombin type 3 (157 Glu leads to Lys) and the localization of a third thrombin cleavage site.";
   Br. J. Haematol. 54:245-254(1983).

Comments

- *FUNCTION*: THROMBIN, WHICH CLEAVES BONDS AFTER ARG & LYS. CONVERTS FIBRINOGEN TO FIBRIN AND ACTIVATES FACTORS V, VII, VIII, XIII. AND. IN COMPLEX WITH THROMBOMODULIN, PROTEIN C.
- *SUBCELLULAR LOCATION*: EXTRACELLULAR.
- *TISSUE SPECIFICITY*: SYNTHESIZED IN THE LIVER; FOUND IN PLASMA.
- *PTM*: THE GAMMA-CARBOXYGLUTAMYL RESIDUES, WHICH BIND CALCIUM IONS, RESULT FROM THE CARBOXYLATION OF GLUTAMYL RESIDUES BY A MICROSOMAL ENZYME, THE VITAMIN K-DEPENDENT CARBOXYLASE. THE MODIFIED RESIDUES ARE NECESSARY FOR THE CA-DEPENDENT INTERACTION WITH A NEGATIVELY CHARGED PHOSPHOLIPID SURFACE, WHICH IS ESSENTIAL FOR THE CONVERSION OF PROTHROMBIN TO THROMBIN.
- *DISEASE*: DEFECTS IN F2 ARE THE CAUSE OF VARIOUS FORMS OF DYSPROTHROMBINEMIA.
- *MISCELLANEOUS*: PROTHROMBIN IS ACTIVATED ON THE SURFACE OF A PHOSPHOLIPID MEMBRANE THAT BINDS THE AMINO END OF PROTHROMBIN & FACTORS VA & XA IN CA-DEPENDENT INTERACTIONS; FACTOR XA REMOVES THE ACTIVATION PEPTIDE & CLEAVES THE REMAINING PART INTO LIGHT & HEAVY CHAINS. THE ACTIVATION PROCESS STARTS SLOWLY BECAUSE FACTOR V ITSELF HAS TO BE ACTIVATED BY THE INITIAL, SMALL AMOUNTS OF THROMBIN.
- *MISCELLANEOUS*: IT IS NOT KNOWN WHETHER 1 OR 2 SMALLER ACTIVATION PEPTIDES, WITH ADDITIONAL CLEAVAGE AFTER 314-ARG, ARE RELEASED IN NATURAL BLOOD CLOTTING.
- *MISCELLANEOUS*: THROMBIN CAN ITSELF CLEAVE THE AMINO TERMINAL FRAGMENT (FRAGMENT 1) OF THE PROTHROMBIN, PRIOR TO ITS ACTIVATION BY FACTOR XA.
- *MISCELLANEOUS*: THE CLEAVAGE AFTER R-198, OBSERVED IN VITRO, DOES NOT OCCUR IN PLASMA.
- *SIMILARITY*: CONTAINS 2 KRINGLE DOMAINS.
- *SIMILARITY*: BELONGS TO PEPTIDASE FAMILY S1; ALSO KNOWN AS THE TRYPSIN FAMILY.

Copyright

This SWISS-PROT entry is copyright. It is produced through a collaboration between the Swiss Institute of Bioinformatics and the EMBL outstation - the European Bioinformatics Institute There are no restrictions on its use by non-profit institutions as long as its content is in no way modified and this statement is not removed Usage by and for commercial entities requires a license agreement (See http //www isb-sib ch/announce/ or send an email to license@isb-sib ch)

Cross-references

| | |
|---|---|
| EMBL | M17262; AAC63054.1; -. [EMBL / GenBank / DDBJ] [CoDingSequence] |
| | V00595; CAA23842.1; -. [EMBL / GenBank / DDBJ] [CoDingSequence] |

FIG. 10B

| | |
|---|---|
| PIR | A00914: TBHU.<br>A29351; A29351. |
| PDB | 1DWB; 31-JAN-94. [ExPASy / RCSB]<br>1DWC; 31-JAN-94. [ExPASy / RCSB]<br>1DWD; 31-JAN-94. [ExPASy / RCSB]<br>1DWE; 31-JAN-94. [ExPASy / RCSB]<br>3HAT; 27-FEB-95. [ExPASy / RCSB]<br>1HGT; 31-JAN-94. [ExPASy / RCSB]<br>2HGT; 31-JAN-94. [ExPASy / RCSB]<br>1ABI; 31-JAN-94. [ExPASy / RCSB]<br>1ABJ; 31-JAN-94. [ExPASy / RCSB]<br>1AD8; 12-NOV-97. [ExPASy / RCSB]<br>1AE8; 03-DEC-97. [ExPASy / RCSB]<br>1AFE; 03-DEC-97. [ExPASy / RCSB]<br>1AHT; 17-MAR-96. [ExPASy / RCSB]<br>1AI8; 15-OCT-97. [ExPASy / RCSB]<br>1AIX; 15-OCT-97. [ExPASy / RCSB]<br>1BMM; 07-DEC-96. [ExPASy / RCSB]<br>1BMN; 07-DEC-96. [ExPASy / RCSB]<br>1DIT; 10-JUN-96. [ExPASy / RCSB]<br>1FPC; 27-FEB-95. [ExPASy / RCSB]<br>1HAG; 20-DEC-94. [ExPASy / RCSB]<br>1HAH; 20-DEC-94. [ExPASy / RCSB]<br>1HAI; 20-DEC-94. [ExPASy / RCSB]<br>1HDT; 15-OCT-95. [ExPASy / RCSB]<br>1HAO; 03-APR-96. [ExPASy / RCSB]<br>1HAP; 03-APR-96. [ExPASy / RCSB]<br>1HBT; 10-JUL-95. [ExPASy / RCSB]<br>1HLT; 20-DEC-94. [ExPASy / RCSB]<br>2HNT; 30-NOV-94. [ExPASy / RCSB]<br>1HUT; 22-JUN-94. [ExPASy / RCSB]<br>3HTC; 31-JAN-94. [ExPASy / RCSB]<br>4HTC; 31-JAN-94. [ExPASy / RCSB]<br>1HXE; 08-NOV-96. [ExPASy / RCSB]<br>1HXF; 27-JAN-97. [ExPASy / RCSB]<br>1IHS; 31-JAN-94. [ExPASy / RCSB]<br>1IHT; 31-JAN-94. [ExPASy / RCSB]<br>1LHC; 08-NOV-96. [ExPASy / RCSB]<br>1LHD; 08-NOV-96. [ExPASy / RCSB]<br>1LHE; 08-NOV-96. [ExPASy / RCSB]<br>1LHF; 08-NOV-96. [ExPASy / RCSB]<br>1LHG; 08-NOV-96. [ExPASy / RCSB]<br>1NRN; 31-MAY-94. [ExPASy / RCSB]<br>1NRO; 31-MAY-94. [ExPASy / RCSB]<br>1NRP; 31-MAY-94. [ExPASy / RCSB]<br>1NRQ; 31-MAY-94. [ExPASy / RCSB]<br>1NRR; 31-MAY-94. [ExPASy / RCSB]<br>1NRS; 31-MAY-94. [ExPASy / RCSB]<br>1PPB; 31-JAN-94. [ExPASy / RCSB]<br>1THR; 31-JAN-94. [ExPASy / RCSB]<br>1THS; 31-JAN-94. [ExPASy / RCSB]<br>1TMB; 31-JAN-94. [ExPASy / RCSB]<br>1TMT; 30-SEP-94. [ExPASy / RCSB]<br>1TMU; 30-SEP-94. [ExPASy / RCSB]<br>1TOM; 12-MAR-97. [ExPASy / RCSB]<br>1UMA; 08-NOV-96. [ExPASy / RCSB]<br>1UVS; 19-NOV-97. [ExPASy / RCSB]<br>1UVT; 19-NOV-97. [ExPASy / RCSB]<br>1UVU; 19-NOV-97. [ExPASy / RCSB]<br>1BTH; 24-DEC-97. [ExPASy / RCSB] |

FIG. 10C

|         |                           |
|---------|---------------------------|
|         | 1AY6; 18-MAR-98. [ExPASy / RCSB] |
|         | 1A4W; 29-APR-98. [ExPASy / RCSB] |
|         | 1B5G; 27-MAY-98. [ExPASy / RCSB] |
|         | 1TBZ; 27-MAY-98. [ExPASy / RCSB] |
|         | 1A46; 27-MAY-98. [ExPASy / RCSB] |
|         | 1A61; 17-JUN-98. [ExPASy / RCSB] |
|         | 1A2C; 01-JUL-98. [ExPASy / RCSB] |
|         | 1A3B; 03-JUN-98. [ExPASy / RCSB] |
|         | 1A3E; 03-JUN-98. [ExPASy / RCSB] |
|         | 1A5G; 27-MAY-98. [ExPASy / RCSB] |
|         | 1BHX; 06-JAN-99. [ExPASy / RCSB] |
|         | 1B7X; 02-MAR-99. [ExPASy / RCSB] |
|         | 1AWF; 18-NOV-98. [ExPASy / RCSB] |
|         | 1AWH; 18-NOV-98. [ExPASy / RCSB] |
|         | 1THP; 07-MAR-99. [ExPASy / RCSB] |
|         | 2THF; 07-MAR-99. [ExPASy / RCSB] |
|         | 1VR1; 16-DEC-98. [ExPASy / RCSB] |
|         | 7KME; 25-MAR-99. [ExPASy / RCSB] |
|         | 8KME; 24-MAR-99. [ExPASy / RCSB] |
|         | 1BA8; 27-APR-99. [ExPASy / RCSB] |
|         | 1BB0; 27-APR-99. [ExPASy / RCSB] |
| MEROPS  | S01.217; -. |
| SWISS-2DPAGE | P00734; HUMAN. |
| MIM     | 176930 [NCBI / EBI]. |
| GeneCards | F2. |
| InterPro | IPR001314: Chymotrypsin.<br>IPR002383: GLA_blood.<br>IPR000001: Kringle.<br>IPR001254: Trypsin.<br>IPR000294: VitK_dep_GLA.<br>Graphical view of domain structure. |
| Pfam    | PF00594; gla; 1.<br>PF00051; kringle; 2.<br>PF00089; trypsin; 1. |
| PRINTS  | PR00001; GLABLOOD.<br>PR00018; KRINGLE.<br>PR00722; CHYMOTRYPSIN. |
| SMART   | SM00069; GLA; 1.<br>SM00130; KR; 2.<br>SM00020; Tryp_SPc; 1. |
| PROSITE | PS00011; GLU_CARBOXYLATION; 1.<br>PS00021; KRINGLE_1; 2.<br>PS50070; KRINGLE_2; 2.<br>PS50240; TRYPSIN_DOM; 1.<br>PS00134; TRYPSIN_HIS; 1.<br>PS00135; TRYPSIN_SER; 1. |
| ProDom  | [Domain structure / List of seq. sharing at least 1 domain]. |
| BLOCKS  | P00734. |
| DOMO    | P00734. |
| ProtoMap | P00734. |
| PRESAGE | P00734. |
| DIP     | P00734. |

Keywords

Blood coagulation; Plasma; Calcium-binding; Glycoprotein; Duplication; Vitamin K; Zymogen; Gamma-carboxyglutamic acid; Acute phase; Liver; Hydrolase; Serine protease; Kringle; Signal; 3D-structure; Disease mutation.

Features

| Key    | From | To | Length | Description |
|--------|------|-----|--------|-------------|
| SIGNAL | 1    | 24  | 24     | *POTENTIAL.* |
| PROPEP | 25   | 43  | 19     |             |

FIG. 10D

| | | | |
|---|---|---|---|
| CHAIN | 44 | 622 | 579 PROTHROMBIN. |
| PEPTIDE | 44 | 198 | 155 ACTIVATION PEPTIDE (FRAGMENT 1). |
| PEPTIDE | 199 | 327 | 129 ACTIVATION PEPTIDE (FRAGMENT 2). |
| CHAIN | 328 | 363 | 36 THROMBIN LIGHT CHAIN (A). |
| CHAIN | 364 | 622 | 259 THROMBIN HEAVY CHAIN (B). |
| DOMAIN | 108 | 186 | 79 KRINGLE 1. |
| DOMAIN | 213 | 291 | 79 KRINGLE 2. |
| DOMAIN | 364 | 622 | 259 SERINE PROTEASE. |
| SITE | 198 | 199 | 2 CLEAVAGE (BY THROMBIN). |
| SITE | 327 | 328 | 2 CLEAVAGE (BY FACTOR XA). |
| SITE | 363 | 364 | 2 CLEAVAGE (BY FACTOR XA). |
| ACT_SITE | 406 | 406 | CHARGE RELAY SYSTEM. |
| ACT_SITE | 462 | 462 | CHARGE RELAY SYSTEM. |
| ACT_SITE | 568 | 568 | CHARGE RELAY SYSTEM. |
| MOD_RES | 49 | 49 | GAMMA-CARBOXYGLUTAMIC ACID. |
| MOD_RES | 50 | 50 | GAMMA-CARBOXYGLUTAMIC ACID. |
| MOD_RES | 57 | 57 | GAMMA-CARBOXYGLUTAMIC ACID. |
| MOD_RES | 59 | 59 | GAMMA-CARBOXYGLUTAMIC ACID. |
| MOD_RES | 62 | 62 | GAMMA-CARBOXYGLUTAMIC ACID. |
| MOD_RES | 63 | 63 | GAMMA-CARBOXYGLUTAMIC ACID. |
| MOD_RES | 68 | 68 | GAMMA-CARBOXYGLUTAMIC ACID. |
| MOD_RES | 69 | 69 | GAMMA-CARBOXYGLUTAMIC ACID. |
| MOD_RES | 72 | 72 | GAMMA-CARBOXYGLUTAMIC ACID. |
| MOD_RES | 75 | 75 | GAMMA-CARBOXYGLUTAMIC ACID. |
| CARBOHYD | 121 | 121 | N-LINKED (GLCNAC...). |
| CARBOHYD | 143 | 143 | N-LINKED (GLCNAC...). |
| CARBOHYD | 416 | 416 | N-LINKED (GLCNAC...). |
| DISULFID | 60 | 65 | |
| DISULFID | 90 | 103 | |
| DISULFID | 108 | 186 | |
| DISULFID | 129 | 169 | |
| DISULFID | 157 | 181 | |
| DISULFID | 213 | 291 | |
| DISULFID | 234 | 274 | |
| DISULFID | 262 | 286 | |
| DISULFID | 336 | 482 | INTERCHAIN. |
| DISULFID | 391 | 407 | |
| DISULFID | 536 | 550 | BY SIMILARITY. |
| DISULFID | 564 | 594 | BY SIMILARITY. |
| VARIANT | 200 | 200 | E -> K (IN TYPE 3; DYSPROTHROMBINEMIA). /FTId=VAR_006711. |
| VARIANT | 314 | 314 | R -> C (IN BARCELONA/MADRID; DYSPROTHROMBINEMIA). /FTId=VAR_006712. |
| VARIANT | 314 | 314 | R -> H (IN PALUA-1; DYSPROTHROMBINEMIA). /FTId=VAR_006713. |
| VARIANT | 380 | 380 | M -> T (IN HIMI-1; DYSPROTHROMBINEMIA). /FTId=VAR_006714. |
| VARIANT | 425 | 425 | R -> C (IN QUICK-1; DYSPROTHROMBINEMIA). /FTId=VAR_006715. |
| VARIANT | 431 | 431 | R -> H (IN HIMI-2; DYSPROTHROMBINEMIA). /FTId=VAR_006716. |
| VARIANT | 461 | 461 | R -> W (IN TOKUSHIMA; DYSPROTHROMBINEMIA). /FTId=VAR_006717. |
| VARIANT | 509 | 509 | E -> A (IN SALAKTA/FRANKFURT). /FTId=VAR_006718. |
| VARIANT | 601 | 601 | G -> V (IN QUICK-2; DYSPROTHROMBINEMIA). /FTId=VAR_006719. |
| CONFLICT | 119 | 119 | H -> N (IN REF. 3). |

FIG. 10E

| | | | |
|---|---|---|---|
| CONFLICT | 121 | 121 | N -> S (IN REF. 3). |
| CONFLICT | 164 | 164 | T -> N (IN REF. 2). |
| CONFLICT | 164 | 164 | T -> I (IN REF. 3). |
| CONFLICT | 176 | 176 | V -> A (IN REF. 3). |
| CONFLICT | 183 | 183 | I -> T (IN REF. 3). |
| CONFLICT | 194 | 195 | AM -> MV (IN REF. 3). |
| CONFLICT | 308 | 308 | D -> DEE (IN REF. 3). |
| CONFLICT | 335 | 335 | D -> N (IN REF. 4). |
| CONFLICT | 349 | 349 | D -> N (IN REF. 4). |
| CONFLICT | 369 | 369 | D -> N (IN REF. 4). |
| CONFLICT | 398 | 398 | D -> N (IN REF. 4). |
| CONFLICT | 414 | 414 | D -> N (IN REF. 4). |
| CONFLICT | 485 | 485 | D -> N (IN REF. 4). |
| CONFLICT | 494 | 494 | Q -> G (IN REF. 4). |
| CONFLICT | 504 | 504 | W -> Y (IN REF. 4). |
| CONFLICT | 509 | 509 | E -> S (IN REF. 4). |
| CONFLICT | 511 | 511 | W -> V (IN REF. 4). |
| CONFLICT | 514 | 514 | N -> D (IN REF. 4). |
| CONFLICT | 529 | 530 | PI -> AL (IN REF. 4). |
| CONFLICT | 532 | 532 | E -> Q (IN REF. 4). |
| TURN | 336 | 337 | 2 |
| TURN | 340 | 346 | 7 |
| TURN | 350 | 351 | 2 |
| HELIX | 352 | 356 | 5 |
| TURN | 357 | 358 | 2 |
| STRAND | 365 | 365 | 1 |
| STRAND | 368 | 369 | 2 |
| TURN | 372 | 373 | 2 |
| TURN | 376 | 377 | 2 |
| STRAND | 378 | 383 | 6 |
| TURN | 384 | 387 | 4 |
| STRAND | 388 | 395 | 8 |
| STRAND | 400 | 403 | 4 |
| HELIX | 405 | 407 | 3 |
| TURN | 409 | 408 | 1 |
| STRAND | 409 | 410 | 2 |
| HELIX | 411 | 413 | 3 |
| TURN | 414 | 414 | 1 |
| STRAND | 415 | 416 | 2 |
| HELIX | 419 | 421 | 3 |
| STRAND | 422 | 426 | 5 |
| TURN | 436 | 438 | 3 |
| STRAND | 440 | 449 | 10 |
| TURN | 451 | 452 | 2 |
| STRAND | 454 | 454 | 1 |
| TURN | 455 | 458 | 4 |
| STRAND | 460 | 460 | 1 |
| STRAND | 464 | 468 | 5 |
| STRAND | 475 | 475 | 1 |
| TURN | 476 | 477 | 2 |
| STRAND | 478 | 478 | 1 |
| STRAND | 482 | 482 | 1 |
| HELIX | 486 | 492 | 7 |
| TURN | 495 | 496 | 2 |
| STRAND | 498 | 503 | 6 |
| TURN | 510 | 511 | 2 |
| STRAND | 524 | 530 | 7 |
| HELIX | 533 | 538 | 6 |
| TURN | 539 | 539 | 1 |
| TURN | 546 | 547 | 2 |

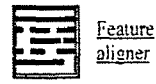 Feature aligner

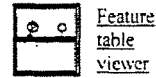 Feature table viewer

FIG. 10F

| | | | |
|---|---|---|---|
| STRAND | 548 | 551 | 4 |
| TURN | 555 | 557 | 3 |
| STRAND | 562 | 562 | 1 |
| TURN | 565 | 566 | 2 |
| TURN | 568 | 569 | 2 |
| STRAND | 571 | 575 | 5 |
| TURN | 577 | 579 | 3 |
| STRAND | 582 | 590 | 9 |
| TURN | 597 | 598 | 2 |
| STRAND | 601 | 605 | 5 |
| HELIX | 606 | 617 | 12 |
| TURN | 618 | 618 | 1 |

Sequence information

Length: 622 AA [This is the length of the unprocessed precursor]

Molecular weight: 70036 Da [This is the MW of the unprocessed precursor]

CRC64: 8A25E1DA88208FCF [This is a checksum on the sequence]

```
         10         20         30         40         50         60
          |          |          |          |          |          |
MAHVRGLQLP GCLALAALCS LVHSQHVFLA PQQARSLLQR VRRANTFLEE VRKGNLEREC 70         80         90        100        110        120
          |          |          |          |          |          |
VEETCSYEEA FEALESSTAT DVFWAKYTAC ETARTPRDKL AACLEGNCAE GLGTNYRGHV 130        140        150        160        170        180
          |          |          |          |          |          |
NITRSGIECQ LWRSRYPHKP EINSTTHPGA DLQENFCRNP DSSTTGPWCY TTDPTVRRQE 190        200        210        220        230        240
          |          |          |          |          |          |
CSIPVCGQDQ VTVAMTPRSE GSSVNLSPPL EQCVPDRGQQ YQGRLAVTTH GLPCLAWASA 250        260        270        280        290        300
          |          |          |          |          |          |
QAKALSKHQD FNSAVQLVEN FCRNPDGDEE GVWCYVAGKP GDFGYCDLNY CEEAVEEETG 310        320        330        340        350        360
          |          |          |          |          |          |
DGLDEDSDRA IEGRTATSEY QTFFNPRTFG SGEADCGLRP LFEKKSLEDK TERELLESYI 370        380        390        400        410        420
          |          |          |          |          |          |
DGRIVEGSDA EIGMSPWQVM LFRKSPQELL CGASLISDRW VLTAAHCLLY PPWDKNFTEN 430        440        450        460        470        480
          |          |          |          |          |          |
DLLVRIGKHS RTRYERNIEK ISMLEKIYIH PRYNWRENLD RDIALMKLKK PVAFSDYIHP 490        500        510        520        530        540
          |          |          |          |          |          |
VCLPDRETAA SLLQAGYKGR VTGWGNLKET WTANVGKGQP SVLQVVNLPI VERPVCKDST 550        560        570        580        590        600
          |          |          |          |          |          |
RIRITDNMFC AGYKPDEGKR GDACEGDSGG PFVMKSPFNN RWYQMGIVSW GEGCDRDGKY 610        620
          |          |
GFYTHVFRLK KWIQKVIDQF GE
```

P00734 in FASTA format

*View entry in original SWISS-PROT format*
*View entry in raw text format (no links)*
*Report form for errors/updates in this SWISS-PROT entry*

FIG. 10G

| ExPASy Home page | Site Map | Search ExPASy | Contact us | SWISS-PROT |

Hosted by SIB Switzerland Mirror sites: Australia Canada China Korea Taiwan

NiceProt View of SWISS-PROT: P00748

| Printer-friendly view | Quick BlastP search |

[General] [Name and origin] [References] [Comments] [Cross-references] [Keywords] [Features] [Sequence] [Tools]

General information about the entry

| | |
|---|---|
| Entry name | FA12_HUMAN |
| Primary accession number | P00748 |
| Secondary accession number | P78339 |
| Entered in SWISS-PROT in | Release 01, July 1986 |
| Sequence was last modified in | Release 12, October 1989 |
| Annotations were last modified in | Release 40, October 2000 |

Name and origin of the protein

| | |
|---|---|
| Protein name | COAGULATION FACTOR XII [Precursor] |
| Synonyms | EC 3.4.21.38<br>HAGEMAN FACTOR<br>HAF |
| Gene name | F12 |
| From | Homo sapiens (Human) [TaxID: 9606] |
| Taxonomy | Eukaryota; Metazoa; Chordata; Craniata; Vertebrata; Euteleostomi; Mammalia; Eutheria; Primates; Catarrhini; Hominidae; Homo. |

References

FIG. 11

[1] SEQUENCE FROM NUCLEIC ACID.
MEDLINE=88007593; PubMed=2888762; [NCBI, ExPASy, EBI, Israel, Japan]
Cool D.E., McGillivray R.T.A.;
"Characterization of the human blood coagulation factor XII gene. Intron/exon gene organization and analysis of the 5'-flanking region.";
J. Biol. Chem. 262:13662-13673(1987).

[2] SEQUENCE OF 4-615 FROM NUCLEIC ACID.
MEDLINE=86176794; PubMed=3754331; [NCBI, ExPASy, EBI, Israel, Japan]
Tripodi M., Citarella F., Guida S., Galeffi P., Fantoni A., Cortese R.;
"cDNA sequence coding for human coagulation factor XII (Hageman).";
Nucleic Acids Res. 14:3146-3146(1986).

[3] SEQUENCE OF 14-615 FROM NUCLEIC ACID.
MEDLINE=86033830; PubMed=3877053; [NCBI, ExPASy, EBI, Israel, Japan]
Cool D.E., Edgell C.-J.S., Louie G.V., Zoller M.J., Braver G.D., McGillivray R.T.A.;
"Characterization of human blood coagulation factor XII cDNA. Prediction of the primary structure of factor XII and the tertiary structure of beta-factor XIIa.";
J. Biol. Chem. 260:13666-13676(1985).

[4] SEQUENCE OF 146-615 FROM NUCLEIC ACID.
MEDLINE=86216049; PubMed=3011063; [NCBI, ExPASy, EBI, Israel, Japan]
Que B.G., Davie E.W.;
"Characterization of a cDNA coding for human factor XII (Hageman factor).";
Biochemistry 25:1525-1528(1986).

[5] SEQUENCE OF 20-379.
MEDLINE=85182674; PubMed=3886654; [NCBI, ExPASy, EBI, Israel, Japan]
McMullen B.A., Fujikawa K.;
"Amino acid sequence of the heavy chain of human alpha-factor XIIa (activated Hageman factor).";
J. Biol. Chem. 260:5328-5341(1985).

[6] SEQUENCE OF 354-362 AND 373-615.
MEDLINE=83291041; PubMed=6604055; [NCBI, ExPASy, EBI, Israel, Japan]
Fujikawa K., McMullen B.A.;
"Amino acid sequence of human beta-factor XIIa.";
J. Biol. Chem. 258:10924-10933(1983).

[7] SEQUENCE OF 561-615 FROM NUCLEIC ACID.
TISSUE=Blood;
MEDLINE=96133302; PubMed=8528215; [NCBI, ExPASy, EBI, Israel, Japan]
Schloesser M., Hofferbert S., Bartz U., Lutze G., Lammle B., Engel W.;
"The novel acceptor splice site mutation 11396(G-->A) in the factor XII gene causes a truncated transcript in cross-reacting material negative patients.";
Hum. Mol. Genet. 4:1235-1237(1995).

[8] VARIANT WASHINGTON DC.
MEDLINE=90046788; PubMed=2510163; [NCBI, ExPASy, EBI, Israel, Japan]
Miyata T., Kawabata S.-I., Iwanaga S., Takahashi I., Alving B., Saito H.;
"Coagulation factor XII (Hageman factor) Washington D.C.: inactive factor XIIa results from Cys-571-->Ser substitution.";
Proc. Natl. Acad. Sci. U.S.A. 86:8319-8322(1989).

[9] VARIANT LOCARNO.
MEDLINE=94325559; PubMed=8049433; [NCBI, ExPASy, EBI, Israel, Japan]
Hovinga J.K., Schaller J., Stricker H., Wuillemin W.A., Furlan M., Laemmle B.;
"Coagulation factor XII Locarno: the functional defect is caused by the amino acid substitution Arg-353-->Pro leading to loss of a kallikrein cleavage site.";
Blood 84:1173-1181(1994).

[10] CARBOHYDRATE-LINKAGE SITE THR-109.
MEDLINE=92184750; PubMed=1544894; [NCBI, ExPASy, EBI, Israel, Japan]
Harris R.J., Ling V.T., Spellman M.W.;
"O-linked fucose is present in the first epidermal growth factor domain of factor XII but not protein C.";
J. Biol. Chem. 267:5102-5107(1992).

Comments

- *FUNCTION*: FACTOR XII IS A SERUM GLYCOPROTEIN THAT PARTICIPATES IN THE INITIATION OF BLOOD COAGULATION, FIBRINOLYSIS, AND THE GENERATION OF BRADYKININ AND ANGIOTENSIN.
- *CATALYTIC ACTIVITY*: CLEAVES SELECTIVELY ARG-|-ILE BONDS AND ACTIVATES COAGULATION FACTORS VII AND XI.
- *PTM*: O- AND N-GLYCOSYLATED.

FIG. 11A

- *DISEASE*: DEFECTS IN F12 DO NOT CAUSE ANY CLINICAL SYMPTOMS. THE SOLE EFFECT IS THAT WHOLE-BLOOD CLOTTING TIME IS PROLONGED.
- *MISCELLANEOUS*: FACTOR XII, PREKALLIKREIN, AND HMW KININOGEN FORM A COMPLEX BOUND TO AN ANIONIC SURFACE. PREKALLIKREIN IS CLEAVED BY FACTOR XII TO FORM KALLIKREIN, WHICH THEN CLEAVES FACTOR XII FIRST TO ALPHA-FACTOR XIIA AND THEN TO BETA-FACTOR XIIA. ALPHA-FACTOR XIIA ACTIVATES FACTOR XI TO FACTOR XIA.
- *SIMILARITY*: CONTAINS 2 EGF-LIKE DOMAINS.
- *SIMILARITY*: CONTAINS 1 FIBRONECTIN TYPE I DOMAIN.
- *SIMILARITY*: CONTAINS 1 FIBRONECTIN TYPE II DOMAIN.
- *SIMILARITY*: CONTAINS 1 KRINGLE DOMAIN.
- *SIMILARITY*: BELONGS TO PEPTIDASE FAMILY S1; ALSO KNOWN AS THE TRYPSIN FAMILY.

Copyright

This SWISS-PROT entry is copyright. It is produced through a collaboration between the Swiss Institute of Bioinformatics and the EMBL outstation - the European Bioinformatics Institute. There are no restrictions on its use by non-profit institutions as long as its content is in no way modified and this statement is not removed. Usage by and for commercial entities requires a license agreement (See http://www.isb-sib.ch/announce/ or send an email to license@isb-sib.ch)

Cross-references

| | |
|---|---|
| EMBL | M31315; AAA70225.1; -.  [EMBL / GenBank / DDBJ] [CoDingSequence] |
| | M11723; AAA51986.1; -.  [EMBL / GenBank / DDBJ] [CoDingSequence] |
| | M17466; AAB59490.1; -.  [EMBL / GenBank / DDBJ] [CoDingSequence] |
| | M17464; AAB59490.1; JOINED. [EMBL / GenBank / DDBJ] [CoDingSequence] |
| | M17465; AAB59490.1; JOINED. [EMBL / GenBank / DDBJ] [CoDingSequence] |
| | M13147; AAA70224.1; -.  [EMBL / GenBank / DDBJ] [CoDingSequence] |
| | U71274; AAB51203.1; -.  [EMBL / GenBank / DDBJ] [CoDingSequence] |
| PIR | A29411; KFHU12. |
| HSSP | P00763: 1DPO. [HSSP ENTRY / PDB] |
| MEROPS | S01.211: -. |
| MIM | 234000 [NCBI / EBI]. |
| GeneCards | F12. |
| InterPro | IPR001314: Chymotrypsin. |
| | IPR000561: EGF-like. |
| | IPR000562: FN_Type_II. |
| | IPR000001: Kringle. |
| | IPR001254: Trypsin. |
| | IPR000083: fibronectin_type_I. |
| | Graphical view of domain structure. |
| Pfam | PF00008: EGF: 2. |
| | PF00039: fn1: 1. |
| | PF00040: fn2: 1. |
| | PF00051: kringle: 1. |
| | PF00089: trypsin: 1. |
| PRINTS | PR00013: FNTYPEII. |
| | PR00018: KRINGLE. |
| | PR00722: CHYMOTRYPSIN. |
| ProDom | PD000995: -: 1. |
| | [Domain structure / List of seq. sharing at least 1 domain]. |
| SMART | SM00181: EGF: 2. |
| | SM00058: FN1: 1. |
| | SM00059: FN2: 1. |
| | SM00130: KR: 1. |
| | SM00020: Tryp_SPc: 1. |
| PROSITE | PS00022: EGF_1: 2. |
| | PS01186: EGF_2: 1. |
| | PS01253: FIBRONECTIN_1: 1. |
| | PS00023: FIBRONECTIN_2: 1. |
| | PS00021: KRINGLE_1: 1. |
| | PS50070: KRINGLE_2: 1. |
| | PS50240: TRYPSIN_DOM: 1. |
| | PS00134: TRYPSIN_HIS: 1. |
| | PS00135: TRYPSIN_SER: 1. |
| BLOCKS | P00748. |

FIG. 11B

| | | | |
|---|---|---|---|
| DOMO | P00748. | | |
| ProtoMap | P00748. | | |
| PRESAGE | P00748. | | |
| DIP | P00748. | | |
| SWISS-2DPAGE | GET REGION ON 2D PAGE. | | |

Keywords

Glycoprotein; Blood coagulation; Plasma; Kringle; Serine protease; Hydrolase; Fibrinolysis; Signal; EGF-like domain; Repeat; Zymogen; Disease mutation.

Features

| Key | From | To | Length | Description |
|---|---|---|---|---|
| SIGNAL | 1 | 19 | 19 | |
| CHAIN | 20 | 372 | 353 | ALPHA-FACTOR XIIA HEAVY CHAIN. |
| CHAIN | 373 | 615 | 243 | ALPHA-FACTOR XIIA LIGHT CHAIN. |
| CHAIN | 354 | 362 | 9 | BETA-FACTOR XIIA PART 1. |
| CHAIN | 373 | 615 | 243 | BETA-FACTOR XIIA PART 2. |
| DOMAIN | 47 | 88 | 42 | FIBRONECTIN TYPE-II. |
| DOMAIN | 94 | 131 | 38 | EGF-LIKE 1. |
| DOMAIN | 133 | 173 | 41 | FIBRONECTIN TYPE-I. |
| DOMAIN | 174 | 210 | 37 | EGF-LIKE 2. |
| DOMAIN | 217 | 295 | 79 | KRINGLE. |
| DOMAIN | 296 | 349 | 54 | PRO-RICH. |
| DOMAIN | 373 | 615 | 243 | SERINE PROTEASE. |
| CARBOHYD | 109 | 109 | | O-LINKED (FUC). |
| CARBOHYD | 249 | 249 | | N-LINKED (GLCNAC...). |
| CARBOHYD | 299 | 299 | | O-LINKED (POTENTIAL). |
| CARBOHYD | 305 | 305 | | O-LINKED (POTENTIAL). |
| CARBOHYD | 308 | 308 | | O-LINKED (POTENTIAL). |
| CARBOHYD | 328 | 328 | | O-LINKED (POTENTIAL). |
| CARBOHYD | 329 | 329 | | O-LINKED (POTENTIAL). |
| CARBOHYD | 337 | 337 | | O-LINKED (POTENTIAL). |
| ACT_SITE | 412 | 412 | | CHARGE RELAY SYSTEM (BY SIMILARITY). |
| ACT_SITE | 461 | 461 | | CHARGE RELAY SYSTEM (BY SIMILARITY). |
| ACT_SITE | 563 | 563 | | CHARGE RELAY SYSTEM (BY SIMILARITY). |
| DISULFID | 98 | 110 | | BY SIMILARITY. |
| DISULFID | 104 | 119 | | BY SIMILARITY. |
| DISULFID | 121 | 130 | | BY SIMILARITY. |
| DISULFID | 135 | 163 | | BY SIMILARITY. |
| DISULFID | 161 | 170 | | BY SIMILARITY. |
| DISULFID | 178 | 189 | | BY SIMILARITY. |
| DISULFID | 183 | 198 | | BY SIMILARITY. |
| DISULFID | 200 | 209 | | BY SIMILARITY. |
| DISULFID | 217 | 295 | | BY SIMILARITY. |
| DISULFID | 238 | 277 | | BY SIMILARITY. |
| DISULFID | 266 | 290 | | BY SIMILARITY. |
| DISULFID | 359 | 486 | | BY SIMILARITY. |
| DISULFID | 397 | 413 | | BY SIMILARITY. |
| DISULFID | 405 | 475 | | BY SIMILARITY. |
| DISULFID | 436 | 439 | | BY SIMILARITY. |
| DISULFID | 500 | 569 | | BY SIMILARITY. |
| DISULFID | 532 | 548 | | BY SIMILARITY. |
| DISULFID | 559 | 590 | | BY SIMILARITY. |
| VARIANT | 372 | 372 | | R -> P (IN LOCARNO; INACTIVE). /FTId=VAR_006623. |
| VARIANT | 590 | 590 | | C -> S (IN WASHINGTON DC; INACTIVE). /FTId=VAR_006624. |
| CONFLICT | 333 | 333 | | P -> S (IN REF. 3). |

 Feature aligner

 Feature table viewer

FIG. 11C

CONFLICT    319    319        A -> G (IN REF. 4).
CONFLICT    589    589        G -> R (IN REF. 7).

Sequence information

Length: 615 AA [This is the length of the unprocessed precursor]
Molecular weight: 67818 Da [This is the MW of the unprocessed precursor]
CRC64: 1EB3D3EAA7BAAE9A [This is a checksum on the sequence]

```
         10         20         30         40         50         60
          |          |          |          |          |          |
MRALLLLGFL LVSLESTLSI PPWEAPKEHK YKAEEHTVVL TVTGEPCHFP FQYHRQLYHK 70         80         90        100        110        120
          |          |          |          |          |          |
CTHKGRPGPQ PWCATTPNFD QDQRWGYCLE PKKVKDHCSK HSPCQKGGTC VNMPSGPHCL 130        140        150        160        170        180
          |          |          |          |          |          |
CPQHLTGNHC QKEKCFEPQL LRFFHKNEIW YRTEQAAVAR CQCKGPDAHC QRLASQACRT 190        200        210        220        230        240
          |          |          |          |          |          |
NPCLHGGRCL EVEGHRLCHC PVGYTGPFCD VDTKASCYDG RGLSYRGLAR TTLSGAPCQP 250        260        270        280        290        300
          |          |          |          |          |          |
WASEATYRNV TAEQARNWGL GGHAFCRNPD NDIRPWCFVL NRDRLSWEYC DLAQCQTPTQ 310        320        330        340        350        360
          |          |          |          |          |          |
AAPPTPVSPR LHVPLMPAQP APPKPQPTTR TPPQSQTPGA LPAKREQPPS LTRNGPLSCG 370        380        390        400        410        420
          |          |          |          |          |          |
QRLRKSLSSM TRVVGGLVAL RGAHPYIAAL YWGHSFCAGS LIAPCWVLTA AHCLQDRPAP 430        440        450        460        470        480
          |          |          |          |          |          |
EDLTVVLGQE RRNHSCEPCQ TLAVRSYRLH EAFSPVSYQH DLALLRLQED ADGSCALLSP 490        500        510        520        530        540
          |          |          |          |          |          |
YVQPVCLPSG AARPSETTLC QVAGWGHQFE GAEEYASFLQ EAQVPFLSLE RCSAPDVHGS 550        560        570        580        590        600
          |          |          |          |          |          |
SILPGMLCAG FLEGGTDACQ GDSGGPLVCE DQAAERRLTL QGIISWGSGC GDRNKPGVYT

610
          |
DVAYYLAWIR EHTVS
```

P00748 in FASTA format

*View entry in original SWISS-PROT format*
*View entry in raw text format (no links)*
*Report form for errors updates in this SWISS-PROT entry*

 Direct BLAST submission at EMBnet-CH and CSCS (Switzerland)

 Direct BLAST submission at NCBI (Bethesda, USA)

 ScanProsite, ProfileScan

Tools Sequence analysis tools: ProtParam, ProtScale, Compute pI/Mw, PeptideMass, Dotlet (Java)

 Feature table viewer (Java)

 Search the SWISS-MODEL Repository

| ExPASy Home page | Site Map | Search ExPASy | Contact us | SWISS-PROT |

Hosted by SIB Switzerland Mirror sites: Australia Canada China Korea Taiwan

FIG. 11D

| ExPASy Home page | Site Map | Search ExPASy | Contact us | SWISS-PROT |

Hosted by SIB Switzerland Mirror sites: Australia Canada China Korea Taiwan

NiceProt View of SWISS-PROT: Q04756

Printer-friendly view | Quick BlastP search

[General] [Name and origin] [References] [Comments] [Cross-references] [Keywords] [Features] [Sequence] [Tools]

General information about the entry

| | |
|---|---|
| Entry name | HGFA_HUMAN |
| Primary accession number | Q04756 |
| Secondary accession number | Q14726 |
| Entered in SWISS-PROT in | Release 29, June 1994 |
| Sequence was last modified in | Release 29, June 1994 |
| Annotations were last modified in | Release 40, October 2000 |

Name and origin of the protein

| | |
|---|---|
| Protein name | HEPATOCYTE GROWTH FACTOR ACTIVATOR [Precursor] |
| Synonyms | EC 3.4.21.-<br>HGF ACTIVATOR<br>HGFA |
| Gene name | HGFAC |
| From | Homo sapiens (Human) [TaxID: 9606] |
| Taxonomy | Eukaryota; Metazoa; Chordata; Craniata; Vertebrata; Euteleostomi; Mammalia; Eutheria; Primates; Catarrhini; Hominidae; Homo. |

References

[1] SEQUENCE FROM NUCLEIC ACID, AND PARTIAL SEQUENCE.
TISSUE=Liver, and Serum;
MEDLINE=93252878; PubMed=7683665; [NCBI, ExPASy, EBI, Israel, Japan]
Miyazawa K., Shimomura T., Kitamura A., Kondo J., Morimoto Y., Kitamura N.;
"Molecular cloning and sequence analysis of the cDNA for a human serine protease responsible for activation of hepatocyte growth factor. Structural similarity of the protease precursor to blood coagulation factor XII.";
J. Biol. Chem. 268:10024-10028(1993).

[2] SEQUENCE OF 40-655 FROM NUCLEIC ACID.
Zhao S., Odell C.;
Submitted (FEB-1996) to the EMBL/GenBank/DDBJ databases.

Comments

- *FUNCTION*: ACTIVATES HEPATOCYTE GROWTH FACTOR (HGF) BY CONVERTING IT FROM A SINGLE CHAIN TO A HETERODIMERIC FORM.
- *SUBUNIT*: DIMER OF A SHORT CHAIN AND A LONG CHAIN LINKED BY A DISULFIDE BOND.
- *SUBCELLULAR LOCATION*: SECRETED AS AN INACTIVE SINGLE-CHAIN PRECURSOR AND IS THEN ACTIVATED TO A HETERODIMERIC FORM.
- *TISSUE SPECIFICITY*: LIVER.
- *SIMILARITY*: CONTAINS 2 EGF-LIKE DOMAINS.
- *SIMILARITY*: CONTAINS 1 FIBRONECTIN TYPE I DOMAIN.
- *SIMILARITY*: CONTAINS 1 FIBRONECTIN TYPE II DOMAIN.
- *SIMILARITY*: CONTAINS 1 KRINGLE DOMAIN.
- *SIMILARITY*: BELONGS TO PEPTIDASE FAMILY S1; ALSO KNOWN AS THE TRYPSIN FAMILY.
- *CAUTION*: IT IS UNCERTAIN WHETHER MET-1 IS THE INITIATOR.

Copyright

FIG. 12

This SWISS-PROT entry is copyright It is produced through a collaboration between the Swiss Institute of Bioinformatics and the EMBL outstation - the European Bioinformatics Institute There are no restrictions on its use by non-profit institutions as long as its content is in no way modified and this statement is not removed Usage by and for commercial entities requires a license agreement (See http //www isb-sib ch/announce/ or send an email to license@isb-sib ch)

Cross-references

| | |
|---|---|
| EMBL | D14012; BAA03113.1; -. [EMBL / GenBank / DDBJ] [CoDingSequence] |
| | Z69923; CAA93803.1; -. [EMBL / GenBank / DDBJ] [CoDingSequence] |
| PIR | A46688; A46688. |
| MIM | 604552 [NCBI / EBI]. |
| GeneCards | HGFAC. |
| HSSP | P00763; IDPO. [HSSP ENTRY / PDB] |
| MEROPS | S01.228; -. |
| InterPro | IPR001314: Chymotrypsin. |
| | IPR000561: EGF-like. |
| | IPR000742: EGF_2. |
| | IPR000562: FN_Type_II. |
| | IPR000001: Kringle. |
| | IPR001254: Trypsin. |
| | IPR000083: fibronectin_type_I. |
| | Graphical view of domain structure. |
| Pfam | PF00008; EGF; 2. |
| | PF00039; fn1; 1. |
| | PF00040; fn2; 1. |
| | PF00051; kringle; 1. |
| | PF00089; trypsin; 1. |
| PRINTS | PR00013: FNTYPEII. |
| | PR00018: KRINGLE. |
| | PR00722: CHYMOTRYPSIN. |
| ProDom | PD000995; -; 1. |
| | [Domain structure / List of seq. sharing at least 1 domain]. |
| SMART | SM00181: EGF; 2. |
| | SM00058: FN1; 1. |
| | SM00059: FN2; 1. |
| | SM00130: KR; 1. |
| | SM00020: Tryp_SPc; 1. |
| PROSITE | PS00022; EGF_1; 2. |
| | PS01186; EGF_2; 1. |
| | PS01253; FIBRONECTIN_1; 1. |
| | PS00023; FIBRONECTIN_2; 1. |
| | PS00021; KRINGLE_1; 1. |
| | PS50070; KRINGLE_2; 1. |
| | PS50240; TRYPSIN_DOM; 1. |
| | PS00134; TRYPSIN_HIS; 1. |
| | PS00135; TRYPSIN_SER; 1. |
| BLOCKS | Q04756. |
| DOMO | Q04756. |
| ProtoMap | Q04756. |
| PRESAGE | Q04756. |
| DIP | Q04756. |
| SWISS-2DPAGE | GET REGION ON 2D PAGE. |

Keywords

Hydrolase; Glycoprotein; Plasma; Serine protease; Kringle; Signal; EGF-like domain; Repeat; Zymogen.

Features

FIG. 12A

| Key | From | To | Length | Description |
|---|---|---|---|---|
| SIGNAL | 1 | 30 | 30 | |
| PROPEP | 31 | 372 | 342 | CLEAVED IN ACTIVE FORM. |
| CHAIN | 373 | 407 | 35 | HEPATOCYTE GROWTH FACTOR ACTIVATOR SHORT CHAIN. |
| CHAIN | 408 | 655 | 248 | HEPATOCYTE GROWTH FACTOR ACTIVATOR LONG CHAIN. |
| DOMAIN | 108 | 148 | 41 | FIBRONECTIN TYPE-II. |
| DOMAIN | 160 | 198 | 39 | EGF-LIKE 1. |
| DOMAIN | 200 | 240 | 41 | FIBRONECTIN TYPE-I. |
| DOMAIN | 241 | 279 | 39 | EGF-LIKE 2. |
| DOMAIN | 286 | 367 | 82 | KRINGLE. |
| DOMAIN | 408 | 655 | 248 | SERINE PROTEASE. |
| ACT_SITE | 447 | 447 | | CHARGE RELAY SYSTEM (BY SIMILARITY). |
| ACT_SITE | 497 | 497 | | CHARGE RELAY SYSTEM (BY SIMILARITY). |
| ACT_SITE | 598 | 598 | | CHARGE RELAY SYSTEM (BY SIMILARITY). |
| DISULFID | 106 | 133 | | BY SIMILARITY. |
| DISULFID | 122 | 148 | | BY SIMILARITY. |
| DISULFID | 164 | 175 | | BY SIMILARITY. |
| DISULFID | 169 | 186 | | BY SIMILARITY. |
| DISULFID | 188 | 197 | | BY SIMILARITY. |
| DISULFID | 202 | 230 | | BY SIMILARITY. |
| DISULFID | 228 | 237 | | BY SIMILARITY. |
| DISULFID | 245 | 256 | | BY SIMILARITY. |
| DISULFID | 250 | 267 | | BY SIMILARITY. |
| DISULFID | 269 | 276 | | BY SIMILARITY. |
| DISULFID | 286 | 367 | | BY SIMILARITY. |
| DISULFID | 307 | 349 | | BY SIMILARITY. |
| DISULFID | 338 | 362 | | BY SIMILARITY. |
| DISULFID | 394 | 521 | | INTRACHAIN (BY SIMILARITY). |
| DISULFID | 432 | 448 | | BY SIMILARITY. |
| DISULFID | 440 | 510 | | BY SIMILARITY. |
| DISULFID | 535 | 604 | | BY SIMILARITY. |
| DISULFID | 567 | 583 | | BY SIMILARITY. |
| DISULFID | 594 | 622 | | BY SIMILARITY. |
| CARBOHYD | 48 | 48 | | N-LINKED (GLCNAC...) (POTENTIAL). |
| CARBOHYD | 290 | 290 | | N-LINKED (GLCNAC...) (POTENTIAL). |
| CARBOHYD | 468 | 468 | | N-LINKED (GLCNAC...) (POTENTIAL). |
| CARBOHYD | 492 | 492 | | N-LINKED (GLCNAC...) (POTENTIAL). |
| CARBOHYD | 546 | 546 | | N-LINKED (GLCNAC...) (POTENTIAL). |
| CONFLICT | 644 | 644 | | R -> Q (IN REF. 2). |

 Feature aligner

 Feature table viewer

Sequence information

Length: 655 AA [This is the length of the unprocessed precursor]

Molecular weight: 70681 Da [This is the MW of the unprocessed precursor]

CRC64: 2CF72F1E1B862ED7 [This is a checksum on the sequence]

FIG. 12B

```
         10          20          30          40          50          60
         |           |           |           |           |           |
MGRWAWVPSP WPPPGLGPFL LLLLLLLLLP RGFQPQPGGN RTESPEPNAT ATPAIPTILV 70          80          90         100         110         120
         |           |           |           |           |           |
TSVTSETPAT SAPEAEGPQS GGLPPPPRAV PSSSSPQAQA LTEDGRPCRF PFRYGGRMLH 130         140         150         160         170         180
         |           |           |           |           |           |
ACTSEGSAHR KWCATTHNYD RDRAWGYCVE ATPPPGGPAA LDPCASGPCL NGGSCSNTQD 190         200         210         220         230         240
         |           |           |           |           |           |
PQSYHCSCPR AFTGKDCGTE KCFDETRYEY LEGGDRWARV RQGHVEQCEC FGGRTWCEGT 250         260         270         280         290         300
         |           |           |           |           |           |
RHTACLSSPC LNGGTCHLIV ATGTTVCACP PGFAGRLCNI EPDERCFLGN GTGYRGVAST 310         320         330         340         350         360
         |           |           |           |           |           |
SASGLSCLAW NSDLLYQELH VDSVGAAALL GLGPHAYCRN PDNDERPWCY VVKDSALSWE 370         380         390         400         410         420
         |           |           |           |           |           |
YCRLEACESL TRVQLSPDLL ATLPEPASPG RQACGRRHKK RTFLRPRIIG GSSSLPGSHP 430         440         450         460         470         480
         |           |           |           |           |           |
WLAAIYIGDS FCAGSLVHTC WVVSAAHCFS HSPPRDSVSV VLGQHFFNRT TDVTQTFGIE 490         500         510         520         530         540
         |           |           |           |           |           |
KYIPYTLYSV FNPSDHDLVL IRLKKKGDRC ATRSQFVQPI CLPEPGSTFP AGHKCQIAGW 550         560         570         580         590         600
         |           |           |           |           |           |
GHLDENVSGY SSSLREALVP LVADHKCSSP EVYGADISPN MLCAGYFDCK SDACQGDSGG 610         620         630         640         650
         |           |           |           |           |
PLACEKNGVA YLYGIISWGD GCGRLHKPGV YTRVANYVDW INDRIRPPRR LVAPS
```

Q04756 in FASTA format

*View entry in original SWISS-PROT format*
*View entry in raw text format (no links)*
*Report form for errors/updates in this SWISS-PROT entry*

 Direct BLAST submission at EMBnet-CH and CSCS (Switzerland)

 Direct BLAST submission at NCBI (Bethesda, USA)

 ScanProsite, ProfileScan

 Tools Sequence analysis tools: ProtParam, ProtScale, Compute pI/Mw, PeptideMass, Dotlet (Java)

 Feature table viewer (Java)

 Search the SWISS-MODEL Repository

| ExPASy Home page | Site Map | Search ExPASy | Contact us | SWISS-PROT |

Hosted by SIB Switzerland | Mirror sites: Australia Canada China Korea Taiwan

FIG. 12C

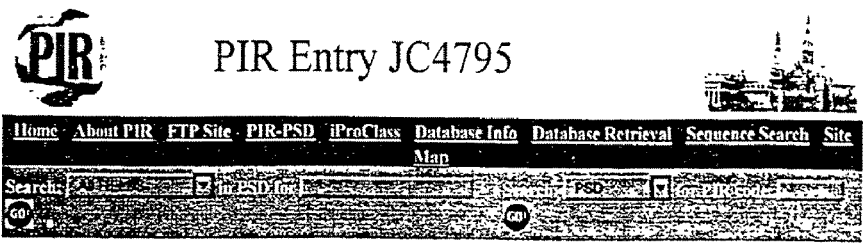

in the PIR1 section of the Protein Sequence Database, release 68.03, 24-May-2001, assembled and annotated by the PIR-International.
Copyright © 2000 PIR-International.

Submission Form    create a   BLAST (at PIR)    ▼ submission form for JC4795

Annotation || Sequence || Composition Table || Download: (CODATA || FASTA || XML)

```
ENTRY             JC4795   #type complete
TITLE             plasma hyaluronan-binding protein precursor - human
ALTERNATE_NAMES   hepatocyte growth factor activator-like protein; PHBP
CONTAINS          serine proteinase (EC 3.4.21.-)
ORGANISM          #formal_name Homo sapiens #common_name man
   #cross-references taxon:9606
DATE              15-Oct-1995 #sequence_revision 16-Aug-1996 #text_change
                  16-Jul-1999
ACCESSIONS        JC4795
REFERENCE         JC4795
   #authors       Choi-Miura, N.H.; Tobe, T.; Sumiya, J.; Nakano, Y.; Sano,
                  Y.; Mazda, T.; Tomita, M.
   #journal       J. Biochem. (1996) 119:1157-1165
   #title         Purification and characterization of a novel
                  hyaluronan-binding protein (PHBP) from human plasma: It
                  has three EGF, a kringle and a serine protease domain,
                  similar to hepatocyte growth factor activator.
   #cross-references MUID:96425001
   #accession     JC4795
     ##molecule_type mRNA
     ##residues 1-560 ##label CHO
     ##cross-references GB:S83182; NID:g1836158; PIDN:AAB46909.1;
           PID:g1836159
     ##experimental_source plasma
     ##note parts of this sequence, including the amino ends of the
            mature chains, were determined by protein sequencing
GENETICS
   #gene          GDB:HABP2; HABP; PHBP; HGFAL
     ##cross-references GDB:4573962
COMPLEX           a disulfide-bonded heterodimer of chains produced from the
                  same precursor; the catalytic chain is degraded to a 17K
                  chain lacking the active site serine residue
CLASSIFICATION    #superfamily plasma hyaluronan-binding protein; EGF
                  homology; kringle homology; trypsin homology
KEYWORDS          chondroitin sulfate proteoglycan; glycoprotein; growth
                  factor; hyaluronic acid; hydrolase; kringle; plasma;
                  serine proteinase
FEATURE
   1-23                    #domain signal sequence #status predicted #label
                           SIG\
   24-313                  #product plasma hyaluronan-binding protein, 50K
                           chain #status predicted #label 50F\
   77-108                  #domain EGF homology #label EG1\
   115-147                 #domain EGF homology #label EG2\
   154-187                 #domain EGF homology #label EG3\
   194-276                 #domain kringle homology #label KRI\
   314-550                 #domain trypsin homology #label TRY\
   314-516                 #product plasma hyaluronan-binding protein,
                           catalytic chain #status predicted #label CAT\
   54,207                  #binding site carbohydrate (Asn) (covalent)
                           #status predicted\
   77-88,82-97,99-108,
   115-125,120-136,
   138-147,154-165,
   159-176,178-187,
   194-276,215-257,
   246-271,301-435,
   347-363,355-424,
```

FIG. 13

```
447-515,477-493,
505-533              #disulfide bonds #status predicted\
362,405,509          #active site His, Asp, Ser #status predicted
SUMMARY              #length 560 #molecular_weight 62671

SEQUENCE
              5         10        15        20        25        30
  1  M F A R M S D L H V L L L M A L V G K T A C G F S L M S L L
 31  E S L D P D W T P D Q Y D Y S Y E D Y N Q E E N T S S T L T
 61  H A E N P D W Y Y T E D Q A D P C Q P N P C E H G G D C L V
 91  H G S T F T C S C L A P F S G N K C Q K V Q N T C K D N P C
121  G R G Q C L I T Q S P P Y Y R C V C K H P Y T G P S C S Q V
151  V P V C R P N P C Q N G A T C S R H K R R S K F T C A C P D
181  Q F K G K F C E I G S D D C Y V G D G Y S Y R G K M N R T V
211  N Q H A C L Y W N S H L L L Q E N Y N M F M E D A E T H G I
241  G E H N F C R N P D A D E K P W C F I K V T N D K V K W E Y
271  C D V S A C S A Q D V A Y P E E S P T E P S T K L P G F D S
301  C G K T E I A E R K I K R I Y G G F R S T A G K H P W Q A S
331  L Q S S L P L T I S M P Q G H F C G G A L I H P C W V L T A
361  A H C T D I K T R H L K V V L G D Q D L K K E E F H E Q S F
391  R V E K I F K Y S H Y N E R D E I P H N D I A L L K L K P V
421  D G H C A L E S K Y V K T V C L P D G S F P S G S E C H I S
451  G W G V T E T G K G S R Q L L D A K V K L I A N T L C N S R
481  Q L Y D H M I D D S M I C A G N L Q K P G Q D T C Q G D S G
511  G P L T C E K D G T Y Y V Y G I V S W G L E C G K R P G V Y
541  T Q V T K F L N W I K A T I K S E S G F
```

Enzyme Links for JC4795:
    EC-IUBMB: EC 3.4.21.-
    KEGG: EC 3.4.21.-
    BRENDA: EC 3.4.21.-
    WIT: EC 3.4.21.-
    MetaCyc: EC 3.4.21.-

Associated Alignments:
    DA0704 EGF homology - Type A
    DA0705 EGF homology - Type B
    DA1052 kringle homology - selected coagulation factors
    DA1082 trypsin homology

**Link to *i*ProClass** (Superfamily classification and Alignment):
    *i*ProClass Report for JC4795 at PIR.

FIG. 13A

STABILIZED PROTEINS WITH ENGINEERED DISULFIDE BONDS

This application is a divisional of application Ser. No. 10/172,712, filed Jun. 14, 2002, now U.S. Pat. No. 7,205,278, which claims priority to and benefit of U.S. provisional application No. 60/298,578, filed Jun. 14, 2001, each of which is incorporated herein by reference in their entireties.

This invention was made with the assistance of funds provided by the Government of the United States. The government may own certain rights in the present invention, pursuant to grants from the National Institutes of Health, grant numbers R01HL21544, R37HL52246, T32HL07695 and P01GM48495.

FIELD OF THE INVENTION

The present invention relates to methods of introducing one or more cysteine residues into a polypeptide which permit the stabilization of the polypeptide by formation of at least one bond, preferably a disulfide bond, between different domains of the polypeptide. The invention also relates to polypeptides containing such introduced cysteine residue(s), nucleic acids encoding such polypeptides and pharmaceutical compositions comprising such polypeptides or nucleic acids. The invention also relates to vectors, viral particles and host cells containing such nucleic acids, and methods of using them to produce the polypeptides of the invention.

BACKGROUND OF THE INVENTION

Many polypeptides are known which are the expression product of a single gene. A number of these polypeptides are originally synthesized as a single polypeptide chain, but contain multiple, independently folded domains, which are subject to limited proteolysis (or proteolytic cleavage(s)) in vivo that may result in separation of domains due to dissociation of the cleavage products. Proteolysis resulting in the separation of domains has been shown to alter the stability and/or enzymatic or functional activities of a variety of these proteins. Examples of these proteins include plasma proteins, such as those involved in blood coagulation.

As known in the art, blood clotting begins when platelets adhere to the wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protease precursor is converted to a protease that cleaves the next protein precursor in the series. Cofactors are required at most of the steps. In its active form, the protein factor VIII is a cofactor that is required for the activation of factor X by the protease, activated factor IX.

Factor VIII can be activated to factor VIIIa (where "a" indicates "activated") proteolytically by thrombin or factor Xa. In combination with calcium and phospholipid, factor VIIIa makes factor IXa a more efficient activator of factor X by a mechanism which is not fully understood.

People deficient in factor VIII or having antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of factor VIII, which will restore the blood's normal clotting ability if administered with sufficient frequency and concentration.

Several preparations of human plasma-derived or recombinant factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII.

Hemophiliacs require daily replacement of factor VIII to prevent the deforming hemophilic arthropathy that occurs after many years of recurrent hemorrhages into the joints. However, supplies of factor VIII concentrates have never been plentiful enough for treating hemophiliacs adequately because of problems in commercial production and therapeutic use. For example, the commonly used plasma-derived factor VIII is difficult to isolate and purify, is immunogenic, and requires treatment to remove the risk of infectivity from AIDS and hepatitis viruses. Porcine factor VIII may also present an alternative, however a limitation of porcine factor VIII is the development of inhibitory antibodies to it after one or more infusions.

Activated factor VIII (FVIIIa) is thermodynamically unstable under physiological conditions due to the tendency of the A2 domain to dissociate from the rest of the complex. In other words, activated FVIII spontaneously becomes inactive. If this dissociation could be prevented in pharmacological preparations of FVIII or FVIIIa, administration that is less frequent and/or of lower concentration, could be realized. This could result in a number of benefits such as cost savings, decreased use of medical personnel, and improved lifestyle for hemophiliacs.

Another plasma protein besides factor VIII is prothrombin. As part of the coagulation cascade, prothrombin is converted to thrombin by the action of the prothrombinase complex (FXa, FVa, and $Ca^{2+}$). In human prothrombin, this conversion involves cleavages at Arg271 and Arg284, between the F2 domain and the thrombin A chain, and at Arg320, between the A and B chains (human numbering system). In vivo, prothrombinase first cleaves prothrombin at Arg320, producing meizothrombin. Free meizothrombin is an unstable intermediate, and autolysis at the Arg155-Ser156 bond rapidly removes the F1 domain to generate meizothrombin (des F1), which slowly converts to thrombin via the cleavages at Arg271 and Arg284. In the presence of thrombomodulin and phosphatidylserine/phosphatidylcholine phospholipid vesicles (PCPS), meizothrombin and meizothrombin (des F1) are better activators of protein C than thrombin (41, 42).

An additional plasma protein is factor V. Human coagulation factor V (FV) is a 330,000 MW protein, which is composed of six domains of three types in the order A1-A2-B-A3-C1-C2 (4). FV is cleaved by thrombin to remove most of the B domain and produce activated FV (FVa). Human FVa is composed of a heavy chain (A1-A2, residues 1-709) and a light chain (A3-C1-C2, residues 1546-2196), which form a non-covalent complex (5). FVa is the nonenzymatic cofactor for factor Xa (FXa) in the prothrombinase complex, which converts prothrombin to thrombin, in the presence of negatively charged phospholipids (6). Inactivation of FVa is a complex process involving APC (activated Protein C) cleavages of FVa at Arg506, Arg306 and Arg679. Cleavage at Arg506 is faster than cleavage at Arg306, and it only partially inactivates FVa while cleavage at Arg306 completely inactivates FVa and causes dissociation of the A2 domain fragments (7-10). Fully inactive FVa loses the ability to bind to FXa (11).

Still another plasma protein is factor XII. Human FXII is a single-chain protein with a MW of 76,000 and 596 amino acids. It contains, in order from N-terminus to C-terminus fibronectin type II domain, EGF domain, fibronectin type I domain, EGF domain, Kringle domain, trypsin-like serine protease domain. At least two forms of activated factor XII (FXIIa) exist. αFXIIa is formed by cleavage of the bond following Arg353, generating a two chain molecule comprised of a heavy chain (353 residues) and a light chain (243 residues) held together by a disulfide bond. Further cleavage results in FXIIa (FXIIa fragment). This is the result of cleavage at Arg334 and Arg343, resulting in two polypeptide chains (9 and 243 residues) held together by a disulfide bond (43, 44). The bulk of the N-terminal heavy chain fragment is no longer associated. Negative surface/membrane binding is mediated through this heavy chain so the resulting FXIIa fragment no longer binds to surfaces but it is still catalytically active.

The protein HGFA (hepatocyte growth factor activator) has the same domain structure as FXII (45) and is also activated by proteolytic cleavage, in this case, only one cleavage by thrombin at Arg407 (46), homologous to Arg353 in FXII. But further cleavage by kallikrein at Arg372 also results in release of the N-terminal heavy chain, which, as in FXII, is involved in surface binding (47). As known in the art, HGFA activates hepatocyte growth factor (HGF) within injured tissues where HGF plays roles in tissue repair via a mitogenic activity towards a variety of cell types.

Another FXII-like polypeptide is known by two names: PHBP (plasma hyaluronin binding protein) (48) and FVII activating protease (49). PHBP is a serine protease and is homologous to HGFA though the domain structure is not exactly the same (49, 50). This protein activates FVII, uPA, and tPA in experimental systems, but the physiological role has not been established (49, 50).

SUMMARY OF THE INVENTION

According to embodiments of the present invention, one may engineer into a polypeptide one or more cysteine residues to permit formation of a bond, such as a disulfide bond, between two or more of the polypeptide's domains. Placement of such disulfide bond(s) allows one to achieve results such as polypeptide stabilization. Such stabilization can result in the prolonged retention of desired activities of the undissociated polypeptide or the avoidance of undesired activities of the disassociated polypeptide.

Preferred polypeptides useful in the invention are those which are synthesized in nature as a single polypeptide chain, generally as the expression product of a single gene, and which contain multiple, independently folded domains which are subject to limited proteolysis that may result in separation of domains due to dissociation. Examples of such polypeptides include plasma proteins, including hepatocyte growth factor activator and plasma hyaluronin binding protein, as well as blood coagulation factors, such as Factor VIII, Factor V, Factor XII and prothrombin.

Mutant polypeptides of the invention (i.e., those polypeptides into which one or more cysteine(s) have been introduced) include not only those in which the domains which are linked are synthesized from a single nucleic acid sequence (e.g., from a single gene, cDNA, or synthetic or semi-synthetic coding sequence), but also those in which the domains which are linked are synthesized from distinct (or separate) nucleic acid sequences (e.g., from sequences encoding polypeptides comprising each of the linked domains, which sequences may or may not be present on a contiguous nucleic acid molecule). In the latter case, the domains may be joined together after synthesis, either in vivo or in vitro.

Preferred mutant polypeptides of the invention are those which have increased stability and/or retain desirable enzymatic or functional activities for a longer period of time as compared to the corresponding unmutated polypeptide.

One aspect of the invention relates to a method of stabilizing a polypeptide which is the product of a single gene in nature by introducing one or more cysteines comprising the steps of: (a) obtaining or creating a three-dimensional structure of the polypeptide; (b) predicting one or more sites for the introduction of one or more cysteines based on the three dimensional structure; and (c) creating one or more mutants of said polypeptide by introducing one or more cysteines at one or more of the predicted sites; wherein the introduction of said one or more cysteines permits the formation of at least one intramolecular, interdomain disulfide bridge which increases the stability of the mutant polypeptide as compared to that of the polypeptide which does not contain said introduced one or more cysteines.

Another aspect of the invention relates to a polypeptide which is the product of a single gene in nature which has been mutated by introducing at least one cysteine, wherein the introduction of said cysteine permits the formation of at least one intramolecular, interdomain disulfide bridge with another cysteine, which increases the stability of the mutant polypeptide as compared to that of the polypeptide which does not contain said introduced cysteine.

Another aspect of the invention relates to compositions comprising the polypeptides of the invention, including pharmaceutical compositions comprising the polypeptides of the invention and a pharmaceutically acceptable carrier.

The invention also relates to nucleic acids coding for the polypeptides of the invention, including vectors containing such nucleic acids. The invention also relates to viral particles containing such nucleic acids and/or vectors. The invention also relates to host cells containing such nucleic acids, vectors, and viral particles. The invention also relates to compositions (including pharmaceutical compositions) which contain the nucleic acids, vectors, viral particles and/or host cells of the invention.

The invention also relates to methods of treating individuals with the polypeptides, nucleic acids, vectors, viral particles or host cells of the invention and/or pharmaceutical compositions thereof.

BRIEF DESCRIPTION OF THE DRAWINGS

FIG. 1A is a schematic of the primary sequence of FVΔB (B-domain deleted human Factor V) with the locations of the different domains indicated. FIG. 1B is a schematic showing activated FVΔB (FVa), a heterodimer of the N-terminal heavy chain and the C-terminal light chain associated in the presence of $Ca^{2+}$ ions. Arrows indicate sites of cleavage in FVa by APC. FIG. 1C is a schematic showing the cleavage fragments produced upon inactivation of FVa (FVai) by APC, and further shows the sites of cysteine mutations that did (His609-Glu1691) and did not (Leu238-Gln590) result in disulfide bond formation.

FIG. 7 is a description of the accession numbers and related references used as a source for the amino acid sequences, with notes concerning the numbering system for Factor VIII, Factor V, Prothrombin, Factor XII, HGFA and PHBP mutants described in the examples herein.

FIG. 8. Webpages from SwissProt Accession #P00451 containing amino acid sequence of human Factor VIII and related information.

FIG. 9. Webpages from SwissProt Accession #P12259 containing amino acid sequence of human Factor V and related information.

FIG. 10. Webpages from SwissProt Accession #P00734 containing amino acid sequence of human Prothrombin and related information.

FIG. 11. Webpages from SwissProt Accession #P00748 containing amino acid sequence of human Factor XII and related information.

FIG. 12. Webpages from SwissProt Accession #Q04756 containing amino acid sequence of human HGFA and related information.

FIG. 13. Webpages from PIR Accession #JC4795 containing amino acid sequence of human PHBP and related information.

DETAILED DESCRIPTION OF THE INVENTION

Figure 1:
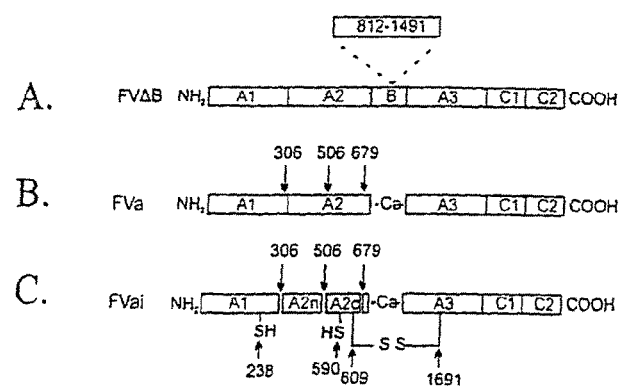
FIG. 1 is a schematic of recombinant B domain-deleted FV molecules.
Figure 2:
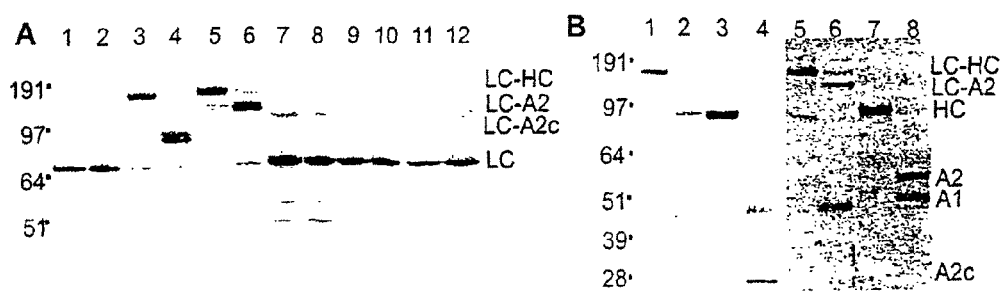
FIG. 2. Immunoblots of various FVa and FVai mutants. (A) Immunoblot developed with an anti-FV light chain monoclonal antibody. Samples in lanes 1 through 6 were not reduced and those in lanes 7 through 12 were reduced. Lanes 1 and 7, 2183A-FVa; lanes 2 and 8, 2183A-FVai; lanes 3 and 9, A2-SS-A3-FVa; lanes 4 and 10, A2-SS-A3-FVai; lanes 5 and 11, Q506-A2-SS-A3-FVa; lanes 6 and 12, Q506-A2-SS- A3-FVai. (B) Immunoblots developed with anti-FV heavy chain polyclonal antibodies. Lane 1, non-reduced A2-SS-A3-FVa; lane 2, non-reduced A2-SS-A3-FVai; lane 3, reduced A2-SS-A3-FVa; lane 4, reduced A2-SS-A3-FVai; lane 5, non-reduced Q506-A2-SS-A3-FVa; lane 6, non-reduced Q506-A2-SS-A3-FVai; lane 7, reduced Q506-A2-SS-A3-FVa; lane 8, reduced Q506-A2-SS-A3-FVai. Band positions for cross-linked and non cross-linked fragments are indicated on the right side of each blot. LC=light chain, HC=heavy chain, A1=A1 domain, A2=A2 domain, A2c=C-terminal fragment of the A2 domain (residues 507-679). Molecular weight marker positions (kDa, Novex SeeBlue standards) are indicated on the left side.

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

General Procedure

According to embodiments of the present invention, one may engineer into a polypeptide, such as the polypeptide product of a single gene, one or more cysteine residues which permit the formation of a disulfide bond between two or more of the polypeptide's domains. Placement of such cysteine(s), with their resultant, disulfide bonds allows one to achieve results such as polypeptide stabilization. It is noted that, in some embodiments, the present invention may also be used to place a disulfide bond within a single domain of a polypeptide, between two different polypeptides, and the like.

As a first step, a structure of the polypeptide of interest is obtained or created. This may be an x-ray crystal structure, an NMR-derived structure, a three-dimensional structure based on homology modeling, neutron diffraction or the like.

Next, an algorithm which predicts sites for the introduction of disulfide bridges by placement of cysteines may be applied to a structure of the polypeptide of interest. This may be done, for example, by using the computer program MODIP which employs the algorithm of Sowdhamini (19). MODIP predicts sites for the introduction of disulfide bridges, and provides grades (A, B, C) for each prediction. Grade A sites are those predicted to be most optimal for the establishment of disulfide bridges, while grade B and grade C sites are progressively less ideal. Said differently, grade A disulfide bridges satisfy defined stereochemical criteria while grade C disulfides satisfy fewer of the stereochemical criteria. It is specifically noted that other algorithms and/or computer programs, such as the algorithm of Pabo (18) or Hazes (56) may be used. In other embodiments, predictions for the introduction cysteines in order to establish disulfide bridges may be made by other methods such as by visual inspection.

Of the sites predicted, one may choose a number of the most ideal sites for further investigation.

Visual inspection of the chosen sites may be performed using computational graphics analysis. Based on this visual inspection, certain sites may be eliminated from further consideration. For each of the chosen sites remaining in consideration after visual inspection, a modified structural model including a disulfide bond at the chosen site may be created. This may be done using computer programs, such as the Xfit computer program, for example, with refinement being provided by another computer program, for example, the X-PLOR computer program using the Charm22 all atoms force field.

After refinement, the modeled disulfide bonds may be analyzed for optimal disulfide geometry. Those sites with the best geometry for formation of disulfide bonds, and perhaps the lowest Van Der Waals gas phase energies, may be chosen for attempts to introduce one or more cysteine residues which permit the formation of one or more disulfide bonds. Cysteine residues may be introduced into a polypeptide using techniques well known in the art such as, for example, recombinant techniques such as site directed mutagenesis of a nucleic acid encoding the polypeptide of interest. Nucleic acids encoding polypeptides of the invention may also be made by synthetic or semi-synthetic methods. For example, the nucleic acid encoding the polypeptide of the invention can be synthesized directly using overlapping synthetic deoxynucleotides (see, e.g., Edge et al., Nature 292:756 (1981); Nambair et al., Science 223:1299 (1984); Jay et al., J. Biol. Chem. 259:6311 (1984); or by using a combination of polymerase chain reaction generated DNAs or cDNAs and synthesized oligonucleotides. The nucleic acids of the invention can be present in, or inserted into an expression vector containing an appropriate promoter region operably linked to the sequence encoding the polypeptide of the invention and an appropriate terminator signal. Afterwards, vector purification, and transfection procedures known in the art may be performed. Next, stable clones may be selected and collected using methods known in the art. Produced polypeptides may then be quantified by activity and by immunoblots so as to confirm the proper placement of the disulfide bond(s) in the polypeptide of interest and the yields thereof.

Nucleic acids encoding the polypeptides of the invention can be expressed in the native host cell or organism or in a different cell or organism. The nucleic acids can be introduced into a vector such as a plasmid, cosmid, phage, virus or mini-chromosome and inserted into a host cell or organism by methods well known in the art. In general, the nucleic acids or vectors containing these nucleic acids can be utilized in any cell, either eukaryotic or prokaryotic, including mammalian cells (e.g., human (e.g., K293, HeLa), monkey (e.g., COS), rabbit (e.g., rabbit reticulocytes), rat, hamster (e.g., CHO and baby hamster kidney cells) or mouse cells (e.g., L cells), plant cells, yeast cells, insect cells or bacterial cells (e.g., *E. coli*). The vectors which can be utilized to clone and/or express these nucleic acids encoding the polypeptide are the vectors which are capable of replicating and/or expressing the nucleic acids in the host cell in which the nucleic acids are desired to be replicated and/or expressed. See, e.g., F. Ausubel et al., *Current Protocols in Molecular Biology*, Greene Publishing Associates and Wiley-Interscience (1992) and Sambrook et al. (1989) for examples of appropriate vectors for various types of host cells. The native promoters for such genes can be replaced with strong promoters compatible with the host into which the nucleic acid encoding the polypeptide of the invention is inserted. These promoters may be inducible. The host cells containing these nucleic acids can be used to express large amounts of the polypeptides of the invention useful in enzyme preparations, pharmaceuticals, diagnostic reagents, and therapeutics. The polypeptides of the invention may also be made in transgenic plants or animals using methods known in the art.

If the genes which naturally encode the polypeptides of the invention contain inhibitory/instability regions (see, e.g., WO 93/20212) less-preferred codons may be altered to more-preferred codons. If desired, however, (e.g., to make an AT-rich region more GC-rich), more-preferred codons can be altered to less-preferred codons. Optionally, only the most rarely used codons (identified from published codon usage tables, such as in T. Maruyama et al., Nucl. Acids Res. 14(Supp):r151-197 (1986)) may be replaced with preferred codons, or alternatively, most or all of the rare codons can be replaced with preferred codons. Generally, the choice of preferred codons to use will depend on the codon usage of the host cell in which the altered gene is to be expressed. Note, however, that the substitution of more-preferred codons with less-preferred codons is also functional.

As noted above, coding sequences are chosen on the basis of the genetic code and, preferably on the preferred codon usage in the host cell or organism in which the nucleic acid encoding a polypeptide of this invention is to be expressed. In a number of cases the preferred codon usage of a particular host or expression system can be ascertained from available references (see, e.g., T. Maruyama et al., Nucl. Acids Res. 14(Supp):r151-197 (1986), in which the number of times the codon appears in genes per 1000 codons is listed in parentheses next to the codon), or can be ascertained by other methods (see, e.g., U.S. Pat. No. 5,082,767 entitled "Codon Pair Utilization", issued to G. W. Hatfield et al. on Jan. 21, 1992). Preferably, sequences will be chosen to optimize transcription and translation as well as mRNA stability so as to ultimately increase the amount of polypeptide produced. Selection of codons is thus, for example, guided by the preferred use of codons by the host cell and/or the need to provide for desired restriction endonuclease sites and could also be guided by a desire to avoid potential secondary structure constraints in the encoded mRNA transcript. Potential secondary structure constraints can be identified by the use of computer programs such as the one described in M. Zucker et al., Nucl. Acids Res. 9:133 (1981). More than one coding sequence may be chosen in situations where the codon preference is unknown or ambiguous for optimum codon usage in the chosen host cell or organism. However, any correct set of codons would encode the desired protein, even if translated with less than optimum efficiency. Example III of Seed et al., U.S. Pat. No. 6,114,148, describes a synthetic Factor VIII gene (encoding B-domain deleted Factor VIII), with altered codon usage which increases the expression of the encoded Factor VIII polypeptide.

It is also anticipated that inhibitory/instability sequences can be mutated such that the encoded amino acids are changed to contain one or more conservative or non-conservative amino acids yet still provide for a functionally equivalent protein. For example, one or more amino acid residues within the sequence can be substituted by another amino acid of a similar polarity which acts as a functional equivalent, resulting in a neutral substitution in the amino acid sequence. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Nucleic acids for genes altered by the methods of the invention or constructs containing said nucleic acids may also be used for in-vivo or in-vitro gene replacement. For example, nucleic acid which produces a polypeptide without the introduced cysteine residue(s) can be replaced in situ with a nucleic acid that has been modified by the method of the invention in situ to ultimately produce a polypeptide with increased stability as compared to the originally encoded polypeptide. Such gene replacement might be useful, for example, in the development of a genetic therapy.

Vectors include retroviral vectors and also include direct injection of DNA into muscle cells or other receptive cells, resulting in the efficient expression of the polypeptide of the invention, using the technology described, for example, in Wolff et al., *Science* 247:1465-1468 (1990), Wolff et al., *Human Molecular Genetics* 1(6):363-369 (1992) and Ulmer et al., *Science* 259:1745-1749 (1993). See also, for example, WO 96/36366 and WO 98/34640.

The polypeptides, nucleic acids, vectors, vector particles and/or host cells of the invention can be isolated and purified by methods known in the art and can be used in pharmaceutical compositions and/or therapies as described further below.

Pharmaceutical Compositions

The pharmaceutical compositions of this invention contain a pharmaceutically and/or therapeutically effective amount of at least one polypeptide, or nucleic acid encoding a polypeptide, of this invention. In one embodiment of the invention, the effective amount of polypeptide per unit dose is an amount sufficient to prevent, treat or protect against the effects of a deficiency, or anticipated deficiency, in the corresponding natural polypeptide. The effective amount of polypeptide per unit dose depends, among other things, on the species of mammal treated, the body weight of the mammal and the chosen inoculation regimen, as is well known in the art.

Preferably, the route of inoculation of the peptide will be subcutaneous or intravenous. The dose is administered at least once.

The term "unit dose" refers to physically discrete units suitable as unitary dosages for mammals, each unit containing a predetermined quantity of active material (e.g., polypeptide, or nucleic acid) calculated to produce the desired effect in association with any accompanying diluent.

The polypeptides or nucleic acids of the invention are generally administered with a physiologically acceptable carrier or vehicle therefor. A physiologically acceptable carrier is one that does not cause an adverse physical reaction upon administration and one in which the polypeptides or nucleic acids are sufficiently soluble and retain their activity to deliver a therapeutically effective amount of the compound. The therapeutically effective amount and method of administration of a polypeptide or nucleic acid of the invention may vary based on the individual patient, the indication being treated and other criteria evident to one of ordinary skill in the art. A therapeutically effective amount of a polypeptide or nucleic acid of the invention is one sufficient to attenuate the dysfunction without causing significant adverse side effects. The route(s) of administration useful in a particular application are apparent to one of ordinary skill in the art.

Routes of administration of the polypeptides and nucleic acids of the invention include, but are not limited to, parenteral, and direct injection into an affected site. Parenteral routes of administration include but are not limited to intravenous, intramuscular, intraperitoneal and subcutaneous. The route of administration of the polypeptides of the invention is typically parenteral.

The present invention includes compositions of the polypeptides and nucleic acids described above, suitable for parenteral administration including, but not limited to, pharmaceutically acceptable sterile isotonic solutions. Such solutions include, but are not limited to, saline and phosphate buffered saline for nasal, intravenous, intramuscular, intraperitoneal, subcutaneous or direct injection into a joint or other area.

A system for sustained delivery of the polypeptide or nucleic acid of the invention may also be used. For example, a delivery system based on containing a polypeptide in a polymer matrix of biodegradable microspheres may be used (57). One such polymer matrix includes the polymer poly (lactide-co-glycolide) (PLG). PLG is biocompatible and can be given intravenously or orally. Following injection of the microspheres into the body, the encapsulated polypeptide is released by a complex process involving hydration of the particles and drug dissolution. The duration of the release is mainly governed by the type of PLG polymer used and the release of modifying excipients (44).

The polypeptides and nucleic acids of the present invention are intended to be provided to the recipient subject in an amount sufficient to prevent, or attenuate the severity, extent or duration of the deleterious effects of a deficiency, or anticipated deficiency, in the corresponding natural polypeptide.

The administration of the agents including polypeptide and nucleic acid compositions of the invention may be for either "prophylactic" or "therapeutic" purpose. When provided prophylactically, the agents are provided in advance of any symptom. The prophylactic administration of the agent serves to prevent or ameliorate any subsequent deleterious effects of the deficiency, or anticipated deficiency in the corresponding natural polypeptide. When provided therapeutically, the agent is provided at (or shortly after) the onset of a symptom of the deficiency or anticipated deficiency. The agent of the present invention may, thus, be provided either prior to the anticipated deficiency (so as to attenuate the anticipated severity, duration or extent of disease symptoms) or after the deficiency, and its resultant symptoms have manifested themselves.

Also envisioned are therapies based upon vectors and viral particles, such as viral vectors and viral particles containing nucleic acid sequences coding for the polypeptides described herein. These molecules, developed so that they do not provoke a pathological effect, will produce the encoded polypeptides of the invention.

Factor VIII Preparations

The isolation and purification of porcine and human plasma-derived factor VIII and human recombinant factor VIII have been described in the literature. See, e.g., Fulcher, C. A., and T. S. Zimmerman, 79 Proc. Nat'l. Acad. Sci. U.S.A. 1648-1652 (1982); Toole, J. J., et al., 312 Nature 342-347 (1984) (Genetics Institute); Gitschier, J., et al., 312 Nature 326-330 (1984) (Genentech); Wood, W. I., et al., 312 Nature 330-337 (1984) (Genentech); Vehar, G. A., et al., 312 Nature 337-342 (1984) (Genentech); Fass, D. N., et al., 59 Blood 594 (1982); Toole, J. J., et al., 83 Proc. Nat'l. Acad. Sci. U.S.A. 5939-5942 (1986); Boedeker, B. G., Semin. Thromb. Hemost. 27(4):385-94 (Aug. 2001). Two preparations of full-length recombinant factor VIII which were licensed for use in humans in the early 1990s are described, e.g., in Schwartz R S, et al., N Engl J Med 323:1800-5 (1990); Lusher J M, et al., N Engl J Med 328:453-9 (1993); Bray G L, et al., Blood 83:2428-35 (1994); and White G C II, et al., Thromb. Haemost 77:660-7 (1997).

B-domain deleted Factor VIII, which lacks the B domain of the full-length protein but retains coagulant activity, and which has been licensed for use in humans is described, e.g., in Osterbert T, et al., Pharm Res 14:892-8 (1997); Lusher J M, et al., Blood 96:266a (2000) (abstract); and Almstedt et al., U.S. Pat. No. 5,661,008.

Hybrid human/porcine factor VIII has also been described in the literature. See, e.g., U.S. Pat. No. 6,180,371.

The classic definition of factor VIII is that substance present in normal blood plasma that corrects the clotting defect in plasma derived from individuals with hemophilia A. As used herein, factor VIII refers to a molecule which has the procoagulant properties of plasma-derived factor VIII or activated factor VIII. Thus, the term factor VIII, as used herein, includes a modified or truncated form of natural or recombinant factor VIII which retains the procoagulant properties of factor VIII or activated factor VIII. Thus, factor VIII, as used herein, includes the uncleaved precursor factor VIII molecule, as well as Factor VIII in various proteolytically processed or otherwise truncated forms known to those skilled in the art, wherein the various forms of Factor VIII possess procoagulant activity. Examples of factor VIII polypeptides are those active factor VIII fragments and factor VIII derivatives disclosed in Andersson et al., U.S. Pat. No. 4,749,780; Andersson et al., U.S. Pat. No. 4,877,614; Toole et al., U.S. Pat. No. 4,757,006; Toole, U.S. Pat. No. 4,868,112; Almstedt et al., U.S. Pat. No. 5,661,008, all of which are incorporated herein by reference. The Factor VIII described in Almstedt et al. is made up of amino acids 1 to 743 and 1649 through 2332 of human factor VIII. This polypeptide sequence is commercially known as rFVIII-SQ or REFACTO [r]. See also, Lind et al., Euro. J. Biochem., 232:19-27 (1995). Other forms of truncated FVIII can also be constructed in which the B-domain is generally deleted. In the Almstedt et al. Factor VIII, the amino acids of the heavy chain, containing amino acids 1 through 740 of human Factor VIII and having a molecular weight of approximately 90 kD are connected to the amino acids of the light chain, containing amino acids 1649 to 2332 of human Factor VIII and having a molecular weight of approximately 80 kD. The heavy and light chains are connected by a linker peptide of from 2 to 15 amino acids, for example a linker comprising lysine or arginine residues, or alternatively, linked by a metal ion bond. These other linkers and different sized linkers could be used. See, also, Pipe and Kaufmann (109) for another Factor VIII variant which was genetically engineered by deletion of residues 794-1689 so that the A2 domain is covalently linked to the light chain. Missense mutations at thrombin and activated protein C inactivation cleavage sites provide resistance to proteolysis, resulting in a single-chain protein that has maximal activity after a single cleavage after arginine-372.

A human factor VIII cDNA nucleotide and predicted amino acid sequences are shown in U.S. Pat. No. 6,180,371. Factor VIII is synthesized as an approximately 300 kDa single chain protein with internal sequence homology that defines the "domain" sequence $NH_2$-A1-A2-B-A3-C1-C2-COOH. In U.S. Pat. No. 6,180,371, factor VIII domains include the following amino acid residues, when the sequences are aligned with the human amino acid sequence set forth in that patent: A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes or on other surfaces.

The heavy chain of factor VIII contains the A1 and A2 domains and may also contain part or all of the B domain. (The heavy chain of B-domain deleted factor VIII contains two domains, A1 and A2, and may contain a small part of the B-domain.) The light chain of factor VIII contains three domains, A3, C1, and C2.

Factor VIII Pharmaceutical Compositions

Pharmaceutical compositions containing disulfide-stabilized factor VIII, alone or in combination with appropriate pharmaceutical stabilization compounds, delivery vehicles, and/or carrier vehicles, may be prepared according to known methods, such as those described in Remington's Pharmaceutical Sciences by E. W. Martin, incorporated herein by reference. Pharmaceutical compositions may contain factor VIII polypeptide, nucleic acid coding for factor VIII, or the like.

In one preferred embodiment, the preferred carriers or delivery vehicles for intravenous infusion are physiological saline or phosphate buffered saline that may include sugars.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidylethanolamine, stearoyl phosphatidylcholine, arachadoylphosphatidyl choline, and cholesterol) in an inorganic solvent that is then evaporated, leaving behind a thin film of dried lipid on the surface of the container. An aqueous solution of the factor VIII is then introduced into the container. The solution is mixed to free lipid material from the sides of the container and to disperse lipid aggregates, thereby forming the liposomal suspension.

The factor VIII can be combined with other suitable stabilization compounds, delivery vehicles, and/or carrier vehicles, including vitamin K-dependent clotting factors, tissue factor, von Willebrand factor (vWf) or a fragment of vWF that contains the factor VIII binding site, and polysaccharides such as sucrose.

Factor VIII can be stored bound to vWf to increase the half-life and shelf-life of the molecule. Additionally, lyophilization of factor VIII can improve the yields of active molecules in the presence of vWf. Methods for storage of factor VIII include: lyophilization of factor VIII in a partially-purified state (as a factor VIII "concentrate" that is infused without further purification), and immunoaffinity-purification of factor VIII and lyophilization in the presence of albumin, which stabilizes the factor VIII. Factor VIII can also be prepared by a process that uses sucrose as a stabilizer in the final container in the place of albumin. It is preferred that Factor VIII be prepared by a process that doesn't include any plasma or plasma proteins. (See, e.g., Boedeker (111) and Cho et al., U.S. Pat. No. 6,358,703 B1).

Additionally, factor VIII has been indefinitely stable at 40° C. in 0.6M NaCl, 20 mM MES, and 5 mM $CaCl_2$ at pH 6.0 and also can be stored frozen in these buffers and thawed with minimal loss of activity.

Methods of Treatment

Factor VIII is used to prevent, treat or ameliorate uncontrolled bleeding due to factor VIII deficiency (e.g., intraarticular, intracranial, or gastrointestinal hemorrhage) in subjects such as hemophiliacs with and without inhibitory antibodies and patients with acquired factor VIII deficiency due to the development of inhibitory antibodies (51). The preferred subjects are mammals, most preferably humans. The active materials are preferably administered intravenously.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

Additionally, factor VIII can be administered by transplant of cells genetically engineered to produce the factor VIII or by implantation of a device containing such cells, as described above.

In a preferred embodiment, pharmaceutical compositions of factor VIII alone or in combination with stabilizers, delivery vehicles, and/or carriers are infused into patients intravenously.

The treatment dosages of factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the factor VIII is included in the pharmaceutically acceptable carrier, delivery vehicle, or stabilizer in an amount sufficient to deliver to a patient a therapeutically effective amount of the factor VIII to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. See, e.g., Lusher, J. M., et al., New. Engl. J. Med. 328:453-459 (1993); Pittman, D. D., et al., Blood 79:389-397 (1992), and Brinkhous et al., Proc. Natl. Acad. Sci. USA, 82:8752-8755 (1985).

Usually, the desired plasma factor VIII level to be achieved in the patient through administration of the hybrid or hybrid equivalent factor VIII is in the range of 30-100% of the normal plasma level. Typical dosages for treatment of hemorrhage from hemophilia A with Factor VIII are 25-50 units/kg of body weight. One unit=the normal amount of VIII in 1 ml of citrated normal human plasma. See, e.g., Roberts, H R and Hoffman, M. Hemophilia A and Hemophilia B. in Williams Hematology, 6th edition. eds E Beutler, M A Lichtman, B S Coller, T J Kipps and U Seligson. McGraw-Hill, N.Y. 2001. In a preferred mode of administration of factor VIII of the invention, which is expected to have increased stability due to the introduction of one or more cysteine residues, the composition is given intravenously at a preferred dosage in the range from about 0.1 to 80 units/kg body weight, more preferably in a range of 0.5 to 50 units/kg body weight, more preferably in a range of 1.0-50 units/kg body weight, and most preferably at a dosage of 2.0-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions-Congenital Deficiencies of Prothrombin (Factor II, Factor V, and Factors VII to XII)," Ch. 153, 1453-1474, 1459-1460, in Hematology, Williams, W. J., et al., ed. (1990). Patients with inhibitors may require more factor VIII of the invention, or patients may require less factor VIII of the invention because of its greater stability than human factor VIII. In treatment with factor VIII, the amount of factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration and other ranges set forth herein are exemplary only and are not intended to limit the scope or practice of the claimed invention.

Treatment can take the form of a single intravenous administration of the composition or periodic or continuous administration over an extended period of time, as required. Alternatively, factor VIII can be administered subcutaneously or orally with liposomes in one or several doses at varying intervals of time.

Hybrid animal/human factor VIII of the invention can be used to treat uncontrolled bleeding due to factor VIII deficiency in hemophiliacs who have developed antibodies to human factor VIII. In this case, coagulant activity that is superior to that of natural human or animal factor VIII alone is not necessary. Coagulant activity that is inferior to that of natural human factor VIII (i.e., less than 3,000 units/mg) will be useful if that activity is not neutralized by antibodies in the patient's plasma.

Factor VIII can also be delivered by gene therapy. The general principles for this type of therapy are known to those skilled in the art and have been reviewed in the literature (e.g. 52, 53, 57). Various strategies have been utilized to deliver factors VIII and IX by gene therapy and many of these may be appropriate for delivery of factor VIII that is modified by the addition of engineered disulfide bonds. Following is a summary of the various approaches that could be utilized.

By far the largest volume of experience has been with retroviral vectors. An example of the extant peer-reviewed and published preclinical data using retroviral vectors to treat hemophilia comes from Kay et al (58), who prepared a retroviral vector expressing canine FIX and infused it into the portal vein of hemophilic dogs that had undergone partial hepatectomy. They were able to demonstrate long-term expression of canine FIX (>2 years) but at levels that were far too low to be therapeutic in humans.

Another approach, also for hemophilia B, makes use of an AAV vector. AAV vectors in present use are engineered from a parvovirus, AAV serotype 2, with a small (4.7 kb) single stranded DNA genome. Many individuals are infected with the wild-type virus as children, but infection is not associated with any known illness. The virus is naturally replication-defective, and the engineered vector is completely devoid of viral coding sequences. Preclinical studies by several groups have shown that AAV vectors can direct sustained expression of a transgene introduced into skeletal muscle, liver, or central nervous system (62-64). In the case of FIX, experiments in mice have resulted in expression levels of 250 to 350 ng/mL (5% to 7% of nonnal circulating levels), whereas similar experiments in hemophilic dogs resulted in levels of 70 to 80 ng/mL (approx. 1.5% of normal levels (65, 66)).

Efforts are also underway to extend the use of a liver-directed AAV approach to FVIII, but the size of the transgene presents a problem in this case, because AAV vectors cannot accommodate inserts above 5 kb and the B domain-deleted FVIII cDNA (without promoter, intron, or viral-inverted terminal repeats) is 4.4 kb. Because of these size constraints, several novel strategies have been devised to allow expression of FVIII from an AAV vector (76, 77, 78).

A different approach that is currently being evaluated for treatment of hemophilia A is ex vivo introduction of a plasmid expressing B-domain-deleted (BDD) FVIII into autologous fibroblasts, which are then reimplanted on the omentum. In this strategy, a skin biopsy from the patient serves as a source of autologous fibroblasts, which are then transfected by electroporation with a plasmid expressing BDD FVIII and a selectable marker. After transfection, FVIII-expressing cells are selected, expanded, and reimplanted on the omentum in a laparoscopic procedure (using on the order of $10^8$ to $10^9$ cells) (107).

Adenoviral vectors have several attractive features as gene delivery vehicles, including ease of preparation and efficient transduction of the liver after introduction of vector into the peripheral circulation. These characteristics were exploited by Kay et al (80) to obtain high-level expression of canine FIX in hemophilic dogs as an early proof of principle for this approach. Several important insights about adenoviral vectors have been gained through the work of Connelly and colleagues (83-87), who have explored the use of earlier generation adenoviral vectors as an approach to treating hemophilia A. Using an adenoviral vector expressing B domain-deleted FVIII, these workers were able to demonstrate phenotypic correction of the bleeding diathesis in mice with hemophilia A (87). Levels of expression were initially >2000 mU/mL and, as expected, declined gradually over 9 months to approx. 100 mU/mL.

Lentiviral vectors (101), a newer gene delivery vehicle based on HIV, have also been shown to transduce liver, muscle, and hematopoietic cells and thus could potentially be used for gene therapy for hemophilia. Work published by Kafri et al (102) demonstrated stable expression (22 weeks) of a humanized GFP after direct intraparenchymal injection into liver of a lentiviral vector.

Okoli et al (106) have presented a preliminary report in which FIX plasmid DNA contained within a chitosan DNA nanosphere is embedded within gelatin cubes and fed to mice at a dose of 25 g plasmid in a single treatment. Treated mice showed levels of 45 ng/mL (approx. 1% normal plasma levels), although levels gradually declined to undetectable over a 14-day period.

Phase I clinical trials in humans are underway or in late planning stages for retroviral vectors, AAV vectors, transfected plasmids and adenoviral vectors.

As will be obvious to those of skill in the art, similar methods may be used for the administration of entities other than factor VIII such as factor V, prothrombin, factor XII, HGFA (hepatocyte growth factor activator), and PHBP (plasma hyaluronin binding protein).

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

Example 1

Factor V

In one embodiment of the present invention, one may engineer into recombinant FV mutants a disulfide bond between the A2 and the A1 or A3 domains such that dissociation of the A2 domain is prevented. Neither the x-ray crystal structure nor NMR structure of FVa is known. However, as noted above, the present invention is not limited to use with such structures and may be applied to homology models.

Accordingly, the computer program MODIP (19), which employs the algorithm of Sowdhamini, was applied to the Pellequer homology model of FVa (20). As noted above, MODIP predicts sites for the introduction of disulfide bridges and provides grades (A, B, C) for each prediction. Grade A sites are those predicted to be most optimal for the establishment of disulfide bridges, while grade B and grade C sites are progressively less ideal.

For the Pellequer FVa model, no grade A sites were predicted at either the A1-A2 or A2-A3 interfaces, a single grade B site was predicted, and several grade C sites were predicted. Of the grade C sites predicted, MODIP indicated five sites to be the most ideal:

| | |
|---|---|
| His609 - Glu1691 | (A2-A3) |
| Leu238 - Gln590 | (A1-A2) |
| His253 - Asp469 | (A1-A2) |
| Ala257 - Met618 | (A1-A2) |
| Leu283 - Met618 | (A1-A2) |

It was noted that of these, the pair 609-1691 aligned with residues Tyr664-Thr1826 in Factor VIII.

Visual inspection of the predicted grade B and C sites using computational graphics analysis showed the grade B site to be unusable. Next, a version of the FVa homology model further including a disulfide bridge was constructed for each of the five best grade C sites. This was done using the Xfit computer program, with refinement being provided by the X-PLOR computer program using the Charm22 all atoms force field.

After refinement, the modeled disulfide bonds were analyzed for optimal disulfide geometry. Cys609-Cys1691 provided the best potential geometry for a disulfide bond in FV with $r_{ss}$=2.02 Å, $\chi_{ss}$=80.9°, and the lowest Van Der Waals gas phase energy of the five sites. The second best site was Leu238-Gln590, with $r_{ss}$=2.03 Å and $\chi_{ss}$=−111.6°. Thus, these two sites were chosen for initial attempts to create disulfide bonds using site-directed mutagenesis.

Next a plasmid pED-FV containing full-length FV cDNA was obtained. The full-length FV cDNA in the plasmid pED-FV was then removed by digestion with SalI and inserted into a modified pUC119 plasmid. A fragment of the FV cDNA was next created with PCR using a 5' primer that created a BamHI site at nt4641 (FV cDNA numbering; nt=nucleotide) and a 3' primer that retained the BamHI site at nt6014 while removing the BamHI site at nt5975. The primers used are shown below, where underlining indicates mutation and boldface indicates a codon or restriction site of interest:

```
5'-primer (4641 site)
5'-CACGGATCCTACAGATTACATTGAGATCA-3'

3'-primer (5975 removal, retain 6014)
5'-GTCTGGATCCCTGTGATTATGACTTCCTTTTGCATGTCCACCT**GAAT
CCAAG**-3'
```

The pUC119-FV was digested with Bam-HI (cutting at nt2601, 5975 and 6014 in FV cDNA numbering). The new PCR fragment was inserted between the BamHI sites in pUC119-FV between nt2601 and 6014. These steps resulted in the removal of nt2602 to 4641 (coding sequence for residues 812 to 1491) creating a construct encoding a B-domainless FV designated FVΔB.

This FVΔB gene construct was inserted into the expression vector pcDNA3.1+ from Invitrogen (Carlsbad, Calif.). Then, using the Stratagene Quikchange PCR mutagenesis kit (La Jolla, Calif.) and FVΔB, Ser2183 was mutated to Ala (changing codon AGT to GCC) to prevent glycosylation at Asin2181, yielding the mutant 2183A-FVΔB. This mutation was made to avoid FV heterogeneity due to incomplete glycosylation at Asn2181 which gives two species of FV that differ in certain functional properties (25, 26). All subsequent mutations were made using this B-domainless, Ser2183A mutant. In some embodiments, this step maybe eliminated.

At the same time, the Stratagene Quikchange PCR mutagenesis kit was used to place coding for cysteine residues by the addition of four mutagenic primers. The following pairs were made: Leu238Cys:Gln590Cys (Cys238/Cys590), and His609Cys:Glu1691Cys (A2-SS-A3). Variants were also made with additional mutations of Arg506 and Arg679 to Gln (Gln506 or Gln679) (Q506/Cys238/Cys590, Q506-A2-SS-A3 and Q506/Q679-A2-SS-A3). The mutagenesis primers used are shown below, where underlining indicates mutation and boldface indicates a codon or restriction site of interest:

```
Ser2183 - Ala
Forward primer
5'-CATGGAATCAAGCTATTACACTTCGCC-3'

Reverse primer
5'-GGCGAAGTGTAATAGCTTGATTCCATG-3'

Leu238 - Cys
Forward
5'-GGCCAGAATGCTTCTCCATTC-3'

Reverse
5'-GAATGGAGAAGCATTCTGGCC-3'

Gln590 - Cys
Forward
5'-GTGGGGACCTGTAATGAAATT-3'

Reverse
5'-AATTTCATTACAGGTCCCCAC-3'

His609 - Cys
Forward
5'-CTATGGAAAGAGGTGTGAGGACACC-3'

Reverse
5'-GGTGTCCTCACACCTCTTTCCATAG-3'

Glu1691-Cys
Forward
5'-GATCAGGGCCATGTAGTCCTGGC-3'

Reverse
5'-GCCAGGACTACATGGCCCTGATC-3'

Arg306 - Gln
Forward
5'-CCAAAGAAAACCCAGAATCTTAAG-3'

Reverse
5'-CTTAAGATTCTGGGTTTTCTTTGG-3'

Arg506 - Gln
Forward
5'-CTGGACAGGCAAGGAATACAG-3'

Reverse
5'-CTGTATTCCTTGCCTGTCCAG-3'

Arg679 - Gln
Forward
5'-CATGGCTACACAGAAAATGCATG-3'

Reverse
5'-CATGCATTTTCTGTGTAGCCATG-3'
```

Plasmids containing each mutant were purified with the Qiafilter plasmid midiprep kit from Qiagen, linearized and transfected into COS-1 cells using Superfect tranisfection reagent according to the manufacturer's instructions. More specifically, 1 µg of DNA was incubated in 60 µL volume of DMEM/F12 media with 5 µL of Superfect reagent for ten minutes. Then 350 µL of DMEM/10% FBS/1 mM Glutamine was added and this mixture was transferred to COS-1 cells (about 50% confluent) in wells of a 24-well plate and incubated for 3 hours before washing and replenishing with fresh media. Stable clones were selected using 0.8 mg/mL Geneticin (Gibco BRL, Rockville, Md.). Serum-free conditioned media containing 0.05% BSA and 5 mM $CaCl_2$ was collected from COS-1 cells expressing each FV mutant and was precipitated with 16% PEG 6000. Then the pellet was redissolved in HBS (50 mM HEPES, 150 mM NaCl, pH 7.4) containing 5 mM $CaCl_2$, 2 mM benzamidine, 5 nM PPACK and 1 mM PMSF, dialyzed versus the same buffer and purified using an anti-FV antibody column (24). Fractions containing FV were collected, concentrated and stored in HBS with 0.1% BSA at −80 C.

FVa was quantified by activity and by ELISA assay after activation by thrombin. ELISA assays used Nunc Maxisorb plates coated with 10 µg/ml sheep-anti-FV from Affinity Biological (Hamilton, Ontario, Calif.) and blocked with Superblock from Pierce (Rockford, Ill.) with antigen detection by mouse anti-FV-light-chain monoclonal antibody (V59). FV (40 nM) was activated with thrombin (0.5 nM) in HBS with 0.1% BSA and 5 mM $CaCl_2$ at 37° C. for 10 min and activation was stopped by the addition of 1.1 molar equivalent of hirudin. FVa inactivation assays were performed using FVa at 4 nM and APC at 2.5 nM with determination of residual FVa using prothrombinase assays as described (27). Inactivation of FVa was measured as follows. A mixture of 1 nM FVa with 25 µM phospholipid vesicles was made in 50 mM HEPES, pH 7.4, 100 mM NaCl, 0.5% BSA, 5 µM $CaCl_2$, 0.1 mM $MnCl_2$ (called Ptase buffer). Inactivation was initiated by the addition of APC. One µL aliquots were removed at time points and added to 40 µL of 1.25 nM factor Xa with 25 µM phospholipid vesicles, followed by 10 µL of 3 µM prothrombin (final concentrations: 1 nM FXa, 20 pM FVa, 25 µM phospholipid vesicles and 0.6 µM prothrombin). After 2.5 min a 15 µL aliquot of this mixture was quenched by addition to 55 µL TBS containing 10 mM EDTA, 0.5% BSA, pH 8.2. Chromogenic substrate CBS 34-47 was added and the amount of thrombin formation was assessed by measuring the change in absorbance at 405 nm.

For some studies, FXa or prothrombin was varied. For Xa titrations, a mix of 3.34 pM FVa/FVai and 41.7 µM phospholipid vesicles in Ptase buffer was aliquoted in 30 µL aliquots into wells of 96-well plate (polypropylene, V-well). 10 µL of Xa was added to each well in the same buffer at various concentrations. At time=0, 10 µL of 1.5 µM prothrombin (FII) was added to all wells (final concentrations=2 pM FVa, 25 µM PL vesicles, 5-600 pM Xa, 0.3 µM FII). At time=12 min, the Ptase reaction was stopped by removing 15 µL to a 96-well plate containing 55 µL TBS containing 0.5% BSA, 10 mM EDTA at pH 8.2. Next, the amount of thrombin formed was measured with the chromogenic substrate CBS 34-47. For prothrombin, 20 µL of mix containing 125 pM Xa, 1.25 nM FVa/FVai, and 31.25 µM PL vesicles in Ptase buffer was aliquoted into wells of 96-well V-well plate. At time=0, 5 µL FII at varying concentrations (final concentration 100 pM Xa, 1 nM FVa, 25 µM PL, 25-1500 nM FII) was added. At time=2: 30, the reaction was stopped by removing 15 µL to 55 µL EDTA buffer as above. Thrombin was measured as above.

SDS-PAGE was then performed with Novex 4-12% Bis-Tris gradient gels with MOPS buffer (Invitrogen, Carlsbad, Calif.). 50 ng protein was loaded per lane. The proteins were then transferred to Millipore PVDF membranes, and immunoblots were developed with monoclonal anti-FV-light chain antibodies, AHV-5112 or V59, and rabbit polyclonal anti-FV-heavy chain antibodies (24). More specifically, membranes were blocked with TBS, 1% Casein, and 2 mM $CaCl_2$. Antibodies were diluted in the same buffer. The primary antibody was the respective anti-FV antibody, and the secondary antibody was biotinylated goat anti-mouse IgG or biotinylated donkey anti-rabbit IgG from Pierce. Visualization was then performed with streptavidin-conjugated alkaline phosphatase and 1-step NBT/BCIP substrate (also from Pierce). For the FV species that were produced and purified, yields of pure FV ranged from 5 to 25 μg/L of conditioned media. Based on silver-stained SDS-PAGE, we estimated the purity of the mutants to range from 70% to 90%.

Figure 3:
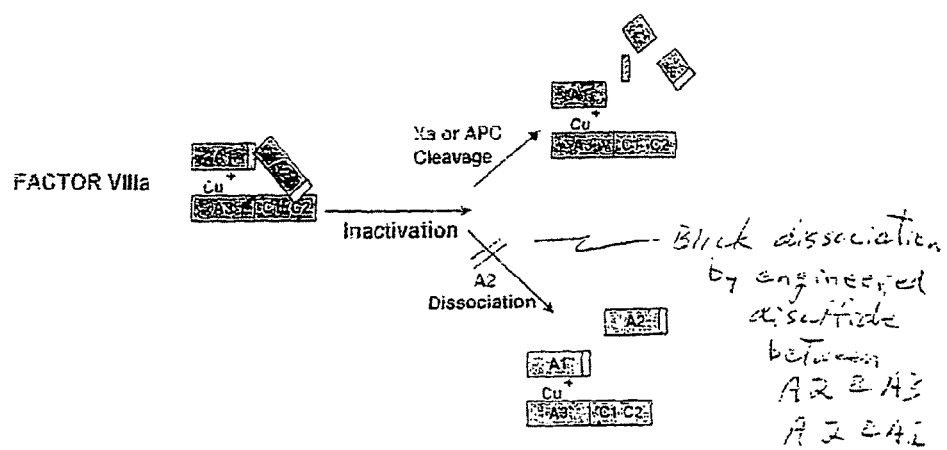
FIG. 3 is a schematic illustrating the prevention of dissociation of the A2 domain from heterotrimeric Factor VIIIa by introduction of a disulfide bond between the A2 and A3 domains, or the A2 and A1 domains, of FVIIIa.

As is known in the art, the FVa light chain normally gives a doublet on SDS-PAGE due to heterogeneity created by incomplete glycosylation at Asn2181. Mutation of Ser2183 to Ala eliminates this glycosylation site (28). Immunoblots confirmed that all our recombinant FV molecules had an apparent molecular weight of 188 kDa, consistent with deletion of residues 812 to 1491. Immunoblots further confirmed that the wild type recombinant FVa formed a light chain doublet, whereas all other Fva mutants carrying the Z183A mutation had only a single light chain band.

To demonstrate the desired interdomain disulfide bonds in the mutant FV proteins containing two engineered cysteine residues, immunoblots of FVa and APC-treated FVai (where "i" indicates inactivated) were run. FIG. 1 shows schemes representing the primary sequences of FVΔB, FVa (formed upon thrombin activation), and FVai (inactivated by APC cleavages).

Immunoblots using a polyclonal anti-FV heavy chain antibody demonstrated that introduction of Cys238/Cys590 mutations into FV or Q506-FV did not detectably link the A1 and A2 domains although these species had normal FVa activity, leading us to conclude that no disulfide bond was formed between these cysteines.

If FV mutants containing Cys609 and Cys1691 generate a new disulfide bond between the A2 and A3 domains as depicted in FIG. 1C, it would link the FVa heavy and light chains. In this case, in immunoblots of FVa, the disulfide-bonded species would appear at a molecular weight corresponding to the additive molecular weights of the heavy and light chains, and following APC cleavages at Arg506, Arg306 and Arg679 that normally cause complete FVa inactivation, the light chain of FVai would remain cross-linked to the C-terminal fragment of the A2 domain (A2c, residues 507 to 679).

Indeed such results were obtained. In immunoblots developed with anti-FV light chain antibodies (FIG. 2A), lanes 1 and 2 containing 2183A-FVa and 2183A-FVai both showed a normal light chain at the expected molecular weight (69 kDa), whereas in lane 3, the mutant containing Cys609/Cys 1691-FVa showed a predominant band predicted for cross-linked light chain and heavy chain (158 kDa). Thus, FV mutants containing these two Cys residues are justifiably designated "A2-SS-A3".

Lane 4 demonstrated that APC-treated A2-SS-A3-FVai gave a predominant band corresponding to the mobility predicted for the light chain cross-linked to the A2c fragment (92 kDa). A fainter band slightly above this band correlated with a band predicted for heavy chain cleaved at Arg506 but not Arg679, resulting in the fragment 507 to 709 (101 kDa). Lanes 5 and 6 (FIG. 2A) contained Q506-A2-SS-A3-FVa and Q506-A2-SS-A3-FVai. In these species, Arg506 cleavage cannot take place such that in Q506-A2-SS-A3-FVai (lane 6) the light chain remained cross-linked to the entire A2 domain (with or without its small C-terminal tail of residues 680-709). Indeed, the observed higher molecular weight band (lane 6) corresponded to the light chain cross-linked to the A2 domain (130 kDa). Lanes 7 through 12 of FIG. 2A contained samples parallel to those of lanes 1 through 6, which were reduced using DTT. Lanes 7-12 show that, following reduction, the various higher molecular weight cross-linked species disappeared and normal light chain bands appeared, proving that the higher molecular weight light chain-containing species seen in lanes 3-6 (FIG. 2A) were indeed the result of disulfide cross-lhiks between light and heavy chains.

Additional proof for covalent cross-links between FVa heavy and light chains in A2-SS-A3 mutants containing Cys609/Cys1691 came from immunoblot analyses using anti-FV heavy chain antibodies that showed, under non-reducing conditions, the same new bands visualized in immunoblots developed using anti-FV light chain antibodies. For example, in FIG. 2B such immunoblots of A2-SS-A3-FVa and A2-SS-A3-FVai as well as Q506-A2-SS-A3-FVa and Q506-A2-SS-A3-FVai under non-reducing conditions gave bands predicted to represent the same cross-linked species visualized in immunoblots developed using anti-FV light chain antibodies FIG. 2B. Lanes 1 and 5 (FIG. 2B) both showed bands corresponding to light chain cross-linked to heavy chain that co-migrated with that seen in FIG. 2B, lane 3 (157 kDa). Lane 2 in FIG. 2B showed a band corresponding to the light chain cross-linked to the A2c fragment, co-migrating with a band seen in lane 4 of FIG. 2A (102 kDa). Lane 6 in FIG. 2B showed a band corresponding to the light chain cross-linked to the A2 domain, equivalent to a band seen in lane 6 of FIG. 2A (132 kDa).

Finally, free A2-C terminus fragment (24 kDa) and A2 (63 kDa) fragment were not visible in the non-reduced lanes 2 and 6, respectively, but were visible in the reduced lanes 4 and 8, indicating that these fragments were released from the disulfide-linked species upon reduction.

Immunoblot analyses of Q506-A2-SS-A3 FVa and Q506/Q679-A2-SS-A3-FVa showed that there was a small amount of free light chain that was not cross-linked to heavy chain (FIG. 2), indicating that disulfide cross-linking in the A2-SS-A3-FVa mutants was not 100% complete. Densitometry analysis of these non-reduced immunoblots showed that, on average, about ten percent of the Q506-A2-SS-A3-FVa molecules lacked disulfide cross-links.

As alluded to above, FIG. 1A is a schematic of the primary sequence of FVΔB with the locations of the different domains indicated. The schematic of FIG. 1*b* shows activated FVΔB (FVa), a heterodimer of the N-terminal heavy chain and the C-terminal light chain associated in the presence of $Ca^{2+}$ ions. Arrows indicate sites of cleavage in FVa by APC. The schematic of FIG. 1C shows the cleavage fragments produced upon inactivation of FVa (FVai) by APC, and further shows the sites of the cysteine mutations that did (His609-Glu1691) and did not (Leu238-Gln590) result in disulfide bond formation.

Example 2

Factor VIII

As is known in the art, there are a number of similarities between Factor V and Factor VIII. More specifically, Factors V and VIII have similar gene structures, have highly homologous amino acid sequences and domain structures, are both activated by highly specific cleavages by thrombin, and both are inactivated by limited proteolysis by activated protein C (APC). Accordingly, one may engineer into recombinant FVIII disulfide bonds between the A2 and the A1 or A3 domains using a method similar to that disclosed above concerning FV. As is known in the art, FVIIIa is thermodynamically unstable because the A2 domain can spontaneously disassociate. As shown in FIG. 3, placement of a disulfide bond between the A2 and the A1 or A3 domains of FVIIIa has the advantage of preventing this dissociation.

Like FVa, neither the x-ray crystal nor NMR structure of FVIIIa is known. However, as noted above, the present invention is not limited to use such structures and may be applied to homology models.

As a first step in engineering a disulfide bond between the A2 and the A1 or A3 domains of FVIIIa, the computer program MODIP, which employs the algorithm of Sowdhamini, was applied to the Pemberton et al. (54) homology model of the A domains of FVIIIa. As noted above, MODIP predicts sites for the introduction of disulfide bridges and provides grades (A, B, C) for each prediction. Grade A sites are those predicted to be most optimal for the establishment of disulfide bridges, while grade B and grade C sites are progressively less ideal. For the Pemberton FVIIIa model fifteen sites were predicted:

| Grade A: | |
|---|---|
| Met 662 - Asp 1828 | (A2-A3) |
| Grade B: | |
| Ser 268 - Phe 673 | (A1-A2) |
| Ile 312 - Pro 672 | (A1-A2) |
| Ser 313 - Ala 644 | (A1-A2) |
| Met 662 - Lys 1827 | (A2-A3) |
| Tyr 664 - Thr 1826 | (A2-A3) |
| Grade C: | |
| Pro 264 - Gln 645 | (A1-A2) |
| Arg 282 - Thr 522 | (A1-A2) |
| Ser 285 - Phe 673 | (A1-A2) |
| His 311 - Phe 673 | (A1-A2) |
| Ser 314 - Ala 644 | (A1-A2) |
| Ser 314 - Gln 645 | (A1-A2) |
| Val 663 - Glu 1829 | (A2-A3) |
| Asn 694 - Pro 1980 | (A2-A3) |
| Ser 695 - Glu 1844 | (A2-A3) |

Of these, the pair Tyr 664-Thr 1826 was noticed to be in a position homologous to the pair His609-Glu1691 in FVa. As noted above, a disulfide bridge may be successfully engineered into FV by placing coding for cysteine residues at positions 609 and 1691.

Similar to the method described above for FV, visual inspection of these pairs was preformed using computational graphics analysis. As a result of this analysis, three of the proposed pairs were chosen for further investigation: Met 662-Asp 1828, Tyr 664-Thr 1826 and Ser 313-Ala 644. For each of these three sites, a version of the FVIIIa model further including a disulfide bridge at the appropriate location was constructed using the Xfit computer program, with refinement being provided by the X-PLOR computer program using the Charm22 all atoms force field. After refinement, the modeled disulfide bonds were ranked in the order given above with Cys 662-Cys 1828 providing the best potential geometry for a disulfide bond. It was chosen to make this mutant and the mutant Cys 664-Cys1826 in recombinant factor VIII in a maiiner analogous to that described above with reference to FV.

A FVIII expression plasmid (p25D) was obtained from Bayer Corporation. This plasmid expresses B-domain deleted FVIII in which residues 744 to 1637 from the B domain are deleted.

Next, using the Stratagene Quikchange PCR mutagenesis and the mutant FVIII, two cysteine residues were inserted to permit the creation of a disulfide bond by the addition of four mutagenic primers at the same time. The following two pairs were made: Met662Cys:Asp1828Cys and Tyr664Cys: Thr1826Cys. The mutagenesis primers used are shown below, where underlining indicates mutation and boldface indicates a codon or restriction site of interest:

```
Met662 - Cys
Forward
5'-CCTTCAAACACAAATGCGTCTATGAAGACACACTCACC-3'

Reverse
5'-GGTGAGTGTGTCTTCATAGACGCATTTGTGTTTGAAGG-3'

Asp1828 - Cys
Forward
5'-GGCACCCACTAAATGTGAGTTTGACTGCAAAGC-3'

Reverse
5'-GCTTTGCAGTCAAACTCACATTTAGTGGGTGCC-3'

Tyr664 - Cys
Forward
5'-CACAAAATGGTCTGTGAAGACACACTCACCC-3'

Reverse
5'-GGGTGAGTGTGTCTTCACAGAGGATTTTGTG-3'

Thr1826 - Cys
Forward
5'-CATATGGCACCCTGTAAAGATGAGTTTGACTGC-3'

Reverse
3'-GCAGTCAAACTCATCTTTACAGGGTGCCATATG-3'
```

The Tyr664-Cys reverse primer shown above was the actual sequence used but the actual FVIII gene sequence at nucleotides 22 and 23 should be CC rather than GG. But the forward primer has the correct sequence and the correct sequence was selected for the final C664 mutant by DNA sequencing of the selected clones.

Figure 4:
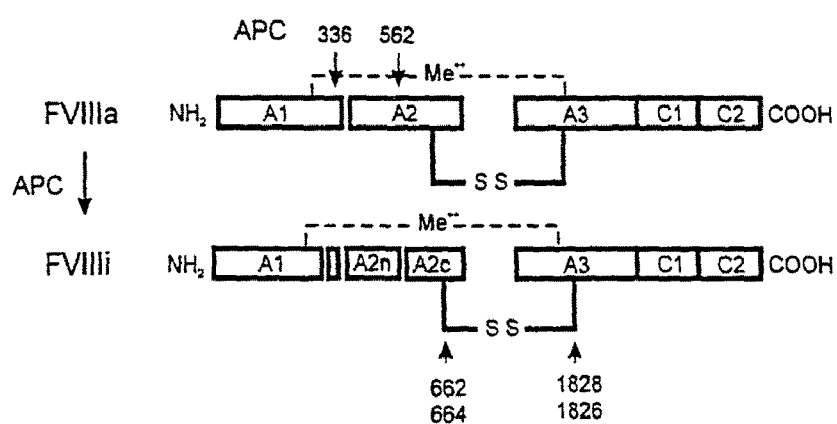
FIG. 4 is a schematic showing the expected action of APC upon mutant FVIIIa containing both a disulfide bridge between cysteine residues introduced at positions corresponding to Met 662-Asp 1828 in one mutant or Tyr 664-Thr 1826 in another mutant, and showing the APC cleavage sites at residues Arg 336 and Arg 562.

FIG. 4 is a schematic showing the expected action of APC upon mutant FVIII containing a disulfide bridge between sites Met 662-Asp 1828 or Tyr 664-Thr 1826.

In some embodiments, variants may be made which additionally contain mutations and/or deletions of APC cleavage sites Arg 336 and/or Arg 562 in FVIII. Such additional mutations, as described in Kaufman and Pipe (109) and in U.S. Pat. Nos. 5,422,260, 5,250,421, 5,198,349 (incorporated herein by reference), add additional stability to FVIII by making it more resistant to inactivation.

The nucleic acids encoding Factor VIII mutants may also be modified to contain an increased number of preferred codons for human genes as described, e.g., in Seed et al., U.S. Pat. No. 6,114,148.

Transient expression of wildtype and mutant p25D plasmid was tested in COS-1 cells, K293 cells and BHK-21 cells using Superfect reagent and Effectene reagent, both from Qiagen. The Effectene reagent in K293 cells gave the best results. Yields of recombinant FVIII ranged from 10 to 100 mU/mL of conditioned media according to APTT activity assays and ELISA (Immubind FVIII ELISA, American Diagnostica). Conditioned media was collected from transient transfections in 100 mm dishes in DMEM/F12 media with 2% FBS and the media was concentrated 15-fold and dialyzed into BEPES buffered saline/5 mM $CaCl_2$/0.1 mM $MnCl_2$, pH 7.4. Mock transfection media was treated in the same manner and used as a negative control.

Antigen concentration of recombinant FVIII was determined using the Immubind FVIII ELISA kit from American Diagnostica. The standard curve used was the purified FVIII concentrate provided with the kit (1 unit=the FVIII contained in 1 mL of plasma). Activity was determined with an APTT assay with FVIII deficient plasma and the APTT reagent Platelin LS as follows: 50 μL of FVIII deficient plasma (FVII-IdP, George King Biomedical) was mixed with 50 μL Platelin LS (Organon Teknika) and incubated at 37° C. for three minutes. 5 μL of a FVIII sample was then added, immediately followed by 50 μL of HEPES buffered saline (0.15 M NaCl) with 0.5% BSA and 25 mM $CaCl_2$. Clotting time was measured in the Diagnostica Stago ST4 coagulometer. A FVIII standard curve was made using pooled normal human plasma (George King Biomedical), which is defined to contain 1.0 unit/mL of FVIII. The APTT assay was sensitive to very low levels of FVIII (<0.005 U/nL).

Using these measures of antigen and activity, relative specific activity of the three proteins was calculated (units (U) activity/units (U) antigen). The wildtype FVIII (B domain-deleted) had a relative specific activity of 0.83. C662-C1828-FVIII had a relative specific activity of 3.53 and C664-C1828-FVIII had a relative specific activity of 3.40.

Figure 5:
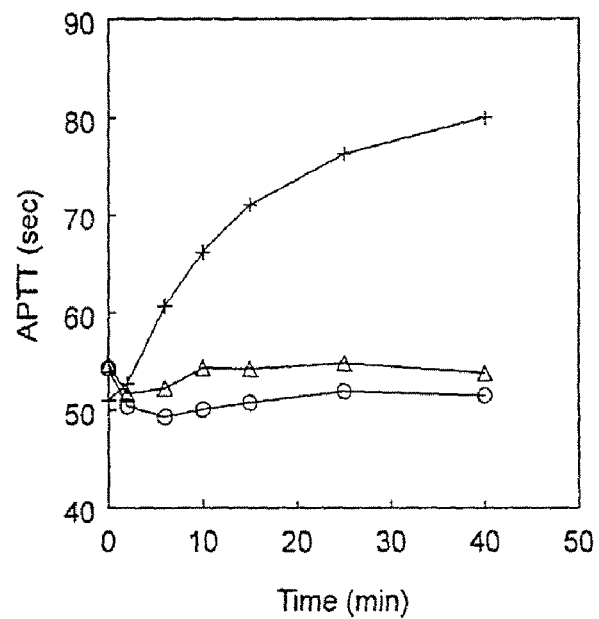
FIG. 5. Stability of Double Cysteine mutants of Factor VIIIa. Recombinant wildtype and double cysteine mutants of FVIIIa were assayed over time for activity in an APTT assay. FVIIIa species as indicated: wildtype (+), C662-C1828 (Δ), C664-C1826 (o). At the start time about 500 mU/mL FVIII was treated with 5.4 nM thrombin and then after one minute hirudin was added to 1 U/mL to inactivate the thrombin. Then samples were removed at indicated times and assayed for remaining FVIIIa activity in the APTT assay.
Figure 6:
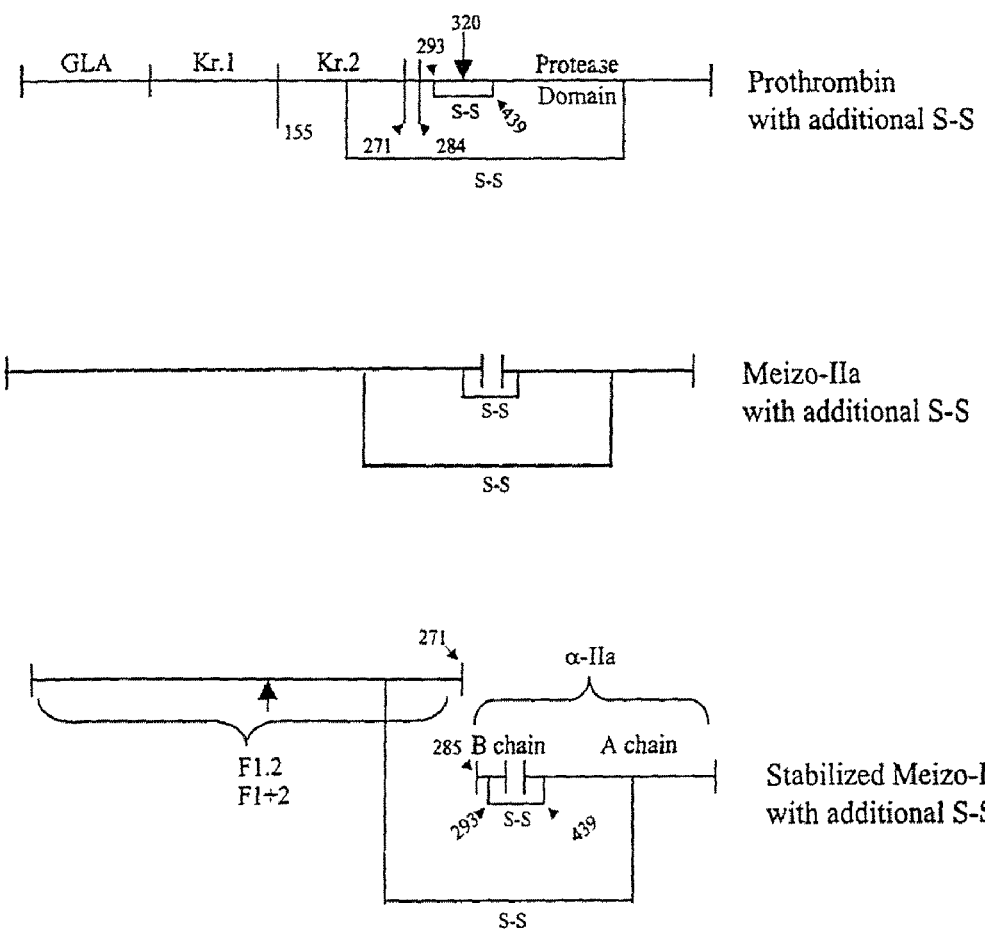
FIG. 6 is a schematic illustrating the introduction of a disulfide bond into human prothrombin to stabilize its meizo-thrombin or meizothrombin (des F1) form, preventing the conversion of meizothrombin or meizothrombin (des F1) to alpha-thrombin (α-IIa). Legend: GLA, Gla domain; Kr.1, kringle 1 domain; Kr.2, kringle 2 domain; Meizo-IIa, meizo-thrombin. Prothrombin and Meizo-IIa are shown with an introduced disulfide bond between the Kringle 2 domain and the protease domain formed from the introduction of a cysteine at a residue N-terminal to its cleavage site at residue 271 in the Kringle 2 domain and the introduction of a cysteine at a residue C-terminal to the cleavage site at residue 320 in the protease domain. The disulfide bond between cysteine residues 293 and 439 is present in the naturally occurring protein.

The stability of thrombin-activated FVIIIa over time was followed using a protocol described by Pipe et al (110) with some modification, in which FVIIIa at a concentration of about 500 mU/mL was generated by the addition of thrombin which was then inactivated with a slight excess of hirudin. Subsequently, aliquots of this mix were removed over time and immediately assayed for FVIIIa activity in the APTT assay as described above. FIG. 5 shows the results of this assay with recombinant wildtype FVIIIa and two recombinant mutants. The two double-cysteine mutants are much more stable over time than wildtype FVIIIa (as reflected in a shorter clotting time). The mock transfection control conditioned media showed essentially no coagulant activity in this assay and no change in activity over the time course (data not shown).

The FVIII mutant produced may be stably transfected into cells. The cells can be grown (or cultured) to permit expression of the FVIII mutants. The FVIII mutant produced may be isolated and purified. In a manner described above with reference to FV, immunoblots may be performed to confirm the lack of the majority of the B domain (if appropriate) and the presence of the engineered disulfide bonds.

Example 3

Porcine-Human Hybrid Factor VIII

There exists in the art hybrid factor VIII molecules whose amino acid sequence derives from both human and non-human-animal ("non-human") factor VIII coding sequences. Examples of such molecules may be found, for example in U.S. Pat. No. 6,180,371, incorporated herein by reference. According to the present invention, non-human/human hybrid factor VIII containing a disulfide bond between the hybrid's A2 and A1 or A3 domains may be created. Like the above example, such a disulfide bond prevents dissociation of the A2 domain.

The creation of such hybrid molecules is largely analogous to the procedure described above for non-hybrid FVIII. Firstly, a homology model of hybrid FVIIIa, for example, one comprised of a non-human A2 domain and a heterodimer of des-A2 human factor VIIIa, may be obtained or created. Alternately, an x-ray crystal structure may be obtained or created if such a structure exists or is capable of being created. The MODIP computer program may next be run on the model or structure so as to receive from the program suggestions of sites for the formation of a disulfide bridge between the A2 and A1 or A3 domains of the hybrid. Alternately, predictive methods may be used as described above.

Next, visual inspection of one or more of the suggested sites may be preformed using computational graphics analysis. As a result of this analysis, a number of proposed sites may be chosen for further investigation. For each of these sites, a version of the hybrid FVIIIa model further including a disulfide bridge at the appropriate location may be constructed using the Xfit computer program, with refinement being provided by the X-PLOR computer program using the Charm22 all atoms force field. After refinement, the modeled disulfide bonds may be ranked based on quality of potential geometry for a disulfide bond. A number of the suggested sites may then be chosen for attempted creation of mutant hybrid FVIII in a manner analogous to that described in reference to FV and non-hybrid FVIII above.

Example 4

Prothrombin

As noted above, in the presence of thrombomodulin and phosphatidylserine/phosphatidylcholine phospholipid vesicles (PCPS), meizothrombin, as well as meizothrombin (des F1), are better activators of protein C than thrombin.

According to the present invention, a mutant prothrombin may be created which includes a disulfide bond to stabilize prothrornbin's meizothrombin (des F1) form, and to prevent the conversion of meizothrombin (des F1) to thrombin. Such a stable meizothrombin (des-F1) has potential application, for example, as an anticoagulant. It was decided to achieve this stabilization by placement of a disulfide bond between the Kringle 2 and protease domains of prothrombin as shown in FIG. 5.

First, the computer program MODIP was applied to the X-ray crystal structure of a human thrombin complex of alpha-thrombin and fragment 2 (55), and the X-ray crystal structure of bovine meizothrombin (des F1) (108) resulting in the following predicted sites in human prothrombin:

| Grade B: | |
| --- | --- |
| Asp261-Arg443 | (KR2-protease) |
| His205-Lys572 | (KR2-protease) |
| Grade C: | |
| Asp261-Lys567 | (KR2-protease) |

Next, visual inspection of one or more of the suggested sites may be performed using computational graphics analysis. As a result of this analysis, a number of proposed sites may be chosen for further investigation. For each of these three sites, a meizothrombin (des F1) homology model including a disulfide bridge at the appropriate location may be constructed using the Xfit computer program, with refinement being provided by the X-PLOR computer program using the Charm22 all atoms force field. After refinement, the modeled disulfide bonds may be ranked based on quality of potential geometry for a disulfide bond. A number of the suggested sites, or sites that have not yet been identified, may then be chosen for attempted creation of mutant prothrombin in a manner analogous to that described in reference to FV and non-hybrid FVIII above.

Example 5

Factor XII, HGFA, and PHBP

As noted above, at least two forms of activated factor XII (FXIIa) exist, αFXIIa and FXIIa fragment. As also noted above, the FXIIa fragment has the bulk of its N-terminal heavy chain fragment no longer associated such that it no longer binds to surfaces but it is still catalytically active. According to the present invention, a disulfide bond can be placed that crosslinks this N-terminal heavy chain fragment to the remainder of the molecule, causing it to retain its surface binding characteristics. It is expected that such a mutant stabilized FXII could find pharmaceutical application as a coagulant.

A second FXII-like polypeptide is HGFA. HGFA activates hepatocyte growth factor (HGF) within injured tissues, where HGF plays roles in tissue repair. As noted above, cleavage of HGFA by kallikrein at Arg372 results in release of the N-terminal heavy chain, which, as in FXII, is involved in surface binding. According to the present invention, a disulfide bond can be placed to prevent the release of the N-terminal heavy chain. It is suspected that a mutant HGFA so stabilized could be used pharmaceutically to aid in tissue repair.

A third FXII-like polypeptide is PHBP. As noted above, PHBP activates FVII, uPA, and tPA and has a structure homologous to HGFA. According to the present invention, a disulfide bond could be placed to prevent the release of the N-terminal heavy chain in PHBP. It is suspected that a mutant PHBP so stabilized could be used pharmaceutically to promote clotting via activation of FVII, uPA, and/or tPA.

No x-ray crystal or NMR structure exists for Factor XII, HGFA, or PBBP. However, homology models for these molecules, such as ones based on the x-ray crystal structure of urokinase, may be created or obtained. Using such homology models, mutants may be created in a manner analogous to that described above with reference to, for example, FV and FVIII.

Example 6

Other Clotting Factors

As is known in the art, several plasma factors other than factors V and VIII are synthesized as a single polypeptide chain, contain multiple independently folded domains, and are subject to limited proteolysis that may result in separation of domains due to dissociation. As noted above, the methods described herein may be used in all cases where one wishes to place a disulfide bond between two domains of a polypeptide. Accordingly, it should be apparent to those in the art that the methods described herein may be applied to a multitude of polypeptides, including many of the human and non-human clotting factors.

REFERENCES

1. Pipe, S. W. and Kaufian, R. J. (1997) *Proc. Natl. Acad. Sci. U.S.A* 94, 11851-11856
2. Davie, E. W., Fujikawa, K. & Kisiel, W. (1991) *Biochemistry* 30, 10363-10370.
3. Esmon, C. T. (2000) *Biochim. Biophys. Acta* 1477, 349-360.
4. Dahlback, B. (2000) *Lancet* 355, 1627-1632.
5. Jenny, R. J., Pittman, D. D., Toole, J. J., Kriz, R. W., Aldape, R. A., Hewick, R. M., Kaufman, R. J. & Mann, K. G. (1987) *Proc. Natl. Acad. Sci. USA* 84, 4846-4850.
6. Esmon, C. T. (1979) *J. Biol. Chem.* 254, 964-973.
7. Nesheim, M. E., Taswell, J. B. & Mann, K. G. (1979) *J. Biol. Chem.* 254, 10952-10962.
8. Kalafatis, M., Rand, M. D. & Mann, K. G. (1994) *J. Biol. Chem.* 269, 31869-31880.
9. Nicolaes, G. A. F., Tans, G., Thomassen, M. C. L. G. D., Hemker, H. C., Pabringer, I., Varadi, K., Schwarz, H. P. & Rosing, J. (1995) *J Biol. Chem.* 270, 21158-21166.
10. Heeb, M. J., Kojima, Y., Greengard, J. & Griffin, J. H. (1995) *Blood* 85, 3405-3411.
11. Mann, K. G., Hockin, M. F., Begin, K. J. & Kalafatis, M. (1997) *J. Biol. Chen.* 272, 20678-20683.
12. Guinto, E. R. & Esmon, C. T. (1984) *J. Biol. Chem.* 259, 13986-13992.
13. Heeb, M. J., Kojima, Y., Hackeng, T. M. & Griffin, J. H. (1996) *Protein Sci.* 5, 1883-1889.
14. Kojima, Y., Heeb, M. J., Gale, A. J., Hackeng, T. M. & Griffin, J. H. (1998) *J. Biol. Chem.* 273, 14900-14905.
15. Perry, L. J. & Wetzel, R. (1984) *Science* 226, 555-557.
16. Sauer, R. T., Hehir, K., Stearman, R. S., Weiss, M. A., Jeitler-Nilsson, A., Suchanek, E. G. & Pabo, C. O. (1986) *Biochemistty* 25, 5992-5998.
17. Villafranca, J. E., Howell, E. E., Voet, D. H., Strobel, M. S., Ogden, R. C., Abelson, J. N. & Kraut, J. (1983) *Science* 222, 782-788.
18. Wells, J. A. & Powers, D. B. (1986) *J. Biol. Chem.* 261, 6564-6570.
19. Pabo, C. O. & Suchanek, E. G. (1986) *Biochemistry* 25, 5987-5991.
20. Sowdhamini, R., Srinivasan, N., Shoichet, B., Santi, D. V., Ramakrishnan, C. & Balaram, P. (1989) *Protein Eng* 3, 95-103.
21. Pellequer, J. L., Gale, A. J., Getzoff, E. D. & Griffin, J. H. (2000) *Thromb. Haemost.* 84, 849-857.
22. Mesters, R. M., Houghten, R. A. & Griffin, J. H. (1991) *J. Biol. Chem.* 266, 24514-24519.
23. McRee, D. E. (1992) *J. Mol. Graph.* 10, 44-47.
24. Brunger, A. T. (1992) *X-PLOR Manual*. Version 3.0 (Yale University, New Haven).
25. Heeb, M. J., Rehemtulla, A., Moussalli, M., Kojima, Y. & Kaufman, R. J. (1999) *Eur. J. Biochem.* 260, 64-75.
26. Rosing, J., Bakker, H., Thornassen, M. C. L. G. D., Thomassen, L., Llemker, H. & Tans, G. (1993) *J. Biol. Chem.* 268, 21130-21136.
27. Hoekema, L., Nicolaes, G. A., Hemker, H. C., Tans, G. & Rosing, J. (1997) *Biochemistry* 36, 3331-3335.
28. Gale, A. J., Heeb, M. J. & Griffin, J. H. (2000) *Blood* 96, 585-593.
29. Nicolaes, G. A., Villoutreix, B. O. & Dahlback, B. (1999) *Biochemistry* 38, 13584-13591.
30. Krishnaswamy, S., Church, W. R., Nesheim, M. E. & Mann, K. G. (1987) *J. Biol. Chem.* 262, 3291-3299.
31. Hockin, M. F., Cawthern, K. M., Kalafatis, M. & Mann, K. G. (1999) *Biochemistry* 38, 6918-6934.
32. Bauer, K. A., Kass, B. L., ten Cate, H., Bednarek, M. A., Hawiger, J. J. & Rosenberg, R. D. (1989) *Blood* 74, 2007-2015.
33. Walker, F. J., Sexton, P. W. & Esmon, C. T. (1979) *Biochim. Biophys. Acta* 571, 333-342.
34. Nesheim, M. E., Canfield, W. M., Kisiel, W. & Mann, K. G. (1982) *J. Biol. Chem.* 257, 1443-1447.
35. Suzuki, K., Stenflo, J. A., Dahlback, B. & Teodorsson, B. (1983) *J. Biol. Chem.* 258, 1914-1920.
36. Rosing, J., Hoekema, L., Nicolaes, G. A. F., Thomassen, M. C. L. G. D., Hemker, H. C., Varadi, K., Schwarz, H. P. & Tans, G. (1995) *J. Biol. Chem.* 270, 27852-27858.
37. Lollar, P. & Parker, C. G. (1990) *J. Biol. Chem.* 265, 1688-1692.
38. Fay, P. J., Haidaris, P. J. & Srnudzin, T. M. (1991) *J. Biol. Chem.* 266, 8957-8962.
39. Lollar, P., Knutson, G. J. & Fass, D. N. (1984) *Blood* 63, 1303-1308.

40. Fay, P. J., Beattie, T. L., Regan, L. M., O'Brien, L. M. & Kaufinan, R. J. (1996) *J. Biol. Chen.* 271, 6027-6032.
41. Lollar; J. S. U.S. Pat. No. 6,180,371
42. Hackeng, T. M., Tans, G., Koppelman, S. J., De Groot, P. G., Rosing, J. & Bouma B. N. (1996) Biochem. J. 319, 399-405.
43. Cote, H. C. F., Bajzar, L., Stevens, W. K., Samis, J. A., Morser, J, MacGillivray, R. T. A. & Nesheim, M. E. (1997) J. Biological Chem 272, 6194-6200.
44. DeLa Cadena, R. A., Wachtfogel, Y. T. & Colman R. W. (1994)
45. Colman, R. W. (1999) Thromb Haemost 82, 1568-1577.
46. Shimomura, T. et al (1993) JBC 268:22927-32.
47. Miyazawa, K., et al (1993) JBC268, 10024-8.
48. Miyazawa K, Wang Y, Minoshima S, Shimizu N & Kitamura N. (1998) Eur J Biochem 258, 355-361.
49. Choi-Miura, N-H et al (1996) J. Biochem 119, 1157-1165.
50. Romisch, J et al (1999a) Blood Coagul Fibrinolysis 10, 471-9.
51. Romisch, J et al (1999b) Haemostasis 29, 292-9.
52. Lollar; J. S. U.S. Pat. No. 5,859,204.
53. High K A. (2001). Circ Res 88,137-144.
54. Walter J., High K A. (1997). Adv Vet Med 40, 119-134.
55. Pemberton, S., Lindley, P., Zaitsev, V., Card, G., Tuddenham, E. G. D., Kemball-Cook, G. (1997) Blood 89, 2413-2421
56. Arni R. K. et al (1993) Biochemistry 32, 4727-4737.
57. Hazes, B. & Dijkstra, B. W. (1988) Protein Engineering 2, 119-125.
58. Kohn, D. B., and P. W. Kantoff, (1989) 29 Transfusion 812-820.
59. Kay M A, Rothenberg S, Laden C N, Bellinger D A, Leland F, Toman C, Finegold M, Thompson A R, Read M S, Brinkhous K M, Woo S L C. In vivo gene therapy of hemphilia B: sustained partial correction in factor IX-deficient dogs. Science. 1993; 262: 117-119.
60. Vanden Driessche T, Vanslembrouck V, Goovaerts I, Zwinnen H, Vanderhaeghen M-L, Colen D, Chuah M K L. Long-term expression of human coagulation factor VIII and correction of hemophilia A after in vivo retroviral gene transfer in factor VIII-deficient mice. Proc Natl Acad Sci U S A. 1999; 96:9973-9975.
61. Bosch A, McCray P B, Chang S M, Ulich T R, Simonet W S, Jolly D J, Davidson B L. Proliferation induced by keratinocyte growth factor enhances in vivo retroviral-mediated gene transfer to mouse hepatocytes. J Clin Invest. 1996; 98:2683-2687.
62. Gao C, Jokerst R, Gondipalli P, Cai S-R, Kennedy S, Ponder K P. Intramuscular injection of an adenoviral vector expressing hepatocyte growth factor facilities hepatic transduction with a retroviral vector in mice. Hum Gene Ther. 1999; 10:911-922.
63. Synder R O, Miao C H, patijin G A, Spratt S K, Danos O, Nagy D, Gown A M, Winther B, Meuse L, Cohen L K, Thompson A R, Kay M A. Persistent and therapeutic concentrations of human factor IX in mice after hepatic gene transfer of recombinant AAV vectors. Nat Genet. 1997: 16:270-276.
64. Xiao X, Li J, Samulski R J. Efficient long-term gene transfer into muscle tissue of immunocompetent mice by adeno-associated virus vector. J Virol. 1996; 70:8098-8108.
65. Kessler P d, Podsakoff G M, Chen X, McQuiston S A, Colosi P C, Matelis L A, Kurtzman G J, Bryne B J. Gene delivery to skeletal muscle results in sustained expression and systemic delivery of a therapeutic protein. Proc Natl Acad Sci U S A. 1996; 93: 14082-14087
66. Herzog R W, Yang E Y, Couto L B, Hagstrom J N, Elwell D, Fields P A, Burton M, Bellinger D A, Read M S, Brinkhous K M, Podsakoff G M, Nichols T C, Kutzman G J, High K A. Long-term correction of canine hemophilia B by gene transfer of blood coagulation factor IX mediated by adeno-associates viral vector. Nat Med. 1999; 5:56-63.
67. Herzog R W, Hagstrom J N, Kung Z-H, Tai S J, Wilson J M, Fisher K J, High K A. Stable gene transfer and expression of human blood coagulation factor IX after intramuscular injection of recombinant adeno associated virus. Proc Natl Acad Sci U S A. 1997; 94: 5804-5809.
68. Kay M X, Manno C S, Ragni M V, Larson P J, Couto L B, McClelland A, Glader N, Chew A J, Tai S J, Herzog R W, Arruda V, Jolmson F, Scallan C, Skarsgard E, Flake A W, Higgh K A. Evidence for gene transfer and expression of factor IX in haemophilia B patients treated with an AAV vector. Nat Genet. 2000; 24: 257-261.
69. Xiao W, Chirmule N, Berta S C, McCullough B, Gao G, Wilson J M. Gene therapy vectors based on adeno-associated virus type 1. J Virol. 1999; 73: 3994-4003.
70. Chao H, Liu Y, Rabinowitz J, Li C, Samulski R J, Walsh C E. Several log increase in therapeutic transgene delivery by distinct adeno-associates viral serotype vectorss. Mol Ther. 2000; 2:619-623
71. Snyder Ro, Miao C, Meuse L, Tubb J, Donahue B A, Lin H-F, Stafford D W, Patel S, Thompson A R, Nichols T, Read M S, Bellinger D A, Brinkhous K M, Kay M A. Correction of hemophilia B in canine and murine models using recombinant adeno-associated viral vectors. Nat Med. 1999; 5:64-70.
72. Wang L, Nichols T C, Read M S, Bellinger D A, Verma I M. Sustained expression of therapeutic level of factor IX in hemophilia B dogs by AAV-mediated gene therapy in liver. Mol Ther. 2000; 1:154-158.
73. Herzog R W, Mount M J, Arruda V R, Tillson M, High K A. Sustained correction of canine hemophilia B by gene therapy in context of a null mutation. Blood. 2000; 96 (suppl.):798a. Abstract.
74. Nakai H, Ohashi K, Arruda V, McClelland A, Couto L B, Mause L, Storm rAA V-liver directed clinical trial for hemophilia B. Blood. 2000; 96(suppl.):798a. Abstract.
75. Lozier J N, Donahue R E, Donahue B A, Metzgert M E, McGehee J, Snydeeeer R O, Powell S, Winters P, Morgan R A. AAV-mediated expression of human factor IX in rhesus macaques. Mol Ther. 2000; 1:S289. Abstract.
76. Chirmule N, Propert K J, Magosin S A, Qian Y, Qian R, Wilson J M. Immune responses to adenovirus and adeno-associated virus vectors in humans. Gene Ther. 1999; 6:1574-1583.
77. Burton M, Nakai H, Colosi P, Cunningham J, Mitchell R, Couto L. vectors produces biologically active protein. Proc Nat Acad Sci U S A. 1999; 95: 12725-12730.
78. Chao H, Mao L, Bruce A T, Walsh C E. Sustained expression of human factor VIII in mice using a parvovirus-based vector. Blood. 2000; 95: 1594-1599.
79. Duan D, Yue Y, Yan Z, Engelhardt T F. A new dual-vector approach to enhance recombinant adeno-associated virus mediated gene expression through intermolecular cis activation. Nat Med. 2000; 6: 595-598.
80. Arruda V R, Hagstrom J N, Deitch J, Heiman-Patterson T, Chu K, Fileds P A, Herzog R W, Couto L B, Larson P J, High K A. Post-translational modifications of recombinant myotube-synthesized human factor IX. Blood. 2001; 97:130-138.

81. Kay M A, Landen C N, Rothenberg S R, Taylor L A, Leland F, Wiehle S, Fang B, Bellinger D, Finegold M, Thompson A R. In vivo heptic gene therapy: complete albeit transient correction of factor IX deficiency in hemophilia B dogs. Proc Natl Acad Sci USA. 1994; 91: 2253-2357.

82. Yang Y, Nunes F A, Berencsi K, Furth E E, Gonczol E, Wilson J M. Cellular innunity to viral antigens limits E1-deleted adenoviruses for gene therapy. Proc Natl Acad Sci U S A 1994; 91:4407-4411.

83. Kay M A, Meuse L, Gown A M, Linsley P, Hollenbaugh D, Aruffo A, Ochs H D, Wilson C B. Transcient immunomodulation with anti-CD40 ligand antibody and CTLA4Ig enhances persistence and secondary adenovirus-mediated gene transfer into mouse liver. Proc Natl Acad Sci U S A. 1997; 94: 4686-4691.

84. Connelly S, Smith T A, Dhir G, Gardner J M, Mehaffey M G, Zaret K S, McClelland A, Kaleko M. In vivo delivery and expression of physiological levels of functional human factor VIII in mice. Hum Gene Ther. 1995; 6:185-193.

85. Connelly S, Gardner J M, McClelland A, Kaleko M. Sustained expression of therapeutic levels of human factor VIII in mice. Blood. 1996; 87: 4671-4677.

86. Connelly S, Gardner J M, McClelland A, Kaleko M. High-level tissue specific expression of functional human factor VIII in mice. Hum Gene Ther. 1996; 7: 183-195.

87. Connelly S, Mount J, Mauser A, Gardner J M, Kaleko M, McClelland A, Lotlhrop C D. Complete short-term correction of canine hemophilia A by in vivo gene therapy. Blood. 1996; 88: 3846-3853.

88. Connelly S, Andrews J L, Gallo A M, Kayda D B, Qian J, Hoyer L, Kadan M J, Gorziglia M I, Trapnell B C, McClelland A, Kaleko M. Sustained phenotypic correction of murine hemophilia A by vivo gene therapy. Blood. 1998; 91: 3273-3281.

89. Gallo-Penn A M, Shirley P S, Andrews J L, Tinlin S, Webster S, Cameron C, Hough C, Notley C, Lillicrap D, Kaleko M, Connelly S. Systemic delivery of an adenoviral vector encoding canine factor VIII results in short-term phenotypic correction, inhibitor development, and biphasic liver toxicity in hemophilia A dogs. Blood. 2001; 97: 107-113.

90. Morral N, O'Neal W K, Rice R, Leland M, Kaplan J, Piedra P A, Zhou H, Parks R J, Velji R, Auilar-Cordova E, Wadsworth S, Graham F L, Kochanek S, Carey K D, Baudet Al. Administration of helper-dependent adenoviral vectors and sequential delivery of different vector serotype for long-term liver-directed gene transfer in baboons. Proc Natl Acad Sci U S A. 1999; 96: 12816-12821.

91. Schiedner G, Morral N, Parks R J, Wu Y, Koopmans S C, Langston C, Graham F L, Beaudet A L, Kochnek S. Genomic DNA transfer with a high-capacity adenovirus vector results in improved in vivo gene expression and decreased toxicity. Nat. Genet. 1998; 18: 180-183.

92. Clemens P R, Kochanek S, Sunada Y, Chan S, Chen H H, Campbell K P, Caskey C T. In vivo muscle gene transfer of full-length dystrophin with an adenoviral vector that lacks all viral genes. Gene Ther. 1996; 3:965-972.

93. Haecker S E, Stedman H H, Balice-Gordon R J, Smith D B, Greelish J P, full-length human dystrophin from adenoviral vectors deleted of all viral genes. Hum Gene Ther. 1996; 7:1907-1914.

94. Kumar-Sigrih R, Chamberlain J S. Encapisidated adenovirus minichromosomes allow delivery and expression of a 14 kb dystrophin cDNA to muscle cells. Hum Mol Genet. 1996; 5:913-921.

95. Chen H H, Mack L M, Kelly R, Ontell M, Kochanek S, Clemens P R. Persistence in muscle of an adenoviral vector that lacks all viral genes. Proc Natl Acad Sci USA 1997; 94:1645-1650

96. Morsy M A, Gu M, Motzel S, Zhao J, Lin J, Su Q, Allen H, Franlin L, Parks R J, Graham F L, Kochanek S, Bett A J, Caskey C T. An adenoviral vector deleted for all viral coding sequences results in enhanced safety and extended expression of a leptin transgene. Proc Natl Acad Sci USA. 1998; 95:7866-7871.

97. Balague C, Zhou J, Dai Y, Alemany R, Josephs S F, Andreason G, Harlharan M, Sethi E, Prokepenko E, Jan H-Y, Lou Y-C, Hubert-Leslie D, Ruiz L, Zhang W W. Sustained high-level expression of full-length human facto VIII and restoration of clotting activity in hemophilic mice using a minimal adenovirus vector. Blood. 2000; 95:820-828.

98. Morral N, Parks R J, Zhou H, Langston C, Schiedner G, Quinones J, Grahma F L, Lochanek S, Beaudet A L. High doses of a helper-dependent adenoviral vectors yield supraphysiological levels of a-antitrypsin with negligible toxicity. Hum Gene Ther. 1998; 9:2709-2716.

99. Wilson J M. Innate and acquired immunity to vectors. Paper presented at: Keystone Symposia on Gene Therapy: A Gene Odyssey; Jan. 6-11, 2001; Snowbird, Utah.

100. Bristol J A, Shirley P, Idamakanti N, Kaleko M, Connelly S. In vivo dose threshold effect of adenoviras-mediated factor VIII gene therapy in hemophiliac mice. Mol Ther. 2000; 2:223-232.

101. Reddy P S, Yan L, Pattison S, Sakhuja K, Kayda D, Golightly D, Indamakanti N, Oraefo M, Frann T, Lu P, Pinkstaff A, Kaloss M, Kaleko M, Connelly S. Generation and in vivo evaluation of a gutless adenoviral vector encoding human factor VIII. Paper presented at: Cold Spring Harbor Gene Therapy Meeting, Sep. 25-29, 2000; Cold Spring Harbor, N.Y.

102. Naldini L, Blomer U, Gallay P, Ory D, Mulligan R, Gage F H, Verma I M, Trono D. In vivo gene delivery and stable transduction of nondividing cells by a lentiviral vector. Science. 1996; 272: 263-267.

103. Kafri T, Blomer U, Peterson D A, Gage F H, Verma I M. Sustained expression of genes delivered directly into liver and muscle by lentiviral vectors. Nat Genet. 1997; 17: 314-317.

104. Park F, Ohashi K, Chiu W, M. N, Kay M A. Efficient lentiviral transduction of liver required cell cycling in vivo. Nat Genet. 2000; 24: 49-52.

105. Naldini L. Pre-clinical studies of lentiviral vectors: viral vectors for the treatment of hemophilia corporate symposium. In: Program of the American Society of Gene Therapy third annual meeting; May 31-Jun. 4, 2000; Denver, Colo.

106. Dull T, Zufferey R, Kelly M, Mandel R J, Nguyen M, Trono D, Naldini L. A third-generation lentivirus vector with a conditional packaging system. J Virol. 1998; 72: 8463-8471.

107. Okoli G, Hortelano G, Leong K. Oral delivery of plasmid DNA encoding the factor IX gene. Mol Ther. 2000; 1:S28. Abstract.

108. Roth D A, Tawa N E, O'Brien J M, Treco D A, Selden R F. Nonviral Transfer of the Gene Encoding Coagulation Factor VIII in Patients With Severe Hemophilia A. New England J. Med. 334, 1735-1742.

109. Martin P D, Malkowski M G, Box J, Esmon C T, Edwards B F. New insights into the regulation of the blood clotting cascade derived from the X-ray crystal structure of bovine meizothrombin des F1 in complex with PPACK. Structure 1997; 5:1681-1693.
110. Pipe, S W and Kaufman, R J. Characterization of a Genetically Engineered Inactivation Resistant Coagulation Factor VIIIa. Proc Natl Acad Sci USA. 1994; 11851-11856 (1997).
111. Boedeker, B. G. Production processes of licensed recombinant factor VIII preparations. Semin. Thromb. Hemost. 27(4):385-94 (August 2001)

Every reference cited here and throughout the application is hereby incorporated by reference in its entirety.

RAMIFICATIONS AND SCOPE

Changes may be made in the nature, composition, operation and arrangement of the various elements, steps and procedures described herein without departing from the spirit and scope of the invention as defined in the following claims. Modifications of the above described modes for carrying out the invention that are obvious to those of skill in the fields of genetic engineering, virology, hematology, medicine, and related fields are intended to be within the scope of the following claims.

The invention claimed is:

1. A method of stabilizing a Factor VIII polypeptide which is the product of a single gene in nature by introducing one or more cysteines comprising the steps of:
   (a) obtaining or creating a three-dimensional structure of said polypeptide;
   (b) predicting one or more sites for the introduction of one or more cysteines based on said structure; and
   (c) creating one or more mutants of said polypeptide by introducing one or more cysteines at one or more of said predicted sites;
wherein at least one pair of cysteines is located at residues: Met 662-Asp 1828; Ser 268-Phe 673; Ile 312-Pro 672; Ser 313-Ala 644; Met 662-Lys 1827; Tyr 664-Thr 1826; Pro 264-Gln 645; Arg 282-Thr 522; Ser 285-Phe 673; His 311-Phe 673; Ser 314-Ala 644; Ser 314-Gln 645; Val 663-Glu 1829; Asn 694-Pro 1980; or Ser 695-Glu 1844 of the Factor VIII polypeptide.

2. A method of stabilizing a Factor VIII polypeptide which is the product of a single gene in nature by introducing one or more cysteines comprising the steps of:
   (a) obtaining or creating a three-dimensional structure based on homology modeling of said polypeptide;
   (b) predicting one or more sites for the introduction of one or more cysteines based on the three dimensional structure; and
   (c) creating one or more mutants of said polypeptide by introducing one or more cysteines at one or more of said predicted sites;
wherein at least one pair of cysteines is located at residues: Met 662-Asp 1828; Ser 268-Phe 673; Ile 312-Pro 672; Ser 313-Ala 644; Met 662-Lys 1827; Tyr 664-Thr 1826; Pro 264-Gln 645; Arg 282-Thr 522; Ser 285-Phe 673; His 311-Phe 673; Ser 314-Ala 644; Ser 314-Gln 645; Val 663-Glu 1829; Asn 694-Pro 1980; or Ser 695-Glu 1844 of the Factor VIII polypeptide.

3. The method of claim 1, wherein the introduction of said one or more cysteines permits the formation of at least one intramolecular, interdomain disulfide bridge which increases the stability of the mutant polypeptide as compared to that of the polypeptide which does not contain said introduced one or more cysteines, thereby avoiding disassociation of the polypeptide.

4. The method of claim 2, wherein the introduction of said one or more cysteines permits the formation of at least one intramolecular, interdomain disulfide bridge which increases the stability of the mutant polypeptide as compared to that of the polypeptide which does not contain said introduced one or more cysteines, thereby avoiding disassociation of the polypeptide.

* * * * *

```
SEQUENCE LISTING

<160> NUMBER OF SEQ ID NOS: 32

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 1
cacggatcct acagattaca ttgagatca                                29

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 2
gtctggatcc ctgtgattat gacttccttt tgcatgtcca cctgaatcca ag       52

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
catggaatca agctattaca cttcgcc                                  27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ggcgaagtgt aatagcttga ttccatg                                  27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
ggccagaatg cttctccatt c                                        21
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
gaatggagaa gcattctggc c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
gtggggacct gtaatgaaat t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
aatttcatta caggtcccca c                                              21

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
ctatggaaag aggtgtgagg acacc                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
ggtgtcctca cacctctttc catag                                          25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
gatcagggcc atgtagtcct ggc                                            23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
```
gccaggacta catggccctg atc                                                    23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
ccaaagaaaa cccagaatct taag                                                   24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
cttaagattc tgggttttct ttgg                                                   24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 15
ctggacaggc aaggaataca g                                                      21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 16
ctgtattcct tgcctgtcca g                                                      21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 17
catggctaca cagaaaatgc atg                                                    23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 18
catgcatttt ctgtgtagcc atg                                                    23

<210> SEQ ID NO 19
<211> LENGTH: 38
<212> TYPE: DNA
<213> ORGANISM: Artificial Sequence

```
<220> FEATURE:
<223> OTHER INFORMATION: Description of Artificial Sequence: Primer

<400> SEQUENCE: 19
ccttcaaaca caaatgcgtc tatgaagaca cactcacc                              38

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 20
ggtgagtgtg tcttcataga cgcatttgtg tttgaagg                              38

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
ggcacccact aaatgtgagt ttgactgcaa agc                                   33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 22
gctttgcagt caaactcaca tttagtgggt gcc                                   33

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 23
cacaaaatgg tctgtgaaga cacactcacc c                                     31

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 24
gggtgagtgt gtcttcacag aggattttgt g                                     31

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 25
catatggcac cctgtaaaga tgagtttgac tgc                                   33
```

```
<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26
gcagtcaaac tcatctttac agggtgccat atg                              33

<210> SEQ ID NO 27
<211> LENGTH: 2351
<212> TYPE: PRT
<213> ORGANISM: Homo sapiens

<400> SEQUENCE: 27
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His

-continued

```
                325                 330                 335
Asp Gly Met Glu Ala Tyr Val Lys Val Asp Ser Cys Pro Glu Pro
                340                 345                 350
Gln Leu Arg Met Lys Asn Asn Glu Glu Ala Glu Asp Tyr Asp Asp
                355                 360                 365
Leu Thr Asp Ser Glu Met Asp Val Val Arg Phe Asp Asp Asn Ser
                370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
                450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
                530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
                610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
                690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
```

-continued

```
Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
        770                 775                 780

Ile Glu Lys Thr Asp Pro Trp Phe Ala His Arg Thr Pro Met Pro Lys
785                 790                 795                 800

Ile Gln Asn Val Ser Ser Asp Leu Leu Met Leu Leu Arg Gln Ser
                    805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
        850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
        930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser Asn
        1010                1015                1020

Asn Ser Ala Thr Asn Arg Lys Thr His Ile Asp Gly Pro Ser Leu Leu
1025                1030                1035                1040

Ile Glu Asn Ser Pro Ser Val Trp Gln Asn Ile Leu Glu Ser Asp Thr
                    1045                1050                1055

Glu Phe Lys Lys Val Thr Pro Leu Ile His Asp Arg Met Leu Met Asp
                1060                1065                1070

Lys Asn Ala Thr Ala Leu Arg Leu Asn His Met Ser Asn Lys Thr Thr
        1075                1080                1085

Ser Ser Lys Asn Met Glu Met Val Gln Gln Lys Lys Glu Gly Pro Ile
        1090                1095                1100

Pro Pro Asp Ala Gln Asn Pro Asp Met Ser Phe Phe Lys Met Leu Phe
1105                1110                1115                1120

Leu Pro Glu Ser Ala Arg Trp Ile Gln Arg Thr His Gly Lys Asn Ser
                1125                1130                1135

Leu Asn Ser Gly Gln Gly Pro Ser Pro Lys Gln Leu Val Ser Leu Gly
            1140                1145                1150

Pro Glu Lys Ser Val Glu Gly Gln Asn Phe Leu Ser Glu Lys Asn Lys
        1155                1160                1165

Val Val Val Gly Lys Gly Glu Phe Thr Lys Asp Val Gly Leu Lys Glu
1170                1175                1180
```

```
Met Val Phe Pro Ser Ser Arg Asn Leu Phe Leu Thr Asn Leu Asp Asn
1185                1190                1195                1200

Leu His Glu Asn Asn Thr His Asn Gln Glu Lys Lys Ile Gln Glu Glu
            1205                1210                1215

Ile Glu Lys Lys Glu Thr Leu Ile Gln Glu Asn Val Val Leu Pro Gln
        1220                1225                1230

Ile His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr Ala
  1250                1255                1260

Pro Val Leu Gln Asp Phe Arg Ser Leu Asn Asp Ser Thr Asn Arg Thr
1265                1270                1275                1280

Lys Lys His Thr Ala His Phe Ser Lys Lys Gly Glu Glu Glu Asn Leu
            1285                1290                1295

Glu Gly Leu Gly Asn Gln Thr Lys Gln Ile Val Glu Lys Tyr Ala Cys
        1300                1305                1310

Thr Thr Arg Ile Ser Pro Asn Thr Ser Gln Gln Asn Phe Val Thr Gln
    1315                1320                1325

Arg Ser Lys Arg Ala Leu Lys Gln Phe Arg Leu Pro Leu Glu Glu Thr
  1330                1335                1340

Glu Leu Glu Lys Arg Ile Ile Val Asp Asp Thr Ser Thr Gln Trp Ser
1345                1350                1355                1360

Lys Asn Met Lys His Leu Thr Pro Ser Thr Leu Thr Gln Ile Asp Tyr
            1365                1370                1375

Asn Glu Lys Glu Lys Gly Ala Ile Thr Gln Ser Pro Leu Ser Asp Cys
        1380                1385                1390

Leu Thr Arg Ser His Ser Ile Pro Gln Ala Asn Arg Ser Pro Leu Pro
    1395                1400                1405

Ile Ala Lys Val Ser Ser Phe Pro Ser Ile Arg Pro Ile Tyr Leu Thr
  1410                1415                1420

Arg Val Leu Phe Gln Asp Asn Ser Ser His Leu Pro Ala Ala Ser Tyr
1425                1430                1435                1440

Arg Lys Lys Asp Ser Gly Val Gln Glu Ser Ser His Phe Leu Gln Gly
            1445                1450                1455

Ala Lys Lys Asn Asn Leu Ser Leu Ala Ile Leu Thr Leu Glu Met Thr
        1460                1465                1470

Gly Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp Leu
  1490                1495                1500

Pro Lys Thr Ser Gly Lys Val Glu Leu Leu Pro Lys Val His Ile Tyr
1505                1510                1515                1520

Gln Lys Asp Leu Phe Pro Thr Glu Thr Ser Asn Gly Ser Pro Gly His
            1525                1530                1535

Leu Asp Leu Val Glu Gly Ser Leu Leu Gln Gly Thr Glu Gly Ala Ile
        1540                1545                1550

Lys Trp Asn Glu Ala Asn Arg Pro Gly Lys Val Pro Phe Leu Arg Val
    1555                1560                1565

Ala Thr Glu Ser Ser Ala Lys Thr Pro Ser Lys Leu Leu Asp Pro Leu
  1570                1575                1580

Ala Trp Asp Asn His Tyr Gly Thr Gln Ile Pro Lys Glu Glu Trp Lys
1585                1590                1595                1600

Ser Gln Glu Lys Ser Pro Glu Lys Thr Ala Phe Lys Lys Lys Asp Thr
```

Ile Leu Ser Leu Asn Ala Cys Glu Ser Asn His Ala Ile Ala Ala Ile
1620                1625                1630

Asn Glu Gly Gln Asn Lys Pro Glu Ile Glu Val Thr Trp Ala Lys Gln
1635                1640                1645

Gly Arg Thr Glu Arg Leu Cys Ser Gln Asn Pro Val Leu Lys Arg
1650                1655                1660

His Gln Arg Glu Ile Thr Arg Thr Thr Leu Gln Ser Asp Gln Glu Glu
1665                1670                1675                1680

Ile Asp Tyr Asp Asp Thr Ile Ser Val Glu Met Lys Lys Glu Asp Phe
            1685                1690                1695

Asp Ile Tyr Asp Glu Asp Glu Asn Gln Ser Pro Arg Ser Phe Gln Lys
            1700                1705                1710

Lys Thr Arg His Tyr Phe Ile Ala Ala Val Glu Arg Leu Trp Asp Tyr
            1715                1720                1725

Gly Met Ser Ser Ser Pro His Val Leu Arg Asn Arg Ala Gln Ser Gly
            1730                1735                1740

Ser Val Pro Gln Phe Lys Lys Val Val Phe Gln Glu Phe Thr Asp Gly
1745                1750                1755                1760

Ser Phe Thr Gln Pro Leu Tyr Arg Gly Glu Leu Asn Glu His Leu Gly
            1765                1770                1775

Leu Leu Gly Pro Tyr Ile Arg Ala Glu Val Glu Asp Asn Ile Met Val
            1780                1785                1790

Thr Phe Arg Asn Gln Ala Ser Arg Pro Tyr Ser Phe Tyr Ser Ser Leu
            1795                1800                1805

Ile Ser Tyr Glu Glu Asp Gln Arg Gln Gly Ala Glu Pro Arg Lys Asn
            1810                1815                1820

Phe Val Lys Pro Asn Glu Thr Lys Thr Tyr Phe Trp Lys Val Gln His
1825                1830                1835                1840

His Met Ala Pro Thr Lys Asp Glu Phe Asp Cys Lys Ala Trp Ala Tyr
            1845                1850                1855

Phe Ser Asp Val Asp Leu Glu Lys Asp Val His Ser Gly Leu Ile Gly
            1860                1865                1870

Pro Leu Leu Val Cys His Thr Asn Thr Leu Asn Pro Ala His Gly Arg
            1875                1880                1885

Gln Val Thr Val Gln Glu Phe Ala Leu Phe Phe Thr Ile Phe Asp Glu
            1890                1895                1900

Thr Lys Ser Trp Tyr Phe Thr Glu Asn Met Glu Arg Asn Cys Arg Ala
1905                1910                1915                1920

Pro Cys Asn Ile Gln Met Glu Asp Pro Thr Phe Lys Glu Asn Tyr Arg
            1925                1930                1935

Phe His Ala Ile Asn Gly Tyr Ile Met Asp Thr Leu Pro Gly Leu Val
            1940                1945                1950

Met Ala Gln Asp Gln Arg Ile Arg Trp Tyr Leu Leu Ser Met Gly Ser
            1955                1960                1965

Asn Glu Asn Ile His Ser Ile His Phe Ser Gly His Val Phe Thr Val
            1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
            2005                2010                2015

Val Glu Cys Leu Ile Gly Glu His Leu His Ala Gly Met Ser Thr Leu
            2020                2025                2030

```
Phe Leu Val Tyr Ser Asn Lys Cys Gln Thr Pro Leu Gly Met Ala Ser
            2035                2040                2045

Gly His Ile Arg Asp Phe Gln Ile Thr Ala Ser Gly Gln Tyr Gly Gln
    2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
            2085                2090                2095

Pro Met Ile Ile His Gly Ile Lys Thr Gln Gly Ala Arg Gln Lys Phe
        2100                2105                2110

Ser Ser Leu Tyr Ile Ser Gln Phe Ile Ile Met Tyr Ser Leu Asp Gly
            2115                2120                2125

Lys Lys Trp Gln Thr Tyr Arg Gly Asn Ser Thr Gly Thr Leu Met Val
    2130                2135                2140

Phe Phe Gly Asn Val Asp Ser Ser Gly Ile Lys His Asn Ile Phe Asn
2145                2150                2155                2160

Pro Pro Ile Ile Ala Arg Tyr Ile Arg Leu His Pro Thr His Tyr Ser
            2165                2170                2175

Ile Arg Ser Thr Leu Arg Met Glu Leu Met Gly Cys Asp Leu Asn Ser
        2180                2185                2190

Cys Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser Pro
    2210                2215                2220

Ser Lys Ala Arg Leu His Leu Gln Gly Arg Ser Asn Ala Trp Arg Pro
2225                2230                2235                2240

Gln Val Asn Asn Pro Lys Glu Trp Leu Gln Val Asp Phe Gln Lys Thr
            2245                2250                2255

Met Lys Val Thr Gly Val Thr Thr Gln Gly Val Lys Ser Leu Leu Thr
        2260                2265                2270

Ser Met Tyr Val Lys Glu Phe Leu Ile Ser Ser Ser Gln Asp Gly His
            2275                2280                2285

Gln Trp Thr Leu Phe Phe Gln Asn Gly Lys Val Lys Val Phe Gln Gly
    2290                2295                2300

Asn Gln Asp Ser Phe Thr Pro Val Val Asn Ser Leu Asp Pro Pro Leu
2305                2310                2315                2320

Leu Thr Arg Tyr Leu Arg Ile His Pro Gln Ser Trp Val His Gln Ile
            2325                2330                2335

Ala Leu Arg Met Glu Val Leu Gly Cys Glu Ala Gln Asp Leu Tyr
        2340                2345                2350

<210> SEQ ID NO 28
<211> LENGTH: 655
<212> TYPE: PRT
<213> ORGANISM: Homo sapiens

<400> SEQUENCE: 28

Met Gly Arg Trp Ala Trp Val Pro Ser Pro Trp Pro Pro Gly Leu
1               5                   10                  15

Gly Pro Phe Leu Leu Leu Leu Leu Leu Leu Leu Leu Pro Arg Gly
            20                  25                  30

Phe Gln Pro Gln Pro Gly Gly Asn Arg Thr Glu Ser Pro Glu Pro Asn
        35                  40                  45

Ala Thr Ala Thr Pro Ala Ile Pro Thr Ile Leu Val Thr Ser Val Thr
    50                  55                  60
```

-continued

```
Ser Glu Thr Pro Ala Thr Ser Ala Pro Glu Ala Gly Pro Gln Ser
 65                  70                  75                  80

Gly Gly Leu Pro Pro Pro Arg Ala Val Pro Ser Ser Ser Ser Pro
                 85                  90                  95

Gln Ala Gln Ala Leu Thr Glu Asp Gly Arg Pro Cys Arg Phe Pro Phe
            100                 105                 110

Arg Tyr Gly Gly Arg Met Leu His Ala Cys Thr Ser Glu Gly Ser Ala
        115                 120                 125

His Arg Lys Trp Cys Ala Thr Thr His Asn Tyr Asp Arg Asp Arg Ala
    130                 135                 140

Trp Gly Tyr Cys Val Glu Ala Thr Pro Pro Gly Gly Pro Ala Ala
145                 150                 155                 160

Leu Asp Pro Cys Ala Ser Gly Pro Cys Leu Asn Gly Gly Ser Cys Ser
                165                 170                 175

Asn Thr Gln Asp Pro Gln Ser Tyr His Cys Ser Cys Pro Arg Ala Phe
            180                 185                 190

Thr Gly Lys Asp Cys Gly Thr Glu Lys Cys Phe Asp Glu Thr Arg Tyr
        195                 200                 205

Glu Tyr Leu Glu Gly Gly Asp Arg Trp Ala Arg Val Arg Gln Gly His
210                 215                 220

Val Glu Gln Cys Glu Cys Phe Gly Gly Arg Thr Trp Cys Glu Gly Thr
225                 230                 235                 240

Arg His Thr Ala Cys Leu Ser Ser Pro Cys Leu Asn Gly Gly Thr Cys
                245                 250                 255

His Leu Ile Val Ala Thr Gly Thr Thr Val Cys Ala Cys Pro Pro Gly
            260                 265                 270

Phe Ala Gly Arg Leu Cys Asn Ile Glu Pro Asp Glu Arg Cys Phe Leu
        275                 280                 285

Gly Asn Gly Thr Gly Tyr Arg Gly Val Ala Ser Thr Ser Ala Ser Gly
            290                 295                 300

Leu Ser Cys Leu Ala Trp Asn Ser Asp Leu Leu Tyr Gln Glu Leu His
305                 310                 315                 320

Val Asp Ser Val Gly Ala Ala Leu Leu Gly Leu Gly Pro His Ala
                325                 330                 335

Tyr Cys Arg Asn Pro Asp Asn Asp Glu Arg Pro Trp Cys Tyr Val Val
        340                 345                 350

Lys Asp Ser Ala Leu Ser Trp Glu Tyr Cys Arg Leu Glu Ala Cys Glu
            355                 360                 365

Ser Leu Thr Arg Val Gln Leu Ser Pro Asp Leu Leu Ala Thr Leu Pro
        370                 375                 380

Glu Pro Ala Ser Pro Gly Arg Gln Ala Cys Gly Arg Arg His Lys Lys
385                 390                 395                 400

Arg Thr Phe Leu Arg Pro Arg Ile Ile Gly Gly Ser Ser Ser Leu Pro
                405                 410                 415

Gly Ser His Pro Trp Leu Ala Ala Ile Tyr Ile Gly Asp Ser Phe Cys
            420                 425                 430

Ala Gly Ser Leu Val His Thr Cys Trp Val Ser Ala Ala His Cys
        435                 440                 445

Phe Ser His Ser Pro Pro Arg Asp Ser Val Ser Val Val Leu Gly Gln
450                 455                 460

His Phe Phe Asn Arg Thr Thr Asp Val Thr Gln Thr Phe Gly Ile Glu
465                 470                 475                 480

Lys Tyr Ile Pro Tyr Thr Leu Tyr Ser Val Phe Asn Pro Ser Asp His
            485                 490                 495
```

```
Asp Leu Val Leu Ile Arg Leu Lys Lys Lys Gly Asp Arg Cys Ala Thr
                500                 505                 510

Arg Ser Gln Phe Val Gln Pro Ile Cys Leu Pro Glu Pro Gly Ser Thr
            515                 520                 525

Phe Pro Ala Gly His Lys Cys Gln Ile Ala Gly Trp Gly His Leu Asp
        530                 535                 540

Glu Asn Val Ser Gly Tyr Ser Ser Leu Arg Glu Ala Leu Val Pro
545                 550                 555                 560

Leu Val Ala Asp His Lys Cys Ser Ser Pro Glu Val Tyr Gly Ala Asp
                565                 570                 575

Ile Ser Pro Asn Met Leu Cys Ala Gly Tyr Phe Asp Cys Lys Ser Asp
            580                 585                 590

Ala Cys Gln Gly Asp Ser Gly Gly Pro Leu Ala Cys Glu Lys Asn Gly
        595                 600                 605

Val Ala Tyr Leu Tyr Gly Ile Ile Ser Trp Gly Asp Gly Cys Gly Arg
    610                 615                 620

Leu His Lys Pro Gly Val Tyr Thr Arg Val Ala Asn Tyr Val Asp Trp
625                 630                 635                 640

Ile Asn Asp Arg Ile Arg Pro Pro Arg Arg Leu Val Ala Pro Ser
                645                 650                 655

<210> SEQ ID NO 29
<211> LENGTH: 622
<212> TYPE: PRT
<213> ORGANISM: Homo sapiens

<400> SEQUENCE: 29

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220
```

```
Leu Ala Val Thr Thr His Gly Leu Pro Cys Leu Ala Trp Ser Ala
225                 230                 235                 240

Gln Ala Lys Ala Leu Ser Lys His Gln Asp Phe Asn Ser Ala Val Gln
            245                 250                 255

Leu Val Glu Asn Phe Cys Arg Asn Pro Asp Gly Asp Glu Glu Gly Val
        260                 265                 270

Trp Cys Tyr Val Ala Gly Lys Pro Gly Asp Phe Gly Tyr Cys Asp Leu
    275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
610                 615                 620

<210> SEQ ID NO 30
<211> LENGTH: 615
<212> TYPE: PRT
```

<213> ORGANISM: Homo sapiens

<400> SEQUENCE: 30

```
Met Arg Ala Leu Leu Leu Gly Phe Leu Leu Val Ser Leu Glu Ser
 1               5                  10                  15

Thr Leu Ser Ile Pro Pro Trp Glu Ala Pro Lys Glu His Lys Tyr Lys
            20                  25                  30

Ala Glu His Thr Val Val Leu Thr Val Thr Gly Glu Pro Cys His
        35                  40                  45

Phe Pro Phe Gln Tyr His Arg Gln Leu Tyr His Lys Cys Thr His Lys
        50                  55                  60

Gly Arg Pro Gly Pro Gln Pro Trp Cys Ala Thr Thr Pro Asn Phe Asp
 65                 70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
        130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Pro Phe
        195                 200                 205

Cys Asp Val Asp Thr Lys Ala Ser Cys Tyr Asp Gly Arg Gly Leu Ser
210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
        290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
        370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
```

```
                    405                 410                 415
Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
        435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
        515                 520                 525

Leu Glu Arg Cys Ser Ala Pro Asp Val His Gly Ser Ser Ile Leu Pro
    530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
        595                 600                 605

Ile Arg Glu His Thr Val Ser
    610                 615

<210> SEQ ID NO 31
<211> LENGTH: 2224
<212> TYPE: PRT
<213> ORGANISM: Homo sapiens

<400> SEQUENCE: 31

Met Phe Pro Gly Cys Pro Arg Leu Trp Val Leu Val Val Leu Gly Thr
1               5                   10                  15

Ser Trp Val Gly Trp Gly Ser Gln Gly Thr Glu Ala Ala Gln Leu Arg
            20                  25                  30

Gln Phe Tyr Val Ala Ala Gln Gly Ile Ser Trp Ser Tyr Arg Pro Glu
        35                  40                  45

Pro Thr Asn Ser Ser Leu Asn Leu Ser Val Thr Ser Phe Lys Lys Ile
    50                  55                  60

Val Tyr Arg Glu Tyr Glu Pro Tyr Phe Lys Lys Glu Lys Pro Gln Ser
65                  70                  75                  80

Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
        115                 120                 125

Leu Asp His Thr Phe Pro Ala Glu Lys Met Asp Asp Ala Val Ala Pro
    130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
```

-continued

```
                165                 170                 175
Asn Leu Ile Glu Asp Phe Asn Ser Gly Leu Ile Gly Pro Leu Leu Ile
            180                 185                 190
Cys Lys Lys Gly Thr Leu Thr Glu Gly Gly Thr Gln Lys Thr Phe Asp
            195                 200                 205
Lys Gln Ile Val Leu Leu Phe Ala Val Phe Asp Glu Ser Lys Ser Trp
            210                 215                 220
Ser Gln Ser Ser Ser Leu Met Tyr Thr Val Asn Gly Tyr Val Asn Gly
225                 230                 235                 240
Thr Met Pro Asp Ile Thr Val Cys Ala His Asp His Ile Ser Trp His
                245                 250                 255
Leu Leu Gly Met Ser Ser Gly Pro Glu Leu Phe Ser Ile His Phe Asn
                260                 265                 270
Gly Gln Val Leu Glu Gln Asn His His Lys Val Ser Ala Ile Thr Leu
                275                 280                 285
Val Ser Ala Thr Ser Thr Thr Ala Asn Met Thr Val Gly Pro Glu Gly
                290                 295                 300
Lys Trp Ile Ile Ser Ser Leu Thr Pro Lys His Leu Gln Ala Gly Met
305                 310                 315                 320
Gln Ala Tyr Ile Asp Ile Lys Asn Cys Pro Lys Lys Thr Arg Asn Leu
                325                 330                 335
Lys Lys Ile Thr Arg Glu Gln Arg Arg His Met Lys Arg Trp Glu Tyr
                340                 345                 350
Phe Ile Ala Ala Glu Glu Val Ile Trp Asp Tyr Ala Pro Val Ile Pro
                355                 360                 365
Ala Asn Met Asp Lys Lys Tyr Arg Ser Gln His Leu Asp Asn Phe Ser
                370                 375                 380
Asn Gln Ile Gly Lys His Tyr Lys Lys Val Met Tyr Thr Gln Tyr Glu
385                 390                 395                 400
Asp Glu Ser Phe Thr Lys His Thr Val Asn Pro Asn Met Lys Glu Asp
                405                 410                 415
Gly Ile Leu Gly Pro Ile Ile Arg Ala Gln Val Arg Asp Thr Leu Lys
                420                 425                 430
Ile Val Phe Lys Asn Met Ala Ser Arg Pro Tyr Ser Ile Tyr Pro His
                435                 440                 445
Gly Val Thr Phe Ser Pro Tyr Glu Asp Glu Val Asn Ser Ser Phe Thr
                450                 455                 460
Ser Gly Arg Asn Asn Thr Met Ile Arg Ala Val Gln Pro Gly Glu Thr
465                 470                 475                 480
Tyr Thr Tyr Lys Trp Asn Ile Leu Glu Phe Asp Glu Pro Thr Glu Asn
                485                 490                 495
Asp Ala Gln Cys Leu Thr Arg Pro Tyr Tyr Ser Asp Val Asp Ile Met
                500                 505                 510
Arg Asp Ile Ala Ser Gly Leu Ile Gly Leu Leu Leu Ile Cys Lys Ser
                515                 520                 525
Arg Ser Leu Asp Arg Arg Gly Ile Gln Arg Ala Ala Asp Ile Glu Gln
                530                 535                 540
Gln Ala Val Phe Ala Val Phe Asp Glu Asn Lys Ser Trp Tyr Leu Glu
545                 550                 555                 560
Asp Asn Ile Asn Lys Phe Cys Glu Asn Pro Asp Glu Val Lys Arg Asp
                565                 570                 575
Asp Pro Lys Phe Tyr Glu Ser Asn Ile Met Ser Thr Ile Asn Gly Tyr
                580                 585                 590
```

-continued

```
Val Pro Glu Ser Ile Thr Thr Leu Gly Phe Cys Phe Asp Asp Thr Val
            595                 600                 605
Gln Trp His Phe Cys Ser Val Gly Thr Gln Asn Glu Ile Leu Thr Ile
    610                 615                 620
His Phe Thr Gly His Ser Phe Ile Tyr Gly Lys Arg His Glu Asp Thr
625                 630                 635                 640
Leu Thr Leu Phe Pro Met Arg Gly Glu Ser Val Thr Val Thr Met Asp
                645                 650                 655
Asn Val Gly Thr Trp Met Leu Thr Ser Met Asn Ser Ser Pro Arg Ser
            660                 665                 670
Lys Lys Leu Arg Leu Lys Phe Arg Asp Val Lys Cys Ile Pro Asp Asp
        675                 680                 685
Asp Glu Asp Ser Tyr Glu Ile Phe Glu Pro Pro Glu Ser Thr Val Met
690                 695                 700
Ala Thr Arg Lys Met His Asp Arg Leu Glu Pro Glu Asp Glu Glu Ser
705                 710                 715                 720
Asp Ala Asp Tyr Asp Tyr Gln Asn Arg Leu Ala Ala Leu Gly Ile
                725                 730                 735
Arg Ser Phe Arg Asn Ser Ser Leu Asn Gln Glu Glu Glu Phe Asn
            740                 745                 750
Leu Thr Ala Leu Ala Leu Glu Asn Gly Thr Glu Phe Val Ser Ser Asn
                755                 760                 765
Thr Asp Ile Ile Val Gly Ser Asn Tyr Ser Ser Pro Ser Asn Ile Ser
770                 775                 780
Lys Phe Thr Val Asn Asn Leu Ala Glu Pro Gln Lys Ala Pro Ser His
785                 790                 795                 800
Gln Gln Ala Thr Thr Ala Gly Ser Pro Leu Arg His Leu Ile Gly Lys
                805                 810                 815
Asn Ser Val Leu Asn Ser Ser Thr Ala Glu His Ser Ser Pro Tyr Ser
            820                 825                 830
Glu Asp Pro Ile Glu Asp Pro Leu Gln Pro Asp Val Thr Gly Ile Arg
        835                 840                 845
Leu Leu Ser Leu Gly Ala Gly Glu Phe Lys Ser Gln Glu His Ala Lys
850                 855                 860
His Lys Gly Pro Lys Val Glu Arg Asp Gln Ala Ala Lys His Arg Phe
865                 870                 875                 880
Ser Trp Met Lys Leu Leu Ala His Lys Val Gly Arg His Leu Ser Gln
                885                 890                 895
Asp Thr Gly Ser Pro Ser Gly Met Arg Pro Trp Glu Asp Leu Pro Ser
            900                 905                 910
Gln Asp Thr Gly Ser Pro Ser Arg Met Arg Pro Trp Lys Asp Pro Pro
        915                 920                 925
Ser Asp Leu Leu Leu Leu Lys Gln Ser Asn Ser Ser Lys Ile Leu Val
930                 935                 940
Gly Arg Trp His Leu Ala Ser Glu Lys Gly Ser Tyr Glu Ile Ile Gln
945                 950                 955                 960
Asp Thr Asp Glu Asp Thr Ala Val Asn Asn Trp Leu Ile Ser Pro Gln
                965                 970                 975
Asn Ala Ser Arg Ala Trp Gly Glu Ser Thr Pro Leu Ala Asn Lys Pro
            980                 985                 990
Gly Lys Gln Ser Gly His Pro Lys Phe Pro Arg Val Arg His Lys Ser
        995                 1000                1005
Leu Gln Val Arg Gln Asp Gly Gly Lys Ser Arg Leu Lys Lys Ser Gln
    1010                1015                1020
```

```
Phe Leu Ile Lys Thr Arg Lys Lys Lys Glu Lys His Thr His His
1025                1030                1035                1040

Ala Pro Leu Ser Pro Arg Thr Phe His Pro Leu Arg Ser Glu Ala Tyr
            1045                1050                1055

Asn Thr Phe Ser Glu Arg Arg Leu Lys His Ser Leu Val Leu His Lys
                1060                1065                1070

Ser Asn Glu Thr Ser Leu Pro Thr Asp Leu Asn Gln Thr Leu Pro Ser
1075                1080                1085

Met Asp Phe Gly Trp Ile Ala Ser Leu Pro Asp His Asn Gln Asn Ser
    1090                1095                1100

Ser Asn Asp Thr Gly Gln Ala Ser Cys Pro Pro Gly Leu Tyr Gln Thr
1105                1110                1115                1120

Val Pro Pro Glu Glu His Tyr Gln Thr Phe Pro Ile Gln Asp Pro Asp
                1125                1130                1135

Gln Met His Ser Thr Ser Asp Pro Ser His Arg Ser Ser Ser Pro Glu
            1140                1145                1150

Leu Ser Glu Met Leu Glu Tyr Asp Arg Ser His Lys Ser Phe Pro Thr
                1155                1160                1165

Asp Ile Ser Gln Met Ser Pro Ser Ser Glu His Glu Val Trp Gln Thr
1170                1175                1180

Val Ile Ser Pro Asp Leu Ser Gln Val Thr Leu Ser Pro Glu Leu Ser
1185                1190                1195                1200

Gln Thr Asn Leu Ser Pro Asp Leu Ser His Thr Thr Leu Ser Pro Glu
            1205                1210                1215

Leu Ile Gln Arg Asn Leu Ser Pro Ala Leu Gly Gln Met Pro Ile Ser
                1220                1225                1230

Pro Asp Leu Ser His Thr Thr Leu Ser Pro Asp Leu Ser His Thr Thr
            1235                1240                1245

Leu Ser Leu Asp Leu Ser Gln Thr Asn Leu Ser Pro Glu Leu Ser Gln
1250                1255                1260

Thr Asn Leu Ser Pro Ala Leu Gly Gln Met Pro Leu Ser Pro Asp Leu
1265                1270                1275                1280

Ser His Thr Thr Leu Ser Leu Asp Phe Ser Gln Thr Asn Leu Ser Pro
                1285                1290                1295

Glu Leu Ser His Met Thr Leu Ser Pro Glu Leu Ser Gln Thr Asn Leu
            1300                1305                1310

Ser Pro Ala Leu Gly Gln Met Pro Ile Ser Pro Asp Leu Ser His Thr
            1315                1320                1325

Thr Leu Ser Leu Asp Phe Ser Gln Thr Asn Leu Ser Pro Glu Leu Ser
1330                1335                1340

Gln Thr Asn Leu Ser Pro Ala Leu Gly Gln Met Pro Leu Ser Pro Asp
1345                1350                1355                1360

Pro Ser His Thr Thr Leu Ser Leu Asp Leu Ser Gln Thr Asn Leu Ser
                1365                1370                1375

Pro Glu Leu Ser Gln Thr Asn Leu Ser Pro Asp Leu Ser Glu Met Pro
            1380                1385                1390

Leu Phe Ala Asp Leu Ser Gln Ile Pro Leu Thr Pro Asp Leu Asp Gln
                1395                1400                1405

Met Thr Leu Ser Pro Asp Leu Gly Glu Thr Asp Leu Ser Pro Asn Phe
    1410                1415                1420

Gly Gln Met Ser Leu Ser Pro Asp Leu Ser Gln Val Thr Leu Ser Pro
1425                1430                1435                1440

Asp Ile Ser Asp Thr Thr Leu Leu Pro Asp Leu Ser Gln Ile Ser Pro
```

-continued

```
                1445                1450                1455
Pro Pro Asp Leu Asp Gln Ile Phe Tyr Pro Ser Glu Ser Ser Gln Ser
        1460                1465                1470

Leu Leu Leu Gln Glu Phe Asn Glu Ser Phe Pro Tyr Pro Asp Leu Gly
    1475                1480                1485

Gln Met Pro Ser Pro Ser Ser Pro Thr Leu Asn Asp Thr Phe Leu Ser
    1490                1495                1500

Lys Glu Phe Asn Pro Leu Val Ile Val Gly Leu Ser Lys Asp Gly Thr
1505                1510                1515                1520

Asp Tyr Ile Glu Ile Ile Pro Lys Glu Val Gln Ser Ser Glu Asp
            1525                1530                1535

Asp Tyr Ala Glu Ile Asp Tyr Val Pro Tyr Asp Asp Pro Tyr Lys Thr
            1540                1545                1550

Asp Val Arg Thr Asn Ile Asn Ser Ser Arg Asp Pro Asp Asn Ile Ala
        1555                1560                1565

Ala Trp Tyr Leu Arg Ser Asn Asn Gly Asn Arg Arg Asn Tyr Tyr Ile
    1570                1575                1580

Ala Ala Glu Glu Ile Ser Trp Asp Tyr Ser Glu Phe Val Gln Arg Glu
1585                1590                1595                1600

Thr Asp Ile Glu Asp Ser Asp Asp Ile Pro Glu Asp Thr Thr Tyr Lys
            1605                1610                1615

Lys Val Val Phe Arg Lys Tyr Leu Asp Ser Thr Phe Thr Lys Arg Asp
        1620                1625                1630

Pro Arg Gly Glu Tyr Glu Glu His Leu Gly Ile Leu Gly Pro Ile Ile
        1635                1640                1645

Arg Ala Glu Val Asp Asp Val Ile Gln Val Arg Phe Lys Asn Leu Ala
    1650                1655                1660

Ser Arg Pro Tyr Ser Leu His Ala His Gly Leu Ser Tyr Glu Lys Ser
1665                1670                1675                1680

Ser Glu Gly Lys Thr Tyr Glu Asp Asp Ser Pro Glu Trp Phe Lys Glu
            1685                1690                1695

Asp Asn Ala Val Gln Pro Asn Ser Ser Tyr Thr Tyr Val Trp His Ala
        1700                1705                1710

Thr Glu Arg Ser Gly Pro Glu Ser Pro Gly Ser Ala Cys Arg Ala Trp
    1715                1720                1725

Ala Tyr Tyr Ser Ala Val Asn Pro Glu Lys Asp Ile His Ser Gly Leu
    1730                1735                1740

Ile Gly Pro Leu Leu Ile Cys Gln Lys Gly Ile Leu His Lys Asp Ser
1745                1750                1755                1760

Asn Met Pro Val Asp Met Arg Glu Phe Val Leu Leu Phe Met Thr Phe
        1765                1770                1775

Asp Glu Lys Lys Ser Trp Tyr Tyr Glu Lys Lys Ser Arg Ser Ser Trp
        1780                1785                1790

Arg Leu Thr Ser Ser Glu Met Lys Lys Ser His Glu Phe His Ala Ile
    1795                1800                1805

Asn Gly Met Ile Tyr Ser Leu Pro Gly Leu Lys Met Tyr Glu Gln Glu
    1810                1815                1820

Trp Val Arg Leu His Leu Leu Asn Ile Gly Gly Ser Gln Asp Ile His
1825                1830                1835                1840

Val Val His Phe His Gly Gln Thr Leu Leu Glu Asn Gly Asn Lys Gln
            1845                1850                1855

His Gln Leu Gly Val Trp Pro Leu Leu Pro Gly Ser Phe Lys Thr Leu
        1860                1865                1870
```

```
Glu Met Lys Ala Ser Lys Pro Gly Trp Trp Leu Leu Asn Thr Glu Val
        1875                1880                1885

Gly Glu Asn Gln Arg Ala Gly Met Gln Thr Pro Phe Leu Ile Met Asp
        1890                1895                1900

Arg Asp Cys Arg Met Pro Met Gly Leu Ser Thr Gly Ile Ile Ser Asp
1905                1910                1915                1920

Ser Gln Ile Lys Ala Ser Glu Phe Leu Gly Tyr Trp Glu Pro Arg Leu
        1925                1930                1935

Ala Arg Leu Asn Asn Gly Gly Ser Tyr Asn Ala Trp Ser Val Glu Lys
        1940                1945                1950

Leu Ala Ala Glu Phe Ala Ser Lys Pro Trp Ile Gln Val Asp Met Gln
        1955                1960                1965

Lys Glu Val Ile Ile Thr Gly Ile Gln Thr Gln Gly Ala Lys His Tyr
        1970                1975                1980

Leu Lys Ser Cys Tyr Thr Thr Glu Phe Tyr Val Ala Tyr Ser Ser Asn
1985                1990                1995                2000

Gln Ile Asn Trp Gln Ile Phe Lys Gly Asn Ser Thr Arg Asn Val Met
        2005                2010                2015

Tyr Phe Asn Gly Asn Ser Asp Ala Ser Thr Ile Lys Glu Asn Gln Phe
        2020                2025                2030

Asp Pro Pro Ile Val Ala Arg Tyr Ile Arg Ile Ser Pro Thr Arg Ala
        2035                2040                2045

Tyr Asn Arg Pro Thr Leu Arg Leu Glu Leu Gln Gly Cys Glu Val Asn
        2050                2055                2060

Gly Cys Ser Thr Pro Leu Gly Met Glu Asn Gly Lys Ile Glu Asn Lys
2065                2070                2075                2080

Gln Ile Thr Ala Ser Ser Phe Lys Lys Ser Trp Trp Gly Asp Tyr Trp
        2085                2090                2095

Glu Pro Phe Arg Ala Arg Leu Asn Ala Gln Gly Arg Val Asn Ala Trp
        2100                2105                2110

Gln Ala Lys Ala Asn Asn Asn Lys Gln Trp Leu Glu Ile Asp Leu Leu
        2115                2120                2125

Lys Ile Lys Lys Ile Thr Ala Ile Ile Thr Gln Gly Cys Lys Ser Leu
        2130                2135                2140

Ser Ser Glu Met Tyr Val Lys Ser Tyr Thr Ile His Tyr Ser Glu Gln
2145                2150                2155                2160

Gly Val Glu Trp Lys Pro Tyr Arg Leu Lys Ser Ser Met Val Asp Lys
        2165                2170                2175

Ile Phe Glu Gly Asn Thr Asn Thr Lys Gly His Val Lys Asn Phe Phe
        2180                2185                2190

Asn Pro Pro Ile Ile Ser Arg Phe Ile Arg Val Ile Pro Lys Thr Trp
        2195                2200                2205

Asn Gln Ser Ile Thr Leu Arg Leu Glu Leu Phe Gly Cys Asp Ile Tyr
        2210                2215                2220

<210> SEQ ID NO 32
<211> LENGTH: 560
<212> TYPE: PRT
<213> ORGANISM: Homo sapiens

<400> SEQUENCE: 32

Met Phe Ala Arg Met Ser Asp Leu His Val Leu Leu Leu Met Ala Leu
1               5                   10                  15

Val Gly Lys Thr Ala Cys Gly Phe Ser Leu Met Ser Leu Leu Glu Ser
                20                  25                  30
```

```
Leu Asp Pro Asp Trp Thr Pro Asp Gln Tyr Asp Tyr Ser Tyr Glu Asp
         35                  40                  45

Tyr Asn Gln Glu Glu Asn Thr Ser Ser Thr Leu Thr His Ala Glu Asn
     50                  55                  60

Pro Asp Trp Tyr Tyr Thr Glu Asp Gln Ala Asp Pro Cys Gln Pro Asn
 65                  70                  75                  80

Pro Cys Glu His Gly Gly Asp Cys Leu Val His Gly Ser Thr Phe Thr
                 85                  90                  95

Cys Ser Cys Leu Ala Pro Phe Ser Gly Asn Lys Cys Gln Lys Val Gln
             100                 105                 110

Asn Thr Cys Lys Asp Asn Pro Cys Gly Arg Gly Gln Cys Leu Ile Thr
         115                 120                 125

Gln Ser Pro Pro Tyr Tyr Arg Cys Val Cys Lys His Pro Tyr Thr Gly
     130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
                 165                 170                 175

Ala Cys Pro Asp Gln Phe Lys Gly Lys Phe Cys Glu Ile Gly Ser Asp
             180                 185                 190

Asp Cys Tyr Val Gly Asp Gly Tyr Ser Tyr Arg Gly Lys Met Asn Arg
         195                 200                 205

Thr Val Asn Gln His Ala Cys Leu Tyr Trp Asn Ser His Leu Leu Leu
     210                 215                 220

Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                 245                 250                 255

Cys Phe Ile Lys Val Thr Asn Asp Lys Val Lys Trp Glu Tyr Cys Asp
             260                 265                 270

Val Ser Ala Cys Ser Ala Gln Asp Val Ala Tyr Pro Glu Glu Ser Pro
         275                 280                 285

Thr Glu Pro Ser Thr Lys Leu Pro Gly Phe Asp Ser Cys Gly Lys Thr
     290                 295                 300

Glu Ile Ala Glu Arg Lys Ile Lys Arg Ile Tyr Gly Gly Phe Lys Ser
305                 310                 315                 320

Thr Ala Gly Lys His Pro Trp Gln Ala Ser Leu Gln Ser Ser Leu Pro
                 325                 330                 335

Leu Thr Ile Ser Met Pro Gln Gly His Phe Cys Gly Gly Ala Leu Ile
             340                 345                 350

His Pro Cys Trp Val Leu Thr Ala Ala His Cys Thr Asp Ile Lys Thr
         355                 360                 365

Arg His Leu Lys Val Val Leu Gly Asp Gln Asp Leu Lys Lys Glu Glu
     370                 375                 380

Phe His Glu Gln Ser Phe Arg Val Glu Lys Ile Phe Lys Tyr Ser His
385                 390                 395                 400

Tyr Asn Glu Arg Asp Glu Ile Pro His Asn Asp Ile Ala Leu Leu Lys
                 405                 410                 415

Leu Lys Pro Val Asp Gly His Cys Ala Leu Glu Ser Lys Tyr Val Lys
             420                 425                 430

Thr Val Cys Leu Pro Asp Gly Ser Phe Pro Ser Gly Ser Glu Cys His
         435                 440                 445

Ile Ser Gly Trp Gly Val Thr Glu Thr Gly Lys Gly Ser Arg Gln Leu
     450                 455                 460
```

```
Leu Asp Ala Lys Val Lys Leu Ile Ala Asn Thr Leu Cys Asn Ser Arg
465             470             475             480

Gln Leu Tyr Asp His Met Ile Asp Asp Ser Met Ile Cys Ala Gly Asn
            485             490             495

Leu Gln Lys Pro Gly Gln Asp Thr Cys Gln Gly Asp Ser Gly Gly Pro
            500             505             510

Leu Thr Cys Glu Lys Asp Gly Thr Tyr Tyr Val Tyr Gly Ile Val Ser
        515             520             525

Trp Gly Leu Glu Cys Gly Lys Arg Pro Gly Val Tyr Thr Gln Val Thr
        530             535             540

Lys Phe Leu Asn Trp Ile Lys Ala Thr Ile Lys Ser Glu Ser Gly Phe
545             550             555             560
```